United States Patent
Schadt et al.

(10) Patent No.: US 7,632,951 B2
(45) Date of Patent: *Dec. 15, 2009

(54) INHIBITORS OF INTEGRIN $\alpha_v\beta_6$

(75) Inventors: Oliver Schadt, Rodenbach (DE); Alfred Jonczyk, Darmstadt (DE); Wolfgang Staehle, Ingelheim (DE); Simon Goodman, Griesheim (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/471,836

(22) PCT Filed: Feb. 21, 2002

(86) PCT No.: PCT/EP02/01836

§ 371 (c)(1),
(2), (4) Date: Sep. 15, 2003

(87) PCT Pub. No.: WO02/074730

PCT Pub. Date: Sep. 26, 2002

(65) Prior Publication Data

US 2004/0092454 A1 May 13, 2004

(51) Int. Cl.
*A61K 31/44* (2006.01)
*C07D 213/02* (2006.01)

(52) U.S. Cl. .................. 546/309; 546/304; 514/275; 514/352

(58) Field of Classification Search ............... 546/190, 546/337, 304, 309; 514/325, 275, 352, 362
See application file for complete search history.

(56) References Cited

U.S. PATENT DOCUMENTS 6,306,840 B1 * 10/2001 Adams et al. ............ 514/109
6,576,637 B1 * 6/2003 Holzemann et al. ...... 514/275
7,138,417 B2 * 11/2006 Staehle et al. ............ 514/349
2004/0010023 A1 1/2004 Stahle et al.

FOREIGN PATENT DOCUMENTS

| WO | WO 00/48996 | * | 8/2000 |
| WO | WO 0048996 | | 8/2000 |
| WO | WO 0216328 | | 2/2002 |

OTHER PUBLICATIONS

Expression of the beta 6 integrin subunit in development, neoplasia and tissue repair suggests a role in epithelia remodeling. Breuss et. al.*
NMR studies of Organic polymorphs and solvates—Robin Harris Nov. 2005.*
Dorwald F. A. Side Reactions in Organic Synthesis, 2005, Wiley: VCH, Weinheim p. IX of Preface.*
Goodman et al., "Nanomolar small molecule inhibitors for . . . ," J. Med. Chem., Jan. 31, 2002, pp. 1045-1051, vol. 45, XP002204360, the whole document.

* cited by examiner

*Primary Examiner*—Rita J Desai
(74) *Attorney, Agent, or Firm*—Millen, White, Zelano & Branigan, P.C.

(57) ABSTRACT

Novel biphenyl derivatives of the general formula (I) in which $R^1$, $R^{1'}$, $R^{1''}$, $R^2$, $R^{2'}$, $R^3$ and n are as defined in claim 1, their stereoisomers and their physiologically acceptable salts or solvates are novel integrin inhibitors which preferentially inhibit the $\alpha_v\beta_6$ integrin receptor. The novel compounds can be used, in particular, as medicaments.

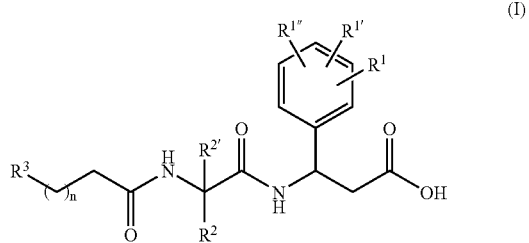

26 Claims, No Drawings

INHIBITORS OF INTEGRIN $\alpha_v\beta_6$

The invention relates to novel integrin inhibitors of the formula I

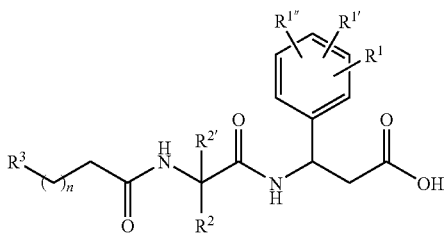

in which $R^1$, $R^{1'}$ and $R^{1''}$ are H, A, Ar, Het$^1$, Hal, NO$_2$, CN, OR$^4$, COA, NHCOA, NH(CHO), NR$^4$, COOR$^4$ or CONHR$^4{}_2$, $R^2$ is A, Ar, (CH$_2$)$_m$XA, (CH$_2$)$_m$OH, (CH$_2$)$_m$NH$_2$, (CH$_2$)$_m$NHA, (CH$_2$)$_m$NA$_2$, (CH$_2$)$_m$NHCOA, (CH$_2$)$_m$NO$_2$, (CH$_2$)$_m$COOR$^1$, (CH$_2$)$_m$CONH$_2$, (CH$_2$)$_m$X(CH$_2$)$_o$Ar, (CH$_2$)$_m$X(CH$_2$)$_o$CHAr$_2$, (CH$_2$)$_m$X(CH$_2$)$_o$CAr$_3$, (CH$_2$)$_m$XCOYA, (CH$_2$)$_m$XCOY(CH$_2$)$_o$Ar, (CH$_2$)$_m$X(CH$_2$)$_o$Het$^1$, (CH$_2$)$_m$X(CH$_2$)$_o$CHHet$^1{}_2$, (CH$_2$)$_m$X(CH$_2$)$_o$CHet$^1{}_3$, (CH$_2$)$_m$X(CH$_2$)$_o$YA, (CH$_2$)$_m$X(CH$_2$)$_o$NHCOA, (CH$_2$)$_m$NHCONHR$^{2'}$, (CH$_2$)$_m$CH$_2$A, (CH$_2$)$_m$CHA$_2$, (CH$_2$)$_m$CA$_3$, (CH$_2$)$_m$Ar, (CH$_2$)$_m$CHAr$_2$, (CH$_2$)$_m$CAr$_3$, (CH$_2$)$_m$Het$^1$, (CH$_2$)$_m$CHHet$^1{}_2$, (CH$_2$)$_m$CHet$^1{}_3$, (CH$_2$)$_m$cycloalkyl, (CH$_2$)$_m$—NH—C(=NH)—NH$_2$ or (CH$_2$)$_m$—(HN=)C—NH$_2$, where X and Y, independently of one another, may be S, O, S=O, SO$_2$ or NH, where, if R$^2$=(CH$_2$)$_m$XCOYA or (CH$_2$)$_m$XCOY(CH$_2$)$_o$Ar, X and Y cannot be S=O or SO$_2$, $R^{2'}$ is H or A, $R^2$ and $R^{2'}$ together may alternatively be —(CH$_2$)$_p$—, $R^3$ is H$_2$N—C(=NH)—, H$_2$N—C(=NH)—NH—, A-C(=NH)—NH—, Het$^2$- or Het$^2$-NH—, where the primary amino groups may also be provided with conventional amino-protecting groups, $R^4$ is H, A, Het$^1$, Hal, NO$_2$ or CN, A is alkyl having from 1 to 8 carbon atoms, Ar is phenyl, naphthyl, anthranyl or biphenyl, each of which is unsubstituted or monosubstituted or polysubstituted by Hal, A, OA, OH, CO-A, CN, COOA, COOH, CONH$_2$, CONHA, CONA$_2$, CF$_3$, OCF$_3$ or NO$_2$, Het$^1$ is an aromatic monocyclic or bicyclic heterocyclic radical having from 1 to 3 N, O and/or S atoms, which may be unsubstituted or monosubstituted or disubstituted by F, Cl, Br, A, OA, SA, OCF$_3$, —CO-A, CN, COOA, CONH$_2$, CONHA, CONA$_2$, NA$_2$ or NO$_2$, Het$^2$ is a monocyclic or bicyclic heterocyclic radical having from 1 to 4 N atoms, which may be unsubstituted or monosubstituted or disubstituted by NH$_2$ or NHA, m is 0, 1, 2, 3, 4, 5, 6 or 8, n is 1, 2, 3, 4, 5 or 6, o is 0, 1, 2 or 3, p is 2, 3, 4 or 5, to their stereoisomers, and to their physiologically acceptable salts and solvates.

Compounds having a partially similar structure are disclosed in WO 96/22966 A1, WO 97/08145 A1 and WO 00/48996 A2, where all compounds are effective as integrin inhibitors. Integrins are membrane-bound, heterodimeric glycoproteins which consist of an α-subunit and a smaller β-subunit. The relative affinity and specificity for ligand binding is determined by the combination of the different α- and β-subunits. According to the disclosure content of the said patent applications, the compounds of WO 96/22966 A1 selectively inhibit the $\alpha_4\beta_1$ integrin receptor, and the compounds of WO 97/08145 A1 selectively inhibit the $\alpha_v\beta_3$ integrin receptor. The compounds of WO 00/48996 A2 inhibit principally $\alpha_v\beta_3$ and $\alpha_v\beta_5$ integrin receptors.

The invention had the object of finding novel compounds having valuable properties, in particular those which are used for the preparation of medicaments.

It has been found that the compounds of the formula I and their salts have very valuable pharmacological properties and are well tolerated. Surprisingly, the novel compounds according to the invention preferentially inhibit the $\alpha_v\beta_6$ integrin receptor.

The integrins are ascribed various physiological and pathological functions, which are revealed in detail, for example, by the following review papers: *Integrins and signal transduction*. Dedhar-S, *Curr-Opin-Hematol*. 1999 January; 6(1): 37-43, *Integrins take partners: cross-talk between integrins and other membrane receptors*. Porter-J C; Hogg-N, *Trends-Cell-Biol*. 1998 October; 8(10): 390-6, *Regulation of integrin-mediated adhesion during cell migration*. Cox-E A; Huttenlocher-A, *Microsc-Res-Tech*. 1998 Dec. 1; 43(5): 412-9, *The role of integrins in the malignant phenotype of gliomas*. Uhm-J H; Gladson-C L; Rao-J S, *Front-Biosci*. 1999 Feb. 15; 4: D188-99, or *Sperm disintegrins, egg integrins, and other cell adhesion molecules of mammalian gamete plasma membrane interactions*. Evans-J P *Front-Biosci*. 1999 Jan. 15; 4: D114-31.

An important role here is ascribed to the $\alpha_v$ integrins, as found, for example, in *The role of alpha v-integrins in tumour progression and metastasis*. Marshall-J F; Hart-I R *Semin-Cancer-Biol*. 1996 June; 7(3): 129-38 or *The role of alpha v-integrins during angiogenesis*. Eliceiri-B P and Cheresh-D A *Molecular Medicine* 4: 741-750 (1998).

These integrins also include $\alpha_v\beta_6$-*Epithelial integrins*. Sheppard-D *Bioessays*. 1996 August; 18(8): 655-60 and the two integrins $\alpha_v\beta_3$ and $\alpha_v\beta_5$, which are known adhesion receptors, whose biological importance has been referred to, for example, in J. A. Varner et al. Cell Adhesion and Communication 3, 367-374 (1995) and in J. Samanen et al. Curr. Pharmaceutical Design, 3, 545-584 (1997).

$\alpha_v\beta_6$ is a relatively rare integrin (Busk et al., 1992 J. Biol. Chem. 267(9), 5790), which is increasingly formed in epithelial tissue during repair processes and preferentially binds the natural matrix molecules fibronectin and tenascin (Wang et al., 1996, Am. J. Respir. Cell Mol. Biol. 15(5), 664). In addition, vitronectin also binds to $\alpha_v\beta_6$ (*Characterization of the integrin alpha v beta 6 as a fibronectin-binding protein*. Busk-M; Pytela-R; Sheppard-D. *J-Biol-Chem*. 1992 Mar. 25; 267 (9): 5790-6; *Restricted distribution of integrin beta 6 mRNA in primate epithelial tissues*. Breuss,-J-M; Gillett,-N; Lu,-L; Sheppard,-D; Pytela,-R *J-Histochem-Cytochem*. 1993 October; 41(10): 1521-7; *Differential regulation of airway epithelial integrins by growth factors*. Wang-A; Yokosaki-Y; Ferrando-R; Balmes-J; Sheppard-D. *Am-J-Respir-Cell-Mol-Biol*. 1996 November; 15(5): 664-72); *The integrin alphavbeta6 is critical for keratinocyte migration on both its known ligand, fibronectin, and on vitronectin*. Huang,-X; Wu,-J; Spong,-S; Sheppard,-D *J-Cell-Sci*. 1998 August; 111 (Pt 15)2189-95).

The physiological and pathological functions of $\alpha_v\beta_6$ are still not known precisely, but it is assumed that this integrin plays an important role in physiological processes and disorders (for example inflammation, wound healing and tumours) in which epithelial cells are involved (*Expression of the beta 6 integrin subunit in development, neoplasia and tissue repair suggests a role in epithelial remodeling.* Breuss,-J-M; Gallo,-J; DeLisser,-H M; Klimanskaya,-I-V; Folkesson,-H-G; Pittet,-J-F; Nishimura,-S-L; Aldape,-K; Landers,-D-V; Carpenter,-W; et-al. *J-Cell-Sci* 1995 June; 108 (Pt 6)2241-51).

Thus, $\alpha_v\beta_6$ is expressed on keratinocytes in wounds (*Keratinocytes in human wounds express alpha v beta 6 integrin.* Haapasalmi-K, Zhang-K, Tonnesen-M, Olerud-J, Sheppard-D, Salo-T, Kramer-R, Clark-R A, Uitto-V J, Larjava-H. *J-Invest-Dermatol.* 1996 January, 106(1): 42-8; *Epidermal integrin expression is upregulated rapidly in human fetal wound repair.* Cass-D-L, Bullard-K-M, Sylvester-K-G, Yang-E-Y, Sheppard-D, Herlyn-M, Adzick-N-S *J-Pediatr-Surg.* 1998 February, 33(2): 312-6), from which it can be assumed that, besides wound-healing processes and inflammation, other pathological occurrences in the skin, such as, for example, psoriasis, can be influenced by agonists or antagonists of the said integrin.

Furthermore, in disturbed hornification of the skin (in the mucosa of the oral cavity, at the lips, the tongue and the genitals), so-called leukoplakia, $\alpha_v\beta_6$ is expressed to a greater extent compared with normal comparative tissue. The frequency and level of expression of the leukoplakia increases, via lichen planus, to squamous cell carcinoma, and consequently a correlation between expression of $\alpha_v\beta_6$ and the malign transformation of leukoplakia is assumed: *Expression of alpha(v)beta6 integrin in oral leukoplakia.* Hamidi-S, Salo-T, Kainulainen-T, Epstein-J, Lerner-K, Larjava-H *Br-J-Cancer.* 2000 April, 82(8): 1433-40; *Stromal fibroblasts influence oral squamous-cell carcinoma cell interactions with tenascin-C.* Ramos-D-M, Chen-B-L, Boylen-K, Stern-M, Kramer-R-H, heppard-D, Nishimura-S-L, Greenspan-D, Zardi-L, Pytela-R *Int-J-Cancer.* 1997 Jul. 17, 72(2): 369-76; Expression of the alpha v beta 6 integrin promotes migration and invasion in squamous carcinoma cells Thomas-G J, Lewis-M P, Whawell-S A, Russell-A, Sheppard-D, Hart-I R, Speight-P M, Marshall-J F *JOURNAL-OF-INVESTIGATIVE-DERMATOLOGY.* JULY 2001; 117 (1): 67-73; *Integrins alpha5beta1, alphavbeta1, and alphavbeta6 collaborate in squamous carcinoma cell spreading and migration on fibronectin.* Koivisto,-L, Grenman-R, Heino-J, Larjava-H *Exp-Cell-Res.* 2000 Feb. 25, 255(1): 10-7).

Furthermore, $\alpha_v\beta_6$ plays a role in the respiratory tract epithelium (Weinacker et al., 1995, *Am. J. Respir. Cell Mol. Biol.* 12(5), 547-56; *Expression of the human integrin beta6 subunit in alveolar type II cells and bronchiolar epithelial cells reverses lung inflammation in beta6 knockout mice.* Huang X, Wu J, Zhu W, Pytela R, Sheppard D, *Am-J-Respir-Cell-Mol-Biol.* 1998 Oct, 19(4): 636-42; *Expression of integrin cell adhesion receptors during human airway epithelial repair in vivo.* Pilewski J M, Latoche J D, Arcasoy S M, Albelda-S-M *Am-J-Physiol.* 1997 July, 273(1 Pt 1): L256-63; *Global analysis of gene expression in pulmonary fibrosis reveals distinct programs regulating lung inflammation and fibrosis.* Kaminski,-N; Allard J D, Pittet J F, Zuo F, Griffiths M J, Morris D, Huang X, Sheppard D, Heller R A, *Proc-Natl-Acad-Sci-U-S-A.* 2000 Feb. 15, 97(4): 1778-83), and consequently corresponding agonists/antagonists of this integrin could successfully be employed in respiratory tract disorders, such as bronchitis, asthma, lung fibrosis and respiratory tract tumours.

Besides the lung (bronchi), fibrosis may also occur in other organs, such as, for example, in the skin, the liver (extending to cirrhosis), the kidney and the bladder, the heart and the pancreas (cystic fibrosis). It is assumed that the integrin $\alpha_v\beta_6$ also plays a role in this pathological connective tissue proliferation, and the course of the illness can therefore be influenced by agonists/antagonists of integrin $\alpha_v\beta_6$ (*Mechanisms of tissue repair: from wound healing to fibrosis,* Mutsaers S E, Bishop J E, Mcgrouther G, Laurent G, *J Int. J. Biochem. Cell Biol.* (1997) 29(1): 5-17; *avb6 Integrin mediates latent TGFβ activation: Implications for cutaneous fibrosis.* Dalton S L, *J. Am. Acad. Dermatol* (1999) 41: 457-463; *Clinical significance of blood serum connective tissue components in organ fibrosis,* Kropf J, Gressner A M, Z. *Med. Laboratoriumsdiagn.* (1991) 32(3/4): 150-8; *Angiotensin II, adhesion, and cardiac fibrosis,* Schnee J M, Hsueh W A, *Cardiovasc. Res.* (2000) 46(2): 264-268; *Pulmonary fibrosis and its treatment: today and in the next millennium.* Sime P. J. *Curr. Opin. Anti-Inflammatory Immunomodulatory Invest. Drugs* (1999) 1(5): 423-432, *Hepatic fibrosis: pathophysiology and laboratory diagnosis,* Housset C, Guechot J, *Pathol. Biol.* (1999) 47(9): 886-894; *Progressive renal disease. Fibroblasts, extracellular matrix, and integrins,* Norman J T, Fine L G, *Exp. Nephrol.* (1999) 7(2): 167-177; *Renal fibrosis: insights into pathogenesis and treatment,* Nahas A M El, Muchaneta-Kubara E C, Essawy M, Soylemezoglu O, *Int. J. Biochem. Cell Biol.* (1997) 29(1): 55-62).

It is furthermore known that $\alpha_v\beta_6$ also plays a role in the intestinal epithelium, and consequently corresponding integrin agonists/antagonists could be used in the treatment of inflammation, tumours and wounds of the stomach/intestinal tract. There are indications here that integrin $\alpha_v\beta_6$ also influences the secretion of matrix metalloproteases, such as, for example, that of gelatinase B (MMP-9): *The alpha v beta 6 integrin promotes proliferation of colon carcinoma cells through a unique region of the beta 6 cytoplasmic domain,* Agrez M, Chen A, Cone R I, Pytela R, Sheppard D, *J Cell Biol* (1994) 127(2): 547-56; *Integrin-mediated signalling of gelatinase B secretion in colon cancer cells,* Niu J, Gu X, Turton J, Meldrum C, Howard E W, Agrez M, *Biochem Biophys Res Commun* (1998) 249(1): 287-91.

It has been found that the expression of $\alpha_v\beta_6$ is accompanied by changes in the cell density and MMP activity (*The alpha v beta 6 integrin regulates its own expression with cell crowding: Implications for tumour progression,* Niu J, Gu X, Ahmed N, Andrews S, Turton J, Bates R, Agrez M, *INTERNATIONAL JOURNAL OF CANCER,* (2001) 92 (1): 40-48; *The alpha v beta 6 integrin induces gelatinase B secretion in colon cancer cells,* Agrez M, Gu X, Turton J, Meldrum C, Niu J, Antalis T, Howard E W, *Int J Cancer* (1999) 81(1): 90-7; *alpha v beta 6 integrin upregulates matrix metalloproteinase 9 and promotes migration of normal oral keratinocytes,* Thomas G J, Poomsawat S, Lewis M P, Hart I R, Speight P M, Marshall J F, *JOURNAL OF INVESTIGATIVE DERMATOLOGY* (2001) 116 (6): 898-904; *alpha V beta 6 integrin promotes invasion of squamous carcinoma cells through up-regulation of matrix metalloproteinase-9,* Thomas G J, Lewis M P, Hart I R, Marshall J F, Speight P M, *INTERNATIONAL JOURNAL OF CANCER* (2001) 92 (5): 641-650). Regulation of the MMP activity (possibility different MMPS) by tumour cells as a function of their density could thus be a mechanism which enables the cells to re-create space for proliferation and migration by proteolysis of the surrounding matrix during growth of the tumour mass.

Owing to the role of integrin $\alpha_v\beta_6$ in infection processes, it is assumed that its agonists/antagonists can also be used in microbial infections (protozoa, microphytes, bacteria, viruses, yeasts and fungi). The correlation with integrin $\alpha_v\beta_6$ has been described, for example, for the coxsackievirus or for infection of host cells with the foot-and-mouth disease virus (FMDV), which proceeds $\alpha_v\beta_3$-dependently, but can also take place $\alpha_v\beta_6$-dependently (*Integrin alpha v beta 6 enhances coxsackievirus B1 lytic infection of human colon cancer cells.* Agrez M V, Shafren D R, Gu X, Cox K, Sheppard D, Barry R D, *Virology* (1997) 239(1): 71-7; *The epithelial integrin alphavbeta6 is a receptor for foot-and-mouth disease virus,* Jackson T, Sheppard D, Denyer M, Blakemore W, King A M, *J Virol* (2000) 11: 4949-56; *Role of the cytoplasmic domain of the beta-subunit of integrin alpha(v)beta6 in infection by foot-and-mouth disease virus,* Miller L C, Blakemore W, Sheppard D, Atakilit A, King A M, Jackson T, *J Virol* (2001) 75(9): 4158-64; *The ability of integrin avb3 to function as a receptor for foot-and-mouth disease virus is not dependent on the presence of complete subunit cytoplasmic domains,* Neff S, Baxt B, *J Virol* (2001) 75(1): 527-532; *Foot-and-mouth disease virus virulent for cattle utilizes the integrin avb3 as its receptor,* Neff S, Sa-Carvalho D, Rieder E, Mason, P W, Blystone S D, Brown E J, Baxt B, *J Virol* (1998) 72(5): 3587-3594; *Arginine-glycine-aspartic acid-specific binding by foot-and-mouth disease viruses to the purified integrin avb3 in vitro,* Jackson T, Sharma A, Ghazaleh R A, Blakemore W E, Ellard F M, Simmons D L, Newman J W I, Stuart D I, King A M Q, *J Virol* (1997) 71(11): 8357-8361).

Infection with HIV (AIDS) is also dependent on $\alpha_v\beta$ integrins, and consequently the agonists/antagonists of integrin $\alpha_v\beta_6$ would likewise be employed here (*A novel integrin specificity for the human immunodeficiency virus (HIV) Tat protein,* Ruoslahti E I, Vogel B E, Wong-Staal F Y, PCT Int. Appl (1992) WO 9214755).

According to more recent knowledge, the bacterium Bacillus anthracis secretes a toxin which consists of 3 proteins, one of which, the so-called PA or protective antigen, binds to receptors on the cell membrane (anthrax toxin receptor, ATR). ATR is a type I membrane protein with an extracellular domain of the Willebrandt factor type (vWF A). Integrins also contain vWF A domains of this type. This is comprehensible via a homology analysis in the Swiss Prot database both for integrin $\alpha_v\beta_6$ (http://www.expasy.ch/cgi-bin/niceprot.pl?P18564; sequence $\beta_6$ (131-371)) here, and also for $\alpha_v\beta_3$ (http://www.expasy.ch/cgi-bin/niceprot.pl?P05106; $\beta_3$ (135-377)). It is therefore assumed that $\alpha_v\beta_6$ agonists/antagonists can also be used for anthrax of the lung, skin and intestine) (*Identification of the cellular receptor for anthrax toxin.* K. A. Bradley et al. *Nature* 414, 225-229 (2001) [and accompanying articles]; *Evolution of von Willebrand factor A (vWA) domains,* Tuckwell D, *Biochem Soc Trans* (1999) 27(6): 835-840).

The dependence of the infection of host cells on their adhesion receptors for bacteria and for yeasts (budding fungi, candida) (*Cell adhesion molecules in the pathogenesis of and host defence against microbial infection,* Kerr J R, Medical Microbiology, Manchester Royal Infirmary, UK, *MOLECULAR PATHOLOGY* (1999) 52(4): 220-30; *Vitronectin-dependent invasion of epithelial cells by Neisseria gonorrhoeae involves alpha(v) integrin receptors,* Dehio M, Gomez-Duarte O G, Dehio C, Meyer T F, *FEBS LETTERS* (1998) 424 (1-2): 84-8; *A natural variant of the cysteine protease virulence factor of group A Streptococcus with an arginineglycine-aspartic acid (RGD) motif preferentially binds human integrins alphavbeta3 and alphaIIbbeta3,* Stockbauer K E, Magoun L, Liu M, Burns E H Jr, Gubba S, Renish S, Pan X, Bodary S C, Baker E, Coburn J, Leong J M, Musser J M, *PROCEEDINGS OF THE NATIONAL ACADEMY OF SCIENCES OF THE UNITED STATES OF AMERICA* (1999), 96(1): 242-7; *Involvement of alpha(v)beta3 integrin-like receptor and glycosaminoglycans in Candida albicans germ tube adhesion to vitronectin and to a human endothelial cell line,* Santoni G, Spreghini E, Lucciarini R, Amantini C, Piccoli M, *MICROBIAL PATHOGENESIS* (2001) 31(4): 159-72) indicates the possibility of using agonists/antagonists of integrin $\alpha_v\beta_6$ in these cases too.

Integrin $\alpha_v\beta_6$ interacts with TGF-$\beta$, resulting in its activation (*avb6 Integrin mediates latent TGFβ activation: Implications for cutaneous fibrosis,* Dalton S L, *J Am Acad Dermatol* (1999) 41: 457-463; *The integrin avb6 binds and activates latent TGFb1: a mechanism for regulating pulmonary inflammation and fibrosis,* Munger J S et al. *Cell* (1999) 96: 319-328). Latent TGF$\beta_1$ (one of the pro-forms) binds to integrin $\alpha_v\beta_6$ and is proteolytically activated thereby. The integrin $\alpha_v\beta_6$ agonists/antagonists according to the invention could thus prevent activation of TGF-$\beta_1$ and other sub-types by inhibiting the binding of TGF-$\beta$ (pro-form, LAP peptide, LAP-TGF$\beta$, latent TGF) and thereby modulate the effect of TGF$\beta$.

3 human TGF$\beta$ isoforms have been discovered to date, which are ascribed a role in a multiplicity of growth and differentiation processes, but in particular in inflammatory processes, fibrosis, wound healing, bone growth, the modulation of immunofunctions, in angiogenesis and tumour metastasis (Rifkin D B et al., *Thrombosis and Haemostasis* (1993) 70: 177-179; Hata A et al., *Molecular Medicine Today* (June 1998) 257-262; *Integrin-mediated activation of transforming growth factor-beta(1) in pulmonary fibrosis,* Sheppard D C, (2001) 120(1 Suppl): 49S-53S; Wickstom P et al., *Prostate* (1998) 37: 19-29). The $\alpha_v\beta_6$ agonists/antagonists according to the invention could thus also be employed in these processes.

A further paper which emphasises the role of $\alpha_v\beta_6$ in immunological processes describes the influx of neutrophiles after chemical damage to the lung (*Expression of the beta6 integrin subunit is associated with sites of neutrophil influx in lung epithelium,* Miller L A, Barnett N L, Sheppard D, Hyde D M, *J Histochem Cytochem* (2001) 49(1): 41-8).

The effect of a compound on an $\alpha_v\beta_6$ integrin receptor and thus on the activity as an inhibitor can be demonstrated, for example, by the method described by J. W. Smith et al. in J. Biol. Chem. 1990, 265, 12267-12271.

Besides the preferred inhibition of $\alpha_v\beta_6$ integrin receptors, the compounds also act as inhibitors of $\alpha_v\beta_3$ or $\alpha_v\beta_5$ integrin receptors and as inhibitors of glycoprotein IIb/IIIa. Integrin $\alpha_v\beta_3$, for example, is expressed on a number of cells, for example endothelial cells, cells of the smooth vascular muscles, for example of the aorta, cells for the breakdown of bone matrix (osteoclasts) or tumour cells.

The action of the compounds according to the invention can be demonstrated, for example, by the method described by J. W. Smith et al. in J. Biol. Chem. 1990, 265, 12267-12271.

The dependence of formation of angiogenesis on the interaction between vascular integrins and extracellular matrix proteins has been described by P. C. Brooks, R. A. Clark and D. A. Cheresh in Science 1994, 264, 569-571.

The possibility of inhibiting this interaction and so initiating apoptosis (programmed cell death) of angiogenic vascular cells by a cyclic peptide has been described by P. C. Brooks, A. M. Montgomery, M. Rosenfeld, R. A. Reisfeld, T. Hu, G. Klier and D. A. Cheresh in Cell 1994, 79, 1157-1164. In this, for example, $\alpha$v$\beta$3 antagonists or antibodies against $\alpha$v$\beta$3 were described which cause shrinkage of tumours due to the initiation of apoptosis.

The experimental evidence that the compounds according to the invention also prevent the attachment of living cells to the corresponding matrix proteins and accordingly also prevent the attachment of tumour cells to matrix proteins can be provided in a cell adhesion test analogously to the method of F. Mitjans et al., J. Cell Science 1995, 108, 2825-2838.

The compounds of the formula I are able to inhibit the binding of metalloproteinases to integrins and thus prevent the cells utilising the enzymatic activity of the proteinase. An example can be found in the ability of a cyclo-RGD peptide to inhibit the binding of MMP-2 (matrix-metalloproteinase-2) to the vitronectin receptor αvβ3, as described in P. C. Brooks et al., Cell 1996, 85, 683-693.

Compounds of the formula I which block the interaction of integrin receptors and ligands, such as, for example, of fibrinogen to the fibrinogen receptor (glycoprotein IIb/IIIa), prevent, as antagonists, the spread of tumour cells by metastasis and can therefore be employed as antimetastatic substances in operations in which tumours are removed or attacked surgically. This is confirmed by the following observations:

The spread of tumour cells from a local tumour into the vascular system occurs through the formation of microaggregates (microthromboses) due to the interaction of the tumour cells-with blood platelets. The tumour cells are masked by the protection in the microaggregate and are not recognised by the immune system cells. The microaggregates are able to attach to vessel walls, simplifying further penetration of tumour cells into the tissue. Since the formation of microthromboses is promoted by ligand binding to the corresponding integrin receptors, for example αvβ3 or αIIbβ3, on activated blood platelets, the corresponding antagonists can be regarded as effective metastasis inhibitors.

The action of a compound on an αvβ5 integrin receptor and thus the activity as an inhibitor can be demonstrated, for example, by the method described by J. W. Smith et al. in J. Biol. Chem. 1990, 265, 12267-12271.

A measure of the uptake of a medicament active ingredient in an organism is its bioavailability.

If the medicament active ingredient is administered to the organism intravenously in the form of an injection solution, its absolute bioavailability, i.e. the proportion of the pharmaceutical species which is unchanged in the systemic blood, i.e. enters the general circulation, is 100%.

On oral administration of a therapeutic active ingredient, the active ingredient is generally in the form of a solid in the formulation and must therefore first dissolve in order that it can overcome the entry barriers, for example the gastrointestinal tract, the oral mucous membrane, nasal membranes or the skin, in particular the stratum corneum, and can be absorbed by the body. Pharmacokinetic data, i.e. on the bioavailability, can be obtained analogously to the method of J. Shaffer et al., J. Pharm. Sciences, 1999, 88, 313-318.

A further measure of the absorbability of a therapeutic active ingredient is the logD value, since this value is a measure of the lipophilicity of a molecule.

The compounds of the formula I have at least one centre of chirality and can therefore occur in a number of stereoisomeric forms. All of these forms (for example D and L forms) and mixtures thereof (for example the DL forms) are included in the formula.

The compounds according to the invention also include so-called prodrug derivatives, i.e. compounds of the formula I modified with, for example, alkyl or acyl groups, sugars or oligopeptides, which are rapidly cleaved in the organism to give the effective compounds according to the invention.

Furthermore, free amino groups or free hydroxyl groups can be provided as substituents of compounds of the formula I with corresponding protecting groups.

The term solvates of the compounds of the formula I is taken to mean adductions of inert solvent molecules onto the compounds of the formula I which form owing to their mutual attractive force. Solvates are, for example, mono- or dihydrates or addition compounds with alcohols, such as, for example, with methanol or ethanol.

The invention relates to the compounds of the formula I and their salts and solvates and to a process for the preparation of compounds of the formula I and their salts and solvates, characterised in that (a) a compound of the formula II

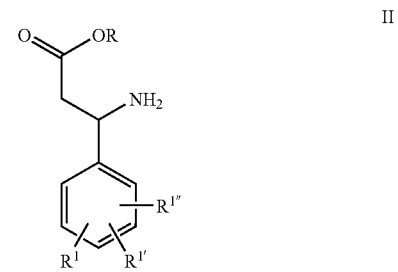

in which R is a protecting group, and $R^1$, $R^{1'}$ and $R^{1''}$ are as defined in formula I and in which, in the case where $R^1$, $R^{1'}$ and/or $R^{1''}$ has a free hydroxyl or amino group, this is in each case protected by a protecting group, is reacted with a compound of the formula III

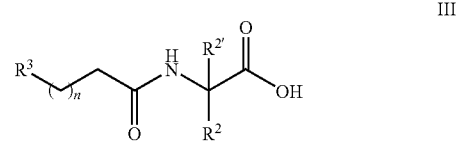

in which $R^2$, $R^{2'}$, $R^3$ and n are as defined in formula I and in which, in the case where $R^2$, $R^{2'}$ and/or $R^3$ contain free hydroxyl or amino groups, these are in each case protected by protecting groups, and the protecting group R and any protecting groups present on $R^1$, $R^{1'}$, $R^{1''}$, $R^2$, $R^{2'}$ and/or $R^3$ are removed, or (b) a compound of the formula IV

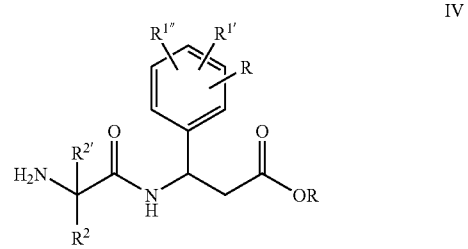

in which R is a protecting group, and $R^1$, $R^{1'}$, $R^{1''}$, $R^2$ and $R^{2'}$ are as defined in formula I and in which, in the case where $R^1$, $R^{1'}$, $R^{1''}$, $R^2$ and/or $R^{2'}$ contain free hydroxyl and/or amino groups, these are in each case protected by protecting groups, is reacted with a compound of the formula V

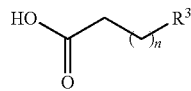

in which n and $R^3$ are as defined in formula I and in which, in the case where $R^1$, $R^{1'}$ and/or $R^{1''}$ contains free hydroxyl and/or amino groups, these are in each case protected by protecting groups, and the protecting group R and any protecting groups present on $R^1$, $R^{1'}$, $R^{1''}$, $R^2$ and/or $R^3$ are removed, or (c) one or more radicals $R^1$, $R^{1'}$, $R^{1''}$, $R^2$ and/or $R^3$ in a compound of the formula I are converted into one or more radicals $R^1$, $R^{1'}$, $R^{1''}$, $R^2$ and/or $R^3$
by, for example,
i) alkylating a hydroxyl group,
ii) hydrolysing an ester group to a carboxyl group,
iii) esterifying a carboxyl group,
iv) alkylating an amino group,
v) reacting an aryl bromide or iodide with boronic acids by a Suzuki coupling to give the corresponding coupling products, or
vi) acylating an amino group, or (d) a compound of the formula II is reacted with a compound of the formula VI

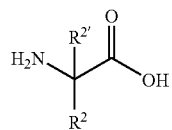

in which $R^2$ and $R^{2'}$ are as defined in formula I and in which, in the case where $R^2$ and/or $R^{2'}$ contain free hydroxyl and/or amino groups, these are protected by protecting groups,
to give a compound of the formula IV,
the compound of the formula IV is reacted with a compound of the formula V as described in (b),
and the protecting group R and any protecting groups present on $R^1$, $R^{1'}$, $R^{1''}$, $R^2$, $R^{2'}$ and/or $R^3$ are removed, and/or a basic or acidic compound of the formula I is converted into one of its salts or solvates by treatment with an acid or base.

Throughout the invention, all radicals which occur more than once, such as, for example, A, may be identical or different, i.e. are independent of one another.

In the above formulae, A is alkyl, is linear or branched, and has from 1 to 8, preferably 1, 2, 3, 4, 5 or 6 carbon atoms. A is preferably methyl, furthermore ethyl, n-propyl, isopropyl, n-butyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl or octyl. Further preferred embodiments of A are the said alkyl groups, which, however, may be monosubstituted or polysubstituted by Hal or $NO_2$, preferably trifluoromethyl, 2,2,2-trifluoroethyl or 2-nitroethyl, or alkyl groups, whose carbon chain may be interrupted by —O—, preferably —$CH_2$—O—$CH_3$, —$CH_2$—O—$CH_2$—$CH_3$ or —$CH_2$—$CH_2$—O—$CH_3$.

A is particularly preferably methyl or ethyl.

$R^3$ is preferably, for example, pyrimidin-2-ylamino, pyridin-2-ylamino, imidazol-1-yl, imidazol-2-ylamino, benzimidazol-2-ylamino, 4,5-dihydro-imidazol-2-ylamino, 2-aminoimidazol-5-ylamino, 2-aminopyridin-6-ylamino, 2-aminoimidazol-5-yl or 2-aminopyridin-6-yl.

$R^1$ is preferably, for example, phenyl.

Ar is unsubstituted, preferably—as indicated—monosubstituted phenyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-methylthiophenyl, o-, m- or p-methylsulfinyl-phenyl, o-, m- or p-methylsulfonylphenyl, o-, m- or p-aminophenyl, o-, m- or p-methylaminophenyl, o-, m- or p-dimethylaminophenyl, o-, m- or p-nitrophenyl, o-, m- or p-acetylphenyl, o-, m- or p-methoxycarbonylphenyl, o-, m- or p-aminocarbonylphenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 2,3,4-, 2,3,5-, 2,3,6-, 2,4,6- or 3,4,5-trichlorophenyl, 2,4,6-tri-tert-butylphenyl, 2,5-dimethylphenyl, p-iodophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl or 2,4,6-triisopropylphenyl.

Cycloalkyl having from 3 to 15 carbon atoms is preferably cyclopropyl, cyclobutyl, cyclopentyl, cyclohexyl, cycloheptyl or cyclooctyl, particularly preferably cyclohexyl. Cycloalkyl is likewise a monocyclic or bicyclic terpene, preferably p-menthane, menthol, pinane, bornane or camphor, where each known stereoisomeric form is included, or adamantyl. For camphor, this is both L-camphor and D-camphor. Cycloalkyl is particularly preferred.

Hal is preferably F, Cl, Br or iodine. Hal is particularly preferably F or Cl.

The amino-protecting group is preferably formyl, acetyl, propionyl, butyryl, phenylacetyl, benzoyl, tolyl, POA, methoxycarbonyl, ethoxycarbonyl, 2,2,2-trichloroethoxycarbonyl, BOC, 2-iodoethoxycarbonyl, CBZ ("carbo-benzoxy"), 4-methoxybenzyloxycarbonyl, FMOC, Mtr or benzyl.

$Het^1$ is preferably 2,3-, 2,4-, 2,5- or 3,4-thienyl, 2,3-, 2,4-, 2,5- or 3,4-pyrrolyl, 2,4-, 2,5- or 4,5-imidazolyl, 2,3-, 2,4-, 2,6- or 3,5-pyridyl, 2,4-, 2,5-, 2,6-, 4,5- or 5,6-pyrimidinyl, 1-, 2-, 3-, 4-, 5-, 6- or 7-indolyl, each of which is unsubstituted or monosubstituted by F, Cl, Br, A, OA or $OCF_3$. Pyridylamino is particularly preferred.

Het² is preferably 1-, 2- or 3-pyrrolyl, 1-, 2-, 4- or 5-imidazolyl, 1-, 3-, 4- or 5-pyrazolyl, 2-, 3- or 4-pyridyl, 2-, 4-, -5- or 6-pyrimidinyl, furthermore preferably 1,2,3-triazol-1-, -4- or -5-yl, 1,2,4-triazol-1-, -3- or 5-yl, 1- or 5-tetrazolyl, 3- or 4-pyridazinyl, pyrazinyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 1H-imidazo[4,5-b]pyridin-2-yl or 1,8-naphthyridin-7-yl, each of which is unsubstituted or monosubstituted or disubstituted by A, NHA and/or $NH_2$. 4-pyridyl is particularly preferred.

The heterocyclic radicals may also be partially or fully hydrogenated. Het² may thus also be, for example, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or 4-imidazolyl, 4,5-dihydroimidazol-2-yl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, morpholinyl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl or 1,2,3,4-tetrahydro-1,8-naphthyridin-7-yl. Hydrogenated or partially hydrogenated Het² radicals may additionally be substituted by =NH or carbonyl oxygen.

n is preferably 2, 3, 4, 5 or 6, and n is very particularly preferably 2, 3 or 4. m is preferably 0, 1, 2, 3 or 4, and m is very particularly preferably 0, 1 or 2. o is preferably 0, 1 or 2; and o is very particularly preferably 1.

"Poly"substituted means mono-, di-, tri- or tetrasubstituted.

Pol is a solid phase with no terminal functional group, as explained in greater detail below. The terms solid phase and resin are used synonymously below.

If the compounds of the formula I contain biphenyl, the second phenyl radical is preferably coupled to the first phenyl radical in the 3- or 4-position, particularly preferably to the 4-position of the first phenyl ring.

Accordingly, the invention relates in particular to the compounds of the formula I in which at least one of the said radicals has one of the preferred meanings indicated above. Some preferred groups of compounds may be expressed by the following sub-formulae Ia to It, which conform to the formula I and in which the radicals not designated in greater detail have the meaning indicated under the formula I, but in which in Ia) $R^3$ is pyrimidin-2-ylamino, pyridin-2-ylamino, imidazol-1-yl, imidazol-2-ylamino, benzimidazol-2-ylamino, 4,5-dihydroylamino, 2-aminopyridin-6-ylamino, 2-aminoimidazol-5-yl or 2-aminopyridin-6-yl;

in Ib) $R^3$ is $H_2N$—C(=NH)—, $H_2N$—C(=NH)—NH— or Het²NH;

in Ic) $R^3$ is $H_2N$—C(=NH)—, $H_2N$—C(=NH)—NH— or Het²NH, in which
Het² is a 5- or 6-membered aromatic or saturated heterocyclic radical having 1 or 2 N and/or O atoms;

in Id) $R^3$ is $H_2N$—C(=NH)—, $H_2N$—C(=NH)—NH— or Het²NH, in which
Het² is pyridyl;

in Ie) $R^3$ is Het²NH, in which
Het² is pyridyl;

in If) $R^1$, $R^{1'}$ and $R^{1''}$ are H, Ar, Het¹Hal, $NR^4$ and/or $CONHR^4_2$, in which
$R^4$ is H, A or Het¹;

in Ig) $R^1$ is Ar;

in Ih) $R^1$ is Ar, in which
Ar is a phenyl radical which is unsubstituted or monosubstituted or disubstituted by A, OA, OH, Hal or $CF_3$,
$R^{1'}$ and $R^{1''}$ are each H;

in Ii) $R^1$ is Ar, in which
Ar is phenyl,
$R^{1'}$ and $R^{1''}$ are each H;

in Ij) $R^3$ is $H_2N$—C(=NH)—, $H_2N$—C(=NH)—NH— or Het²NH, in which
Het² is pyridyl,
$R^1$ is Ar, in which
Ar is a phenyl radical which is unsubstituted or monosubstituted or disubstituted by A, OA, OH, Hal or $CF_3$,
n is 2, 3 or 4;

in Ik) $R^2$ is A, Ar, $(CH_2)_mXA$, $(CH_2)_mOH$, $(CH_2)_mNH_2$, $(CH_2)_mNHA$, $(CH_2)_mNA_2$, $(CH_2)_mNHCOA$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mX$-COYA, $(CH_2)_mXCOY(CH_2)_oAr$, $(CH_2)_mX(CH_2)_oHet^1$, $(CH_2)_mX(CH_2)_oCHHet^1_2$, $(CH_2)_mX(CH_2)_oCHet^1_3$, $(CH_2)_mX(CH_2)_oYA$, $(CH_2)_mX(CH_2)_oNHCOA$, $(CH_2)_mN$-HCONHR²', $(CH_2)_mAr$, $(CH_2)_mCHAr_2$, $(CH_2)_mCAr_3$, $(CH_2)_mHet^1$, $(CH_2)_mCHHet^1_2$, $(CH_2)_mCHet^1_3$, $(CH_2)_m$cycloalkyl, $(CH_2)_m$—NH—C(=NH)—$NH_2$ or $(CH_2)_m$—(HN=)C—$NH_2$, in which
X and Y, independently of one another, may be S, O, S=O, $SO_2$ or NH,
where, if $R^2$=$(CH_2)_mXCOYA$ or $(CH_2)_mXCOY(CH_2)_oAr$, X and Y cannot be S=O or $SO_2$;

in Il) $R^2$ is A, Ar, $(CH_2)_mXA$, $(CH_2)_mOH$, $(CH_2)_mNH_2$, $(CH_2)_m NHA$, $(CH_2)_mNA_2$, $(CH_2)_mNO_2$, $(CH_2)_mCOOR^1$, $(CH_2)_m CONH_2$, $(CH_2)_mX(CH_2)_oAr$, $(CH_2)_mX(CH_2)_o CHAr_2$, $(CH_2)_mX(CH_2)_oCAr_3$, $(CH_2)_mXCOYA$, $(CH_2)_m XCOY(CH_2)_oAr$, $(CH_2)_mX(CH_2)_oHet^1$, $(CH_2)_mX(CH_2)_o CHHet^1_2$, $(CH_2)_mX(CH_2)_oCHet^1_3$, $(CH_2)_mX(CH_2)_oYA$, $(CH_2)_mX(CH_2)_oNHCOA$, $(CH_2)_mNHCONHR^2$, $(CH_2)_m Ar$, $(CH_2)_mCHAr_2$, $(CH_2)_mCAr_3$, $(CH_2)_mHet^1$, $(CH_2)_m CHHet^1_2$, $(CH_2)_mCHet^1_3$, $(CH_2)_m$cycloalkyl, $(CH_2)_m$—NH—C(=NH)—$NH_2$ or $(CH_2)_m$—(HN=)C—$NH_2$, in which
$R^{2'}$ is H,
X and Y, independently of one another, may be S, O, S=O, $SO_2$ or NH,
where, if $R^2$=$(CH_2)_mXCOYA$ or $(CH_2)_mXCOY(CH_2)_oAr$, X and Y cannot be S=O or $SO_2$,
m is 1, 2, 3 or 4;

in Im) $R^2$ is A, Ar, $(CH_2)_mXA$, $(CH_2)_mOH$, $(CH_2)_mNH_2$, $(CH_2)_mNHA$, $(CH_2)_mNA_2$, $(CH_2)_mNO_2$, $(CH_2)_mCOOR^1$, $(CH_2)_mCONH_2$, $(CH_2)_mX(CH_2)_oAr$, $(CH_2)_mX(CH_2)_o CHAr_2$, $(CH_2)_mX(CH_2)_oCAr_3$, $(CH_2)_mXCOYA$, $(CH_2)_m XCOY(CH_2)_oAr$, $(CH_2)_mX(CH_2)_oHet^1$, $(CH_2)_mX(CH_2)_o CHHet^1_2$, $(CH_2)_mX(CH_2)_oCHet^1_3$, $(CH_2)_mX(CH_2)_oYA$, $(CH_2)_mX(CH_2)_oNHCOA$, $(CH_2)_mNHCONHR^{2'}$, $(CH_2)_m Ar$, $(CH_2)_mCHAr_2$, $(CH_2)_mCAr_3$, $(CH_2)_mHet^1$, $(CH_2)_m CHHet^1_2$, $(CH_2)_mCHet^1_3$, $(CH_2)_m$Cycloalkyl, $(CH_2)_m$—NH—C(=NH)—$NH_2$ or $(CH_2)_m$—(HN=)C—$NH_2$, in which
X and Y, independently of one another, may be S, O, S=O, $SO_2$ or NH,
where, if $R^2$=$(CH_2)_mXCOYA$ or $(CH_2)_mXCOY(CH_2)_oAr$, X and Y cannot be S=O or $SO_2$,
and in the case where X and Y are bonded directly to one another by a chemical bond, these are each S,
$R^{2'}$ is H,
m is 1, 2, 3 or 4,
o is 0, 1, 2 or 3;

in In) $R^2$ is A, Ar, $(CH_2)_mXA$, $(CH_2)_mOH$, $(CH_2)_mNH_2$, $(CH_2)_mNHA$, $(CH_2)_mNA_2$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mXCOYA$, $(CH_2)_mXCOY(CH_2)_oAr$, $(CH_2)_mX(CH_2)_oHet^1$, $(CH_2)_mX(CH_2)_oCHHet^1_2$, $(CH_2)_mX(CH_2)_oCHet^1_3$, $(CH_2)_mX(CH_2)_oYA$, $(CH_2)_mX(CH_2)_oNHCOA$, $(CH_2)_mNHCONHR^2$, $(CH_2)_mAr$, $(CH_2)_mCHAr_2$, $(CH_2)_mCAr_3$, $(CH_2)_mHet^1$, $(CH_2)_mCHHet^1_2$, $(CH_2)_mCHet^1_3$, $(CH_2)_mCycloalkyl$, $(CH_2)_m—NH—C(=NH)—NH_2$ or $(CH_2)_m—(HN=)C—NH_2$, in which $R^{2'}$ is H, $Het^1$ is a monocyclic or bicyclic, 5- and/or 6-membered aromatic or saturated heterocyclic radical having 1 or 2 N, S and/or O atoms, Ar is a phenyl radical which is unsubstituted or monosubstituted or disubstituted by A, OA, OH, Hal or $CF_3$, X and Y, independently of one another, may be S, O, S=O, $SO_2$ or NH, where, if $R^2=(CH_2)_mXCOYA$ or $(CH_2)_mXCOY(CH_2)_oAr$, X and Y, independently of one another, may be NH and/or O, and in the case where X and Y are bonded directly to one another by a chemical bond, these are each S;

m is 1, 2, 3 or 4, o is 0, 1, 2 or 3;

in Io) $R^2$ is A, Ar, $(CH_2)_mXA$, $(CH_2)_mOH$, $(CH_2)_mNH_2$, $(CH_2)_mNHA$, $(CH_2)_mNA_2$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mXCOYA$, $(CH_2)_mXCOY(CH_2)_oAr$, $(CH_2)_mX(CH_2)_oHet^1$, $(CH_2)_mX(CH_2)_oCHHet^1_2$ $(CH_2)_mX(CH_2)_oCHet^1_3$, $(CH_2)_mX(CH_2)_oYA$, $(CH_2)_mX(CH_2)_oNHCOA$, $(CH_2)_mNHCONR^{2'}$, $(CH_2)_mAr$, $(CH_2)_mCHAr_2$, $(CH_2)_mCAr_3$, $(CH_2)_mHet^1$, $(CH_2)_mCHHet^1_2$, $(CH_2)_mCHet^1_3$, $(CH_2)_mcycloalkyl$, $(CH_2)_m—NH—C(=NH)—NH_2$ or $(CH_2)_m—(HN=)C—NH_2$, in which $R^{2'}$ is H, $Het^1$ is imidazolyl, thiophenyl, pyridinyl or indolyl, Ar is phenyl or 4-OH-phenyl, X and Y, independently of one another, may be S, O, S=O, $SO_2$ or NH, where, if $R^2=(CH_2)_mXCOYA$ or $(CH_2)_mXCOY(CH_2)_oAr$, X=NH and Y=O, and in the case where X and Y are bonded directly to one another by a chemical bond, these are each S, m is 1, 2, 3 or 4, o is 0, 1, 2 or 3;

in Ip) $R^3$ is $H_2N—C(=NH)—$, $H_2N—C(=NH)—NH—$ or $Het^2NH$, $R^1$, $R^{1'}$ and $R^{1''}$ are H, Ar, $Het^1$Hal, $NR^4$ and/or $CONHR^4_2$, in which $R^4$ is H, A or $Het^1$, $R^2$ is A, Ar, $(CH_2)_mXA$, $(CH_2)_m$ OH, $(CH_2)_mNH_2$, $(CH_2)_mNHA$, $(CH_2)_mNA_2$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mXCOYA$, $(CH_2)_m XCOY(CH_2)_oAr$, $(CH_2)_mX(CH_2)_oHet^1$, $(CH_2)_mX(CH_2)_oCHHet^1_2$, $(CH_2)_mX(CH_2)_oCHet^1_3$, $(CH_2)_mX(CH_2)_oYA$, $(CH_2)_mX(CH_2)_oNHCOA$, $(CH_2)_mNHCONR^2$, $(CH_2)_mAr$, $(CH_2)_mCHAr_2$, $(CH_2)_mCAr_3$, $(CH_2)_mHet^1$, $(CH_2)_mCHHet^1_2$, $(CH_2)_mCHet^1_3$, $(CH_2)_mcycloalkyl$, $(CH_2)_m—NH—C(=NH)—NH_2$ or $(CH_2)_m—(HN=)C—NH_2$, in which X and Y, independently of one another, may be S, O, S=O, $SO_2$ or NH, where, if $R^2=(CH_2)_mXCOYA$ or $(CH_2)_mXCOY(CH_2)_oAr$, X and Y cannot be S=O or $SO_2$;

in Iq) $R^3$ is $H_2N—C(=NH)—$, $H_2N—C(=NH)—NH—$ or $Het^2NH$, in which $Het^2$ is a 5- or 6-membered aromatic or saturated heterocyclic radical having 1 or 2 N and/or O atoms, $R^1$, $R^{1'}$ and $R^{1''}$ are H, Ar, $Het^1$Hal, $NR^4$ and/or $CONHR^4_2$, in which $R^4=H$, A and/or $Het^1$, and in which, if $R^1=Ar$, $R^{1'}$ and $R^{1''}$ are each H, and Ar is a phenyl radical which is unsubstituted or monosubstituted or disubstituted by A, OA, OH, Hal or $CF_3$, $R^2$ is A, Ar, $(CH_2)_mXA$, $(CH_2)_mOH$, $(CH_2)_mNH_2$, $(CH_2)_mNHA$, $(CH_2)_mNA_2$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mXCOYA$, $(CH_2)_m XCOY(CH_2)_oAr$, $(CH_2)_mX(CH_2)_oHet^1$, $(CH_2)_mX(CH_2)_oCHHet^1_2$, $(CH_2)_mX(CH_2)_nCHet^1_3$, $(CH_2)_mX(CH_2)_oYA$, $(CH_2)_mX(CH_2)_oNHCOA$, $((CH_2)_mNH-CONH_2$, $(CH_2)_mAr$, $(CH_2)_mCHAr_2$, $(CH_2)_mCAr_3$, $(CH_2)_m Het^1$, $(CH_2)_mCHHet^1_2$, $(CH_2)_mCHet^1_3$, $(CH_2)_mcycloalkyl$, $(CH_2)_m—NH—C(=NH)—NH_2$ or $(CH_2)_m—(HN=)C—NH_2$, in which X and Y, independently of one another, may be S, O, S=O, $SO_2$ or NH, where, if $R^2=(CH_2)_mXCOYA$ or $(CH_2)_mXCOY(CH_2)_o$ Ar, X and Y cannot be S=O or $SO_2$, m is 1, 2, 3 or 4;

in Ir) $R^1$, $R^{1'}$ and $R^{1''}$ are H, Ar, Hal, $NR^4$ and/or $CONHR^4_2$, in which $R^4=H$ and/or A, and in which, if $R^1=Ar$, $R^{1'}$ and $R^{1''}$ are each H, and Ar is a phenyl radical which is unsubstituted or monosubstituted or disubstituted by A, OA, OH, Hal or $CF_3$, $R^3$ is $H_2N—C(=NH)—$, $H_2N—C(=NH)—NH—$ or $Het^2NH$, in which $Het^2$ is a 5- or 6-membered aromatic or saturated heterocyclic radical having 1 or 2 N and/or O atoms, $R^2$ is A, Ar, $(CH_2)_mXA$, $(CH_2)_mOH$, $(CH_2)_mNH_2$, $(CH_2)_mNHA$, $(CH_2)_mNA_2$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mXCOYA$, $(CH_2)_m XCOY(CH_2)_oAr$, $(CH_2)_mX(CH_2)_oHet^1$, $(CH_2)_mX(CH_2)_oCHHet^1_2$, $(CH_2)_mX(CH_2)_oCHet^1_3$ $(CH_2)_mX(CH_2)_oYA$, $(CH_2)_mX(CH_2)_oNHCOA$, $(CH_2)_mNHCONHR^2$, $(CH_2)_mAr$, $(CH_2)_mCHAr_2$, $(CH_2)_mCAr_3$, $(CH_2)_mHet^1$, $(CH_2)_mCHHet^1_2$, $(CH_2)_mCHet^1_3$, $(CH_2)_mcycloalkyl$, $(CH_2)_m—NH—C(=NH)—NH_2$ or $(CH_2)_m—(HN=)C—NH_2$, in which $R^{2'}$ is H, $Het^1$ is imidazolyl, thiophenyl, pyridinyl or indolyl, Ar is phenyl or 4-OH-phenyl, X and Y, independently of one another, may be S, O, S=O, $SO_2$ or NH, where, if $R^2=(CH_2)_mXCOYA$ or $(CH_2)_mXCOY(CH_2)_oAr$, X and Y independently of one another are NH and/or 0, m is 1, 2, 3 or 4, o is 0, 1, 2 or 3;

in Is) $R^3$ is $Het^2NH$, in which $Het^2$ is pyridyl, $R^1$, $R^{1'}$ and $R^{1''}$ are H, Ar and/or Hal, in which, if $R^1=Ar$, $R^{1'}$ and $R^{1''}$ are each H, and Ar is phenyl, $R^2$ is A, Ar, $(CH_2)_mXA$, $(CH_2)_mOH$, $(CH_2)_mNH_2$, $(CH_2)_m$ NHA, $(CH_2)_mNA_2$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mXCOYA$, $(CH_2)_m XCOY(CH_2)_oAr$, $(CH_2)_mX(CH_2)_oHet^1$, $(CH_2)_mX(CH_2)_oCHHet^1_2$, $(CH_2)_mX(CH_2)_oCHet^1_3$, $(CH_2)_mX(CH_2)_oYA$, $(CH_2)_mX(CH_2)_oNHCOA$, $(CH_2)_mNHCONH_2$ $(CH_2)_mAr$, $(CH_2)_mCHAr_2$, $(CH_2)_mCAr_3$, $(CH_2)_mHet^1$, $(CH_2)_mCHHet^1_2$, $(CH_2)_mCHet^1_3$, $(CH_2)_m$ cycloalkyl, $(CH_2)_m—NH—C(=NH)—NH_2$ or $(CH_2)_m—(HN=)C—NH_2$, in which Het$^1$ is imidazolyl, thiophenyl, pyridinyl or indolyl, Ar is phenyl or 4-OH-phenyl, X and Y, independently of one another, may be S, O, S=O, SO$_2$ or NH,
  where, if $R^2$=$(CH_2)_mXCOYA$ or $(CH_2)_mXCOY(CH_2)_oAr$, X and Y independently of one another are NH and/or O,
  and in the case where X and Y are bonded directly to one another by a chemical bond, these are each S, m is 1, 2, 3 or 4, o is 0, 1, 2 or 3;

in It) $R^3$ is Het$^2$NH, in which

Het$^2$ is pyridyl, $R^1$, $R^{1'}$ and $R^{1''}$ are H, Ar and/or Hal, in which Hal is F, Cl and/or Br, and in which, if $R^1$=Ar, $R^{1'}$ and $R^{1''}$ are each H, and Ar is phenyl, $R^2$ is A, $(CH_2)_mXA$, $(CH_2)_mOH$, $(CH_2)_mNH_2$, $(CH_2)_mNHA$, $(CH_2)_mNA_2$, $(CH_2)_mNO_2$, $(CH_2)_mCOOH$, $(CH_2)_m CONH_2$, $(CH_2)_mX(CH_2)_oAr$, $(CH_2)_mX(CH_2)_oCHAr_2$, $(CH_2)_mX(CH_2)_oCAr_3$, $(CH_2)_mNHCOOA$, $(CH_2)_mNHCOO(CH_2)_oAr$, $(CH_2)_mX(CH_2)_oHet^1$, $(CH_2)_mX(CH_2)_oCHHet^1_2$, $(CH_2)_mX(CH_2)_oCHet^1_3$, $(CH_2)_mX(CH_2)_oYA$, $(CH_2)_mX(CH_2)_oNHCOA$, $(CH_2)_mNHCONH_2$ $(CH_2)_mAr$, $(CH_2)_mCHAr_2$, $(CH_2)_mCAr_3$, $(CH_2)_mHet^1$, $(CH_2)_mCHHet^1_2$, $(CH_2)_mCHet^1_3$, $(CH_2)_m$ cycloalkyl, $(CH_2)_m—NH—C(=NH)—NH_2$ or $(CH_2)_m—(HN=)C—NH_2$, $R^{2'}$ is H, $R^2$ and $R^{2'}$ together may alternatively be —$(CH_2)_p$—, Het$^1$ is imidazolyl, thiophenyl, pyridinyl or indolyl, Ar is phenyl or 4-OH-phenyl, X is S, O, S=O, SO$_2$ or NH, Y is S, O or NH, m is 1, 2, 3 or 4, n is 2 or 3, o is 0 or 1, p is 5, where, if
X and Y are bonded directly to one another by a chemical bond, these are each S.

Particular preference is given to the compounds of the general formula I mentioned below:

3-biphenyl-4-yl-3-{2-[4-(pyridin-2-ylamino)pentanoylamino]pentanoylamino}propionic acid,
3-biphenyl-4-yl-3-{2-[4-(pyridin-2-ylamino)butanoylamino]-(2S)-propanoylamino}propionic acid,
3-biphenyl-4-yl-3-{2-[4-(pyridin-2-ylamino)butanoylamino]-(2R)-propanoylamino}propionic acid,
3-biphenyl-4-yl-3-{4-methylsulfanyl-2-[4-(pyridin-2-ylamino)butanoylamino]-(2S)-butanoylamino}propionic acid,
3-biphenyl-4-yl-3-{4-methylsulfanyl-2-[4-(pyridin-2-ylamino)butanoylamino]-(2R)-butanoylamino}propionic acid,
3-biphenyl-4-yl-3-{3-methyl-2-[4-(pyridin-2-ylamino)-(2S)-butanoylamino]-butanoylamino}propionic acid,
3-biphenyl-4-yl-3-{3-methyl-2-[4-(pyridin-2-ylamino)-(2R)-butanoylamino]-butanoylamino}propionic acid,
3-biphenyl-4-yl-3-{4-methyl-2-[4-(pyridin-2-ylamino)butanoylamino]-(2S)-pentanoylamino}propionic acid,
3-biphenyl-4-yl-3-{4-methyl-2-[4-(pyridin-2-ylamino)butanoylamino]-(2R)-pentanoylamino}propionic acid,
N-(1-biphenyl-4-yl-2-carboxyethyl)-3-[4-(pyridin-2-ylamino)butanoylamino]-(2S)-succinamic acid,
N-(1-biphenyl-4-yl-2-carboxyethyl)-3-[4-(pyridin-2-ylamino)butanoylamino]-(2R)-succinamic acid,
3-biphenyl-4-yl-3-{3-cyclohexyl-2-[4-(pyridin-2-ylamino)butanoylamino]-(2R)-propanoylamino}propionic acid,
4-(1-biphenyl-4-yl-2-carboxyethylcarbamoyl)-4-[4-(pyridin-2-ylamino)-butanoylamino]-(4S)-butanoic acid,

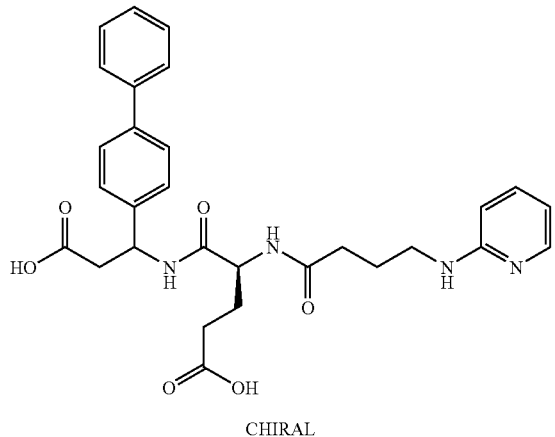

CHIRAL 3-biphenyl-4-yl-3-{3-phenyl-2-[4-(pyridin-2-ylamino)butanoylamino]-(2R)-propanoylamino}propionic acid,
3-biphenyl-4-yl-3-{3-hydroxy-2-[4-(pyridin-2-ylamino)butanoylamino]-(2S)-butanoylamino}propionic acid,
3-biphenyl-4-yl-3-{3-(4-hydroxyphenyl-)$_2$-[4-(pyridin-2-ylamino)butanoylamino]-(2S)-propanoylamino}propionic acid,
3-biphenyl-4-yl-3-{3-phenyl-2-[4-(pyridin-2-ylamino)butanoylamino]-(2S)-propanoylamino}propionic acid,
3-biphenyl-4-yl-3-{2-methyl-2-[4-(pyridin-2-ylamino)butanoylamino]-propanoylamino}propionic acid,
3-biphenyl-4-yl-3-{3-hydroxy-2-[4-(pyridin-2-ylamino)butanoylamino]-(2S)-propanoylamino}propionic acid,
3-biphenyl-4-yl-3-{3-hydroxy-2-[4-(pyridin-2-ylamino)butanoylamino]-(2R)-propanoylamino}propionic acid,
3-biphenyl-4-yl-3-{2-[4-(pyridin-2-ylamino)butanoylamino]-(2S)-hexanoylamino}propionic acid,
3-biphenyl-4-yl-3-{2-[4-(pyridin-2-ylamino)butanoylamino]-(2R)-hexanoylamino}propionic acid,
3-biphenyl-4-yl-3-{2-[4-(pyridin-2-ylamino)butanoylamino]-3-tritylsulfanyl-(2S)-propanoylamino}propionic acid,
3-biphenyl-4-yl-3-{2-[4-(pyridin-2-ylamino)butanoylamino]-3-tritylsulfanyl-(2R)-propanoylamino}propionic acid,
3-biphenyl-4-yl-3-{6-amino-2-[4-(pyridin-2-ylamino)butanoylamino]-(2S)-hexanoylamino}propionic acid,
3-biphenyl-4-yl-3-{6-amino-2-[4-(pyridin-2-ylamino)butanoylamino]-(2R)-hexanoylamino}propionic acid,
3-biphenyl-4-yl-3-{2-[4-(pyridin-2-ylamino)butanoylamino]-(2S)-butanoylamino}propionic acid,
3-biphenyl-4-yl-3-{3-(4-hydroxyphenyl)-2-[4-(pyridin-2-ylamino)butanoylamino]-(2R)-propanoylamino}propionic acid,
3-biphenyl-4-y-3-{5-amino-2-[4-(pyridin-2-ylamino)butanoylamino]-(2R)-pentanoylamino}propionic acid, 3-biphenyl-4-yl-3-{5-guanidino-2-[4-(pyridin-2-ylamino)butanoylamino]-(2R)-pentanoylamino}propionic acid,
3-biphenyl-4-yl-3-{3-1H-imidazol-4-yl-2-[4-(pyridin-2-ylamino)butanoylamino]-(2R)-propionylamino}propionic acid,
3-biphenyl-4-yl-3-{3,3-dimethyl-2-[4-(pyridin-2-ylamino)butanoylamino]-(2R)-butanoylamino}propionic acid,
3-biphenyl-4-yl-3-{2-phenyl-2-[4-(pyridin-2-ylamino)butanoylamino]-(2R)-ethanoylamino}propionic acid,
3-biphenyl-4-yl-3-{3-hydroxy-2-[4-(pyridin-2-ylamino)butanoylamino]-(2R)-butanoylamino}propionic acid,
3-biphenyl-4-yl-3-{4-carboxy-2-[4-(pyridin-2-ylamino)butanoylamino]-(2R)-butanoylamino}propionic acid,
3-biphenyl-4-yl-3-{4-carbamoyl-2-[4-(pyridin-2-ylamino)butanoylamino]-(2S)-butanoylamino}propionic acid,
3-biphenyl-4-yl-3-{4-hydroxy-2-[4-(pyridin-2-ylamino)butanoylamino]-(2S)-butanoylamino}propionic acid,
3-biphenyl-4-yl-3-{1-[1-(4-pyridin-2-ylaminobutanoylamino)cyclohexyl]-methanoylamino}propionic acid,
3-biphenyl-4-yl-3-{-2-[4-(pyridin-2-ylamino)butanoylamino]-(2S)-pentanoylamino}propionic acid,
3-biphenyl-4-yl-3-{-2-[4-(pyridin-2-ylamino)butanoylamino]-(2R)-pentanoylamino}propionic acid,
3-biphenyl-4-yl-3-{5-amino-2-[(4-(pyridin-2-ylamino)butanoylamino]-(2S)-pentanoylamino}propionic acid,
3-biphenyl-4-yl-3-{-2-[4-(pyridin-2-ylamino)butanoylamino]-3-thiophen-2-yl-(2S)-propanoylamino}propionic acid,
3-biphenyl-4-yl-3-{-3-pyridin-4-yl-2-[4-(pyridin-2-ylamino)butanoylamino]-(2S)-propanoylamino}propionic acid,
3-biphenyl-4-yl-3-{-3-pyridin-4-yl-2-[4-(pyridin-2-ylamino)butanoylamino]-(2R)-propanoylamino}propionic acid,
3-biphenyl-4-yl-3-{-3-indol-2-yl-2-[4-(pyridin-2-ylamino)butanoylamino]-propanoylamino}propionic acid,
3-biphenyl-4-yl-3-{3-1H-imidazol-4-yl-2-[4-(pyridin-2-ylamino)butanoylamino]-(2S)-propionylamino}propionic acid,
3-biphenyl-4-yl-3-{3,3-dimethyl-2-[4-(pyridin-2-ylamino)butanoylamino]-(2S)-butanoylamino}propionic acid,
3-biphenyl-4-yl-3-{3-cyclohexyl-2-[4-(pyridin-2-ylamino)butanoylamino]-(2S)-propanoylamino}propionic acid,
3-biphenyl-4-yl-3-{5-guanidino-2-[4-(pyridin-2-ylamino)butanoylamino]-(2S)-pentanoylamino}propionic acid,
3-biphenyl-4-yl-3-{-3-indol-2-yl-2-[4-(pyridin-2-ylamino)butanoylamino]-(2S)propanoylamino}propionic acid,
3-biphenyl-4-yl-3-{4-carbamoyl-2-[5-(pyridin-2-ylamino)pentanoylamino]-(2S)-butanoylamino}propionic acid,
3-biphenyl-4-yl-3-{4-hydroxy-2-[5-(pyridin-2-ylamino)pentanoylamino]-(2S)-butanoylamino}propionic acid,
3-biphenyl-4-yl-3-{1-[1-(5-pyridin-2-ylaminopentanoylamino)cyclohexyl]-methanoylamino}propionic acid,
3-biphenyl-4-yl-3-{-2-[5-(pyridin-2-ylamino)pentanoylamino]-(2S)-pentanoylamino}propionic acid,
3-biphenyl-4-yl-3-{-2-[5-(pyridin-2-ylamino)pentanoylamino]-(2R)-pentanoylamino}propionic acid,
3-biphenyl-4-yl-3-{5-amino-2-[5-(pyridin-2-ylamino)pentanoylamino]-(2R)-pentanoylamino}propionic acid,
3-biphenyl-4-yl-3-{-2-[(5-(pyridin-2-ylamino)pentanoylamino]-3-thiophen-2-yl-(2S)-propanoylamino}propionic acid,
3-biphenyl-4-yl-3-{-3-pyridin-4-yl-2-[5-(pyridin-2-ylamino)pentanoylamino]-(2S)-propanoylamino}propionic acid,
3-biphenyl-4-yl-3-{-3-pyridin-4-yl-2-[5-(pyridin-2-ylamino)pentanoylamino]-(2R)-propanoylamino}propionic acid,
3-biphenyl-4-yl-3-{-3-indol-2-yl-2-[5-(pyridin-2-ylamino)pentanoylamino]-(2R)-propanoylamino}propionic acid,
3-biphenyl-4-yl-3-{3-1H-imidazol-4-yl-2-[5-(pyridin-2-ylamino)pentanoylamino]-(2S)-propionylamino}propionic acid,
3-biphenyl-4-yl-3-{3-1H-imidazol-4-yl-2-[5-(pyridin-2-ylamino)pentanoylamino]-(2R)-propionylamino}propionic acid,
3-biphenyl-4-yl-3-{3,3-dimethyl-2-[5-(pyridin-2-ylamino)pentanoylamino]-(2S)-butanoylamino}propionic acid,
3-biphenyl-4-yl-3-{3-cyclohexyl-2-[5-(pyridin-2-ylamino)pentanoylamino]-(2S)-propanoylamino}propionic acid,
3-biphenyl-4-yl-3-{5-guanidino-2-[5-(pyridin-2-ylamino)pentanoylamino]-(2S)-pentanoylamino}propionic acid,
3-biphenyl-4-yl-3-{5-guanidino-2-[5-(pyridin-2-ylamino)pentanoylamino]-(2R)-pentanoylamino}propionic acid,
3-biphenyl-4-yl-3-{-3-indol-2-yl-2-[5-(pyridin-2-ylamino)pentanoylamino]-(2S)-propanoylamino}propionic acid,
3-biphenyl-4-yl-3-{3-hydroxy-2-[5-(pyridin-2-ylamino)pentanoylamino]-(2R)-propanoylamino}propionic acid,
3-biphenyl-4-yl-3-{2-[5-(pyridin-2-ylamino)pentanoylamino]-(2S)-hexanoylamino}propionic acid,
3-biphenyl-4-yl-3-{2-[5-(pyridin-2-ylamino)pentanoylamino]-(2R)-hexanoylamino}propionic acid,
3-biphenyl-4-yl-3-{2-[5-(pyridin-2-ylamino)pentanoylamino]-3-tritylsulfanyl-(2S)-propanoylamino}propionic acid,
3-biphenyl-4-yl-3-{2-[5-(pyridin-2-ylamino)pentanoylamino]-3-tritylsulfanyl-(2R)-propanoylamino}propionic acid,
3-biphenyl-4-yl-3-{6-amino-2-[5-(pyridin-2-ylamino)pentanoylamino]-(2R)-hexanoylamino}propionic acid,
3-biphenyl-4-yl-3-{3-(4-hydroxyphenyl)-2-[5-(pyridin-2-ylamino)pentanoylamino]-(2S)-propanoylamino}propionic acid,
3-biphenyl-4-yl-3-{5-amino-2-[5-(pyridin-2-ylamino)pentanoylamino]-(2S)-pentanoylamino}propionic acid,
3-biphenyl-4-yl-3-{3,3-dimethyl-2-[5-(pyridin-2-ylamino)pentanoylamino]-(2R)-butanoylamino}propionic acid,
3-biphenyl-4-yl-3-{2-phenyl-2-[5-(pyridin-2-ylamino)pentanoylamino]-(2R)-ethanoylamino}propionic acid,
3-biphenyl-4-yl-3-{3-hydroxy-2-[5-(pyridin-2-ylamino)pentanoylamino]-(2R)-butanoylamino}propionic acid,
3-biphenyl-4-yl-3-{4-carboxy-2-[5-(pyridin-2-ylamino)pentanoylamino]-(2R)-butanoylamino}propionic acid,
3-biphenyl-4-yl-3-{2-[5-(pyridin-2-ylamino)pentanoylamino]-(2S)-propanoylamino}propionic acid,
3-biphenyl-4-yl-3-{2-[5-(pyridin-2-ylamino)pentanoylamino]-(2R)-propanoylamino}propionic acid,
3-biphenyl-4-yl-3-{4-methylsulfanyl-2-[5-(pyridin-2-ylamino)pentanoylamino]-(2S)-butanoylamino}propionic acid,
3-biphenyl-4-yl-3-{4-methylsulfanyl-2-[5-(pyridin-2-ylamino)pentanoylamino]-(2R)-butanoylamino}propionic acid,
3-biphenyl-4-yl-3-{3-methyl-2-[5-(pyridin-2-ylamino)pentanoylamino]-(2S)-butanoylamino}propionic acid,
3-biphenyl-4-yl-3-{3-methyl-2-[5-(pyridin-2-ylamino)pentanoylamino]-(2R)-butanoylamino}propionic acid,
3-biphenyl-4-yl-3-{4-methyl-2-[5-(pyridin-2-ylamino)pentanoylamino]-(2S)-pentanoylamino}propionic acid,
3-biphenyl-4-yl-3-{4-methyl-2-[5-(pyridin-2-ylamino)pentanoylamino]-(2R)-pentanoylamino}propionic acid, 3-biphenyl-4-yl-3-{3-carboxy-2-[5-(pyridin-2-ylamino)pentanoylamino]-(2S)-propanoylamino}propionic acid,
3-biphenyl-4-yl-3-{3-carboxy-2-[5-(pyridin-2-ylamino)pentanoylamino]-(2R)-propanoylamino}propionic acid,
3-biphenyl-4-yl-3-{3-cyclohexyl-2-[5-(pyridin-2-ylamino)pentanoylamino]-(2R)-propanoylamino}propionic acid,
3-biphenyl-4-yl-3-{4-carboxy-2-[5-(pyridin-2-ylamino)pentanoylamino]-(2S)-butanoylamino}propionic acid,
3-biphenyl-4-yl-3-{3-phenyl-2-[5-(pyridin-2-ylamino)pentanoylamino]-(2S)-propanoylamino}propionic acid,
3-biphenyl-4-yl-3-{3-phenyl-2-[5-(pyridin-2-ylamino)pentanoylamino]-(2R)-propanoylamino}propionic acid,
3-biphenyl-4-yl-3-{3-hydroxy-2-[5-(pyridin-2-ylamino)pentanoylamino]-(2S)-butanoylamino}propionic acid,
3-biphenyl-4-yl-3-{4-hydroxyphenyl-2-[5-(pyridin-2-ylamino)pentanoylamino]-(2R)-propanoylamino}propionic acid,
3-biphenyl-4-yl-3-{2-[5-(pyridin-2-ylamino)pentanoylamino]-(2S)-butanoylamino}propionic acid,
3-biphenyl-4-yl-3-{2-methyl-2-[5-(pyridin-2-ylamino)pentanoylamino]-propanoylamino}propionic acid,
3-biphenyl-4-yl-3-{3-hydroxy-2-[5-(pyridin-2-ylamino)pentanoylamino]-(2S)-propanoylamino}propionic acid,
3-biphenyl-4-yl-3-{2-phenyl-2-[5-(pyridin-2-ylamino)pentanoylamino]-(2S)-ethanoylamino}propionic acid,
3-biphenyl-4-yl-3-{3-thiophen-2-[5-(pyridin-2-ylamino)pentanoylamino]-(2R)-propanoylamino}propionic acid,
3-biphenyl-4-yl-3-{4-carbamoyl-2-[5-(pyridin-2-ylamino)pentanoylamino]-(2R)-butanoylamino}propionic acid,
3-biphenyl-4-yl-3-{2-phenyl-2-[4-(pyridin-2-ylamino)butanoylamino]-(2S)-ethanoylamino}propionic acid,
3-biphenyl-4-yl-3-{3-thiophen-2-[4-(pyridin-2-ylamino)butanoylamino]-(2R)-propanoylamino}propionic acid,
3-biphenyl-4-yl-3-{4-carbamoyl-2-[4-(pyridin-2-ylamino)butanoylamino]-(2R)butanoylamino}propionic acid,
3-biphenyl-4-yl-3-{6-amino-2-[5-(pyridin-2-ylamino)pentanoylamino]-(2S)-hexanoylamino}propionic acid,
3-biphenyl-4-yl-3-{3-tert-butylsulfanyl-2-[5-(pyridin-2-ylamino)pentanoylamino]-(2S)-propanoylamino}propionic acid,
3-biphenyl-4-yl-3-{3-tert-butyldisulfanyl-2-[5-(pyridin-2-ylamino)pentanoylamino]-(2S)-propanoylamino}propionic acid,
3-biphenyl-4-yl-3-{3-(benzylsulfanyl)-2-[5-(pyridin-2-ylamino)pentanoylamino]-(2S)-propanoylamino}propionic acid,
3-biphenyl-4-yl-3-{3-(acetylaminomethylsulfanyl)-2-[5-(pyridin-2-ylamino)pentanoylamino]-(2S)-propanoylamino}propionic acid,
3-biphenyl-4-yl-3-{3-(diphenylmethylsulfanyl)-2-[5-(pyridin-2-ylamino)pentanoylamino]-(2S)-propanoylamino}propionic acid,
3-biphenyl-4-yl-3-{3-(methylsulfanyl)-2-[5-(pyridin-2-ylamino)pentanoylamino]-(2S)-propanoylamino}propionic acid,
3-biphenyl-4-yl-3-{4-trityl-2-[5-(pyridin-2-ylamino)pentanoylamino]-(2S)-butanoylamino}propionic acid,
3-biphenyl-4-yl-3-{6-trityl-2-[5-(pyridin-2-ylamino)pentanoylamino]-(2S)-hexanoylamino}propionic acid,
3-biphenyl-4-yl-3-{3-(ethylsulfanyl)-2-[5-(pyridin-2-ylamino)pentanoylamino]-(2S)-propanoylamino}propionic acid,
3-biphenyl-4-yl-3-{4-hydroxy-2-[5-(pyridin-2-ylamino)pentanoylamino]-(2R)-butanoylamino}propionic acid,
3-biphenyl-4-yl-3-{4-hydroxy-2-[4-(pyridin-2-ylamino)butanoylamino]-(2R)-butanoylamino}propionic acid,
3-biphenyl-4-yl-3-{2-[4-(pyridin-2-ylamino)butanoylamino]-4-tritylsulfanyl-(2S)-butanoylamino}propionic acid,
3-biphenyl-4-yl-3-{4-methoxy-2-[4-(pyridin-2-ylamino)butanoylamino]-(2S)-butanoylamino}propionic acid,
3-biphenyl-4-yl-3-{4-methanesulfinyl-2-[4-(pyridin-2-ylamino)butanoylamino]-(2S)-butanoylamino}propionic acid,
3-biphenyl-4-yl-3-{4-methanesulfonyl-2-[4-(pyridin-2-ylamino)butanoylamino]-(2S)-butanoylamino}propionic acid,
3-biphenyl-4-yl-3-{3-benzyloxy-2-[4-(pyridin-2-ylamino)butanoylamino]-(2S)-propanoylamino}propionic acid,
3-biphenyl-4-yl-3-{6-ureido-2-[4-(pyridin-2-ylamino)butanoylamino]-(2S)-hexanoylamino}propionic acid,
3-biphenyl-4-yl-3-{6-benzyloxycarbonylamino-2-[4-(pyridin-2-ylamino)butanoylamino]-(2S)-hexanoylamino}propionic acid,
3-biphenyl-4-yl-3-{6-acetylamino-2-[4-(pyridin-2-ylamino)butanoylamino]-(2S)-hexanoylamino}propionic acid,
3-biphenyl-4-yl-3-{6-allyloxycarbonylamino-2-[4-(pyridin-2-ylamino)butanoylamino]-(2S)-hexanoylamino}propionic acid,
3-biphenyl-4-yl-3-{4-tritylsulfanyl-2-[5-(pyridin-2-ylamino)pentanoylamino]-(2S)-butanoylamino}propionic acid,
3-biphenyl-4-y-3-{4-methoxy-2-[5-(pyridin-2-ylamino)pentanoylamino]-(2S)-butanoylamino}propionic acid,
3-biphenyl-4-yl-3-{4-methanesulfinyl-2-[5-(pyridin-2-ylamino)pentanoylamino]-(2S)-butanoylamino}propionic acid,
3-biphenyl-4-yl-3-{4-methanesulfonyl-2-[5-(pyridin-2-ylamino)pentanoylamino]-(2S)-butanoylamino}propionic acid,
3-biphenyl-4-yl-3-{3-benzyloxy-2-[5-(pyridin-2-ylamino)pentanoylamino]-(2S)-propanoylamino}propionic acid,
3-biphenyl-4-yl-3-{6-ureido-2-[5-(pyridin-2-ylamino)pentanoylamino]-(2S)-hexanoylamino}propionic acid,
3-biphenyl-4-yl-3-{6-benzyloxycarbonylamino-2-[5-(pyridin-2-ylamino)pentanoylamino]-(2S)-hexanoylamino}propionic acid,
3-biphenyl-4-yl-3-{6-acetylamino-2-[5-(pyridin-2-ylamino)pentanoylamino]-(2S)-hexanoylamino}propionic acid,
3-biphenyl-4-yl-3-{6-allyloxycarbonylamino-2-[5-(pyridin-2-ylamino)pentanoylamino]-(2S)-hexanoylamino}propionic acid,
3-biphenyl-4-yl-3-{4-tritylsulfanyl-2-[6-(pyridin-2-ylamino)hexanoylamino]-(2S)-butanoylamino}propionic acid,
3-biphenyl-4-yl-3-{4-methoxy-2-[6-(pyridin-2-ylamino)hexanoylamino]-(2S)-butanoylamino}propionic acid,
3-biphenyl-4-yl-3-{4-methanesulfinyl-2-[6-(pyridin-2-ylamino)hexanoylamino]-(2S)-butanoylamino}propionic acid,
3-biphenyl-4-yl-3-{4-methanesulfonyl-2-[6-(pyridin-2-ylamino)hexanoylamino]-(2S)-butanoylamino}propionic acid,
3-biphenyl-4-yl-3-{3-benzyloxy-2-[6-(pyridin-2-ylamino)hexanoylamino]-(2S)-propanoylamino}propionic acid,
3-biphenyl-4-yl-3-{6-ureido-2-[6-(pyridin-2-ylamino)hexanoylamino]-(2S)-hexanoylamino}propionic acid,
3-biphenyl-4-yl-3-{6-benzyloxycarbonylamino-2-[6-(pyridin-2-ylamino)-hexanoylamino]-(2S)-hexanoylamino}propionic acid,
3-biphenyl-4-yl-3-{6-acetylamino-2-[6-(pyridin-2-ylamino)hexanoylamino]-(2S)-hexanoylamino}propionic acid, 3-{3-benzyloxy-2-[5-(pyridin-2-ylamino)pentanoylamino]
propionylamino}-3-(3-chlorophenyl)propionic acid,
3-{3-benzyloxy-2-[5-(pyridin-2-ylamino)pentanoylamino]
propionylamino}-3-(3-bromophenyl)propionic acid,
3-{3-benzyloxy-2-[5-(pyridin-2-ylamino)pentanoylamino]
propionylamino}-3-(4-chlorophenyl)propionic acid, and their stereoisomers and their physiologically acceptable salts and solvates.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for said reactions. Use can also be made here of variants which are known per se, but are not mentioned here in greater detail.

If desired, the starting materials can also be formed in situ, so that they are not isolated from the reaction mixture, but are instead immediately converted further into the compounds of the formula I.

It is also possible for a plurality of—identical or different—protected amino and/or hydroxyl groups to be present in the molecule of the starting material. If the protecting groups present differ from one another, they can in many cases be removed selectively (cf. in this respect: T. W. Greene, P. G. M. Wuts, *Protective Groups in Organic Chemistry*, 2nd Edn., Wiley, New York 1991 or P. J. Kocienski, *Protecting Groups*, 1st Edn., Georg Thieme Verlag, Stuttgart-New-York, 1994).

The term "amino protecting group" is generally known and relates to groups which are suitable for protecting (blocking) an amino group against chemical reactions. Typical of such groups are, in particular, unsubstituted or substituted acyl, aryl, aralkoxymethyl or aralkyl groups. Since the amino protecting groups are removed after the desired reaction (or synthesis sequence), their type and size is furthermore not crucial; however, preference is given to those having 1-20, in particular 1-8 carbon atoms. The term "acyl group" is to be understood in the broadest sense in connection with the present process. It includes acyl groups derived aliphatic, araliphatic, alicyclic, aromatic and heterocyclic carboxylic acids or sulfonic acids, as well as, in particular, alkoxycarbonyl, alkenyloxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as phenoxyacetyl; alkoxycarbonyl, such as methoxycarbonyl, ethoxycarbonyl, 2,2,2-trichloroethoxycarbonyl, BOC and 2-iodoethoxycarbonyl; alkenyloxycarbonyl, such as allyloxycarbonyl (Aloc), aralkoxycarbonyl, such as CBZ (synonymous with Z), 4-methoxybenzyloxycarbonyl (MOZ), 4-nitrobenzyloxycarbonyl and 9-fluorenylmethoxycarbonyl (Fmoc); 2-(phenylsulfonyl)-ethoxycarbonyl; trimethylsilylethoxycarbonyl (Teoc), and arylsulfonyl, such as 4-methoxy-2,3,6-trimethylphenylsulfonyl (Mtr). Preferred amino protecting groups are BOC, Fmoc and Aloc, furthermore CBZ, benzyl and acetyl.

Particularly preferred protecting groups are BOC and Fmoc. The term "hydroxyl protecting group" is likewise generally known and relates to groups which are suitable for protecting a hydroxyl group against chemical reactions. Typical of such groups are the above-mentioned unsubstituted or substituted aryl, aralkyl, aroyl or acyl groups, furthermore also alkyl groups, alkyl-, aryl- and aralkylsilyl groups, and O,O- and O,S-acetals. The nature and size of the hydroxyl protecting groups is not crucial since they are removed again after the desired chemical reaction or synthesis sequence; preference is given to groups having 1-20 carbon atoms, in particular 1-10 carbon atoms. Examples of hydroxyl protecting groups are, inter alia, aralkyl groups, such as benzyl, 4-methoxybenzyl and 2,4-dimethoxybenzyl, aroyl groups, such as benzoyl and p-nitrobenzoyl, acyl groups, such as acetyl and pivaloyl, p-toluenesulfonyl, alkyl groups, such as methyl and tert-butyl, but also allyl, alkylsilyl groups, such as trimethylsilyl (TMS), triisopropylsilyl (TIPS), tert-butyidimethylsilyl (TBS) and triethylsilyl, trimethylsilylethyl, aralkylsilyl groups, such as tert-butyldiphenylsilyl (TBDPS), cyclic acetals, such as isopropylidene acetal, cyclopentylidene acetal, cyclohexylidene acetal, benzylidene acetal, p-methoxybenzylidene acetal and o,p-dimethoxybenzylidene acetal, acyclic acetals, such as tetrahydropyranyl (Thp), methoxymethyl (MOM), methoxyethoxymethyl (MEM), benzyloxymethyl (BOM) and methylthiomethyl (MTM). Particularly preferred hydroxyl protecting groups are benzyl, acetyl, tert-butyl and TBS.

The liberation of the compounds of the formula I from their functional derivatives is known from the literature for the protecting group used in each case (for example T. W. Greene, P. G. M. Wuts, *Protective Groups in Organic Chemistry*, 2nd Edn., Wiley, New York 1991 or P. J. Kocienski, *Protecting Groups*, 1st Edn., Georg Thieme Verlag, Stuttgart-New York, 1994). Use may also be made here of variants which are known per se, but are not mentioned here in greater detail.

The groups BOC and O-tert-butyl may, for example, be removed preferentially using TFA in dichloromethane or using approximately 3 to 5N HCl in dioxane at 15-30° C., and the Fmoc group using an approximately 5 to 50% solution of dimethylamine, diethylamine or piperidine in DMF at 15-30° C. The Aloc group can be removed under gentle conditions with noble-metal catalysis in chloroform at 20-30° C. A preferred catalyst is tetrakis(triphenylphosphine)palladium(0).

The starting compounds of the formulae II to VI and 1 to 3 are generally known. If they are novel, however, they can be prepared by methods known per se.

The compounds of the formula I can also be synthesised on a solid phase, the binding to the solid phase taking place via the OH of the carboxyl group. In the case of synthesis on a solid phase, the carboxyl group is substituted by OPol, where Pol is a solid phase without a terminal functional group. Pol represents the polymeric support material and all atoms of the anchor group of a solid phase apart from the terminal functional group. The anchor groups of a solid phase, also known as linkers, are necessary for binding of the compound to be functionalised to the solid phase. A review of syntheses on the solid phase and the solid phases and/or linkers which can be employed for this purpose is given, for example, in Novabiochem—The Combinatorial Chemistry Catalog, March 99, pages S1-S72.

Particularly suitable solid phases for the synthesis of compounds according to the invention are solid phases having a hydroxyl group as terminal functionality, for example Wang resin or polystyrene A OH.

Compounds of the formula II with $R^1$=Ar and R=OL, where L is Pol, are prepared, for example, in accordance with the following reaction scheme 1, where $SG_1$ denotes an amino-protecting group, as described above.

Reaction scheme 1:

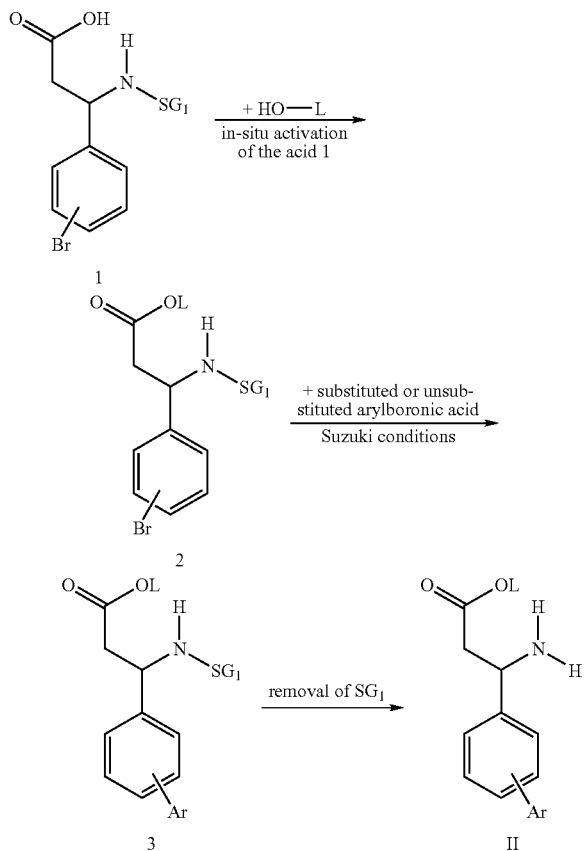

The bromophenyl-substituted carboxylic acid 1 is activated in situ by known methods, for example by reaction with diisopropylcarbodiimide, and reacted with the alcohol HO-L, where L is as defined above. The subsequent coupling of compound 2 to an unsubstituted or substituted arylboronic acid under Suzuki conditions generates the derivative 3. The removal of the protecting group $SG_1$ under known conditions liberates a compound of the formula II.

The Suzuki reaction is advantageously carried out with palladium control, preferably by addition of $Pd(PPh_3)_4$, in the presence of a base, such as potassium carbonate, in an inert solvent or solvent mixture, for example DMF, at temperatures between 0° and 150°, preferably between 60° and 120°. The reaction time, depending on the conditions used, is between a few minutes and several days. The boronic acid derivatives can be prepared by conventional methods or are commercially available. The reactions can be carried out analogously to the methods indicated in Suzuki et al., J. Am. Chem. Soc. 1989, 111, 314 ff. and in Suzuki et al. Chem. Rev. 1995, 95, 2457 ff.

Compounds of the formula I are obtained by peptide-analogous coupling of the compounds of the formula II with a compound of the formula III or by peptide-analogous coupling of the compounds of the formula IV with a compound of the formula V under standard conditions.

Compounds of the formula III are obtained by peptide-analogous coupling of the compounds of the formula V with an amino compound $H_2N-C(R^2,R^{2'})-COOSG^2$ under standard conditions, where $SG^2$ denotes a hydroxyl-protecting group, as described above, which is removed after the coupling. Compounds of the formula IV are obtained by peptide-analogous coupling of a compound of the formula II with a carboxyl compound $HOOC-C(R^2,R^{2'})-NHSG_1$ under standard conditions, where $SG_1$ is an amino-protecting group as described above which is cleaved off after the coupling. Conventional methods of peptide synthesis are described, for example, in Houben-Weyl, l.c., Volume 15/11, 1974, pages 1 to 806.

The coupling reaction preferably succeeds in the presence of a dehydrating agent, for example a carbodiimide, such as dicyclohexylcarbodiimide (DCC), N-(3-dimethylaminopropyl)-N'-ethylcarbodiimide hydrochloride (EDC) or diisopropylcarbodiimide (DIC), furthermore, for example, propanephosphonic anhydride (cf. Angew. Chem. 1980, 92, 129), diphenylphosphoryl azide or 2-ethoxy-N-ethoxycarbonyl-1,2-dihydroquinoline, in an inert solvent, for example a halogenated hydrocarbon, such as dichloromethane, an ether, such as tetrahydrofuran or dioxane, an amide, such as DMF or dimethylacetamide, a nitrile, such as acetonitrile, in dimethyl sulfoxide or in the presence of this solvent, at temperatures between about −10 and 40°, preferably between 0 and 30°. The reaction time, depending on the conditions used, is between a few minutes and several days.

It has proven particularly advantageous to add the coupling reagent TBTU (O-(benzotriazol-1-yl)-N,N,N',N'-tetramethyluronium tetrafluoroborate) or O-(benzotriazol-1-yl)-N,N,N',N'-tetramethyluronium hexafluorophosphate, since in the presence of one of these compounds only slight racemisation occurs and no cytotoxic by-products are formed.

Instead of compounds of the formula II, V and/or VI, it is also possible to employ derivatives of compounds of the formula III, V and/or VI, preferably a pre-activated carboxylic acid, or a carboxylic acid halide, a symmetrical or mixed anhydride or an active ester. Radicals of this type for activation of the carboxyl group in typical acylation reactions have been described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example by addition of HOBt (1-hydroxybenzotriazole) or N-hydroxysuccinimide.

The reaction is generally carried out in an inert solvent; if a carboxylic acid halide is used, it is carried out in the presence of an acid-binding agent, preferably an organic base, such as triethylamine, dimethylaniline, pyridine or quinoline.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, para-chlorophenoxyisobutyric acid, cyclohexanecarboxylic acid, glucose 1-phosphate, naphthalenemono- and -disulfonic acids or lauryl-sulfuric acid. Salts with physiologically unacceptable acids, for example picrates, can be used to isolate and/or purify the compounds of the formula I.

On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate).

The invention also relates to the compounds of the formula I, their stereoisomers and their physiologically acceptable salts or solvates as medicament active ingredients.

The invention furthermore relates to compounds of the formula I, their stereoisomers and their physiologically acceptable salts or solvates as integrin inhibitors.

The invention also relates to the compounds of the formula I, their stereoisomers and their physiologically acceptable salts or solvates for use in combating illnesses.

The invention likewise relates to the use of compounds of the formula I their stereoisomers and their physiologically acceptable salts or solvates for the preparation of a medicament.

The invention furthermore relates to pharmaceutical preparations comprising at least one compound of the formula I, their stereoisomers and/or a physiologically acceptable salt or solvate thereof prepared, in particular, by non-chemical methods. The compounds of the formula I can be brought into a suitable dosage form here together with at least one solid, liquid and/or semiliquid excipient or assistant and, if desired, in combination with one or more further active ingredients.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or vaseline. Suitable for oral administration are, in particular, tablets, pills, coated tablets, capsules, powders, granules, syrups, juices or drops, suitable for rectal administration are suppositories, suitable for parenteral administration are solutions, preferably oily or aqueous solutions, furthermore suspensions, emulsions or implants, and suitable for topical application are ointments, creams or powders. The novel compounds can also be lyophilised and the resultant lyophilisates used, for example, for the preparation of injection preparations. The preparations indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active ingredients, for example one or more vitamins.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronised form, in which case one or more additional physiologically acceptable solvents may be present, for example ethanol. Inhalation solutions can be administered with the aid of conventional inhalers.

The compounds of the formula I, their stereoisomers and/or their physiologically acceptable salts or solvates can be employed as medicament active ingredients in human and veterinary medicine, in particular for the prophylaxis and/or therapy of circulation disorders, pulmonary fibrosis, pulmonary embolism, thrombosis, in particular deep-vein thrombosis, cardiac infarction, arteriosclerosis, aneurysma dissecans, transient ischaemic attacks, apoplexia, angina pectoris, in particular unstable angina pectoris, pathological connecting tissue proliferation in organs or fibrosis, particular pulmonary fibrosis, but also cystic fibrosis, dermatofibrosis, hepatic fibrosis, liver cirrhosis, urethrofibrosis, renal fibrosis, cardiac fibrosis, infantile endocardial fibrosis, pancreatic fibrosis, disturbed hornification of the skin, in particular leukoplakia, lichen planus and squamous cell carcinoma, tumour illnesses, such as tumour development, tumour angiogenesis or tumour metastasis, of solid tumours and those of the blood or immune system, for example tumours of the skin, squamous cell carcinoma, tumours of the blood vessels, of the gastro-intestinal tract, of the lung, of the breast, of the liver, of the kidney, of the spleen, of the pancreas, of the brain, of the testes, of the ovary, of the womb, of the vagina, of the muscles, of the bones, and those of the throat and head area, osteolytic illnesses, such as osteoporosis, hyperparathyroidism, Paget's disease, malign hypercalcaemia, incompatible blood transfusion, pathologically angiogenic disorders, such as, for example, inflammation, ophthalmological disorders, diabetic retinopathy, macular degeneration, myopia, corneal transplant, ocular histoplasmosis, rheumatic arthritis, osteoarthritis, rubeotic glaucoma, ulcerative colitis, Crohn's disease, atherosclerosis, psoriasis, restenosis, in particular after angioplasty, multiple sclerosis, pregnancy, absumptio placentaris, viral infection, bacterial infection, fungal infection, foot and mouth disease (FMD), HIV, anthrax, candida albicans, in the case of parasitic infestation, in the case of acute kidney failure and in the case of wound healing for supporting the healing process.

In the case of viral infection, the compounds according to the invention act, in particular, by inhibiting or breaking viral bonds between cell-mediated integrin-binding proteins and the viral shell or indirectly by preventing the uptake of the viruses, which are bound to extracellular matrix constituents, which have been recognised as integrins, or by breaking integrin-promoted mechanisms which are associated with the viral infection (J Virol 2000 June; 74(11):4949-56, J Virol 2000 August; 74(16):7298-306, J Virol 2001 May; 75(9): 4158-64, Virology. 2001 Sep. 30;288(2):192-202. (FMDV), Virus Res. 2001 July; 76(1):1-8 (echovirus), J Biol Chem. 2001 Jul. 13;276(28):26204-10. (HIV), Biochem Biophys Res Commun. 2001 May 11;283(3):668-73 (papillomavirus), Proc Natl Acad Sci USA. 2000 Dec. 19;97(26):14644-9 (rotavirus)).

In the case of bacterial infection, the action takes place, in particular, by inhibition of the binding and/or the uptake of the bacteria or bacterial toxins or of the toxic products induced by bacterial infections to or by cells via integrin-promoted mechanisms (Nature 2001: Nov 8: 225-229 (anthrax), J Exp Med. 2001 May 7;193(9):103544 (pertussis), Proc Natl Acad Sci USA. 2000 Feb. 29;97(5):2235-40 (group A streptococcus), Infect Immun. 2000 January; 68(1):72-9 (Pasteurella haemolytica leucotoxin), J Biol Chem. 1997 Nov. 28;272(48):30463-9. (RTX leucotoxins)).

In the case of parasitic infestation, the action takes place, in particular, by inhibition of the binding and/or uptake of the parasitic or parasite-derived or induced toxins to or by the cells via integrin-directed mechanisms (Infect Immun. 1999 September; 67(9):4477-84.(leishmania)).

The substances according to the invention are generally preferably administered in doses of from about 0.05 to 500 mg, in particular from 0.5 to 100 mg, per dosage unit. The daily dose is preferably from about 0.01 to 2 mg/kg of body weight. However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular illness to which the therapy applies. Parenteral administration is preferred.

Furthermore, the compounds of the formula I can be used as integrin ligands for the production of columns for affinity chromatography for the purification of integrins.

In this method, the ligand, i.e. a compound of the formula I, is covalently coupled to a polymeric support via an anchor function, for example the carboxyl group.

Suitable polymeric support materials are the polymeric solid phases having preferably hydrophilic properties that are known in peptide chemistry, for example crosslinked polysugars, such as cellulose, sepharose or Sephadex®, acrylamides, polyethylene glycol- or polystyrene-based polymers or Tentakel® polymers.

The materials for affinity chromatography for integrin purification are prepared under conditions as are usual and known per se for the condensation of amino acids.

The compounds of the formula I have one or more centres of chirality and can therefore exist in racemic or optically active form. Racemates obtained can be resolved into the enantiomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid, and the various optically active camphorsulfonic acids, such as β-camphorsulfonic acid. Resolution of the enantiomers with the aid of a column filled with an optically active resolving agent (for example dinitrobenzoylphenylglycine) is also advantageous; an example of a suitable eluent is a mixture of hexane/isopropanol/acetonitrile, for example in the volume ratio 82:15:3.

It is of course also possible to obtain optically active compounds of the formula I by the methods described above by using starting materials which are already optically active.

Above and below, all temperatures are given in ° C. In the following examples, "conventional work-up" means that, if necessary, water is added, if necessary, depending on the constitution of the end product, the pH is adjusted to a value between 2 and 10, the mixture is extracted with ethyl acetate or dichloromethane, the phases are separated, the organic phase is dried over sodium sulfate and evaporated, and the product is purified by chromatography on silica gel, by preparative HPLC and/or by crystallisation. The purified compounds are, if desired, freeze-dried.

The eluents used are gradients of acetonitrile (B) with 0.08% of TFA (trifluoroacetic acid) and water (A) with 0.1% of TFA. The gradient is indicated in percent by volume of acetonitrile.

The HPLC analyses (retention time RT) were carried out in the following systems:

3 μm Silica-Rod column with a 210 second gradient from 20 to 100% water/acetonitrile/0.01% trifluoroacetic acid, at a flow rate of 2.2 ml/min and with detection at 220 nm, or Chromolith RP18e 100-4,6 column with a 30 min gradient from 1 to 75% 0.014 M $NaH_2PO_4$/isopropanol, at a flow rate of 1 ml/min and with detection at 220 nm.

The compounds purified by preparative HPLC are isolated as trifluoro-acetates.

Mass spectrometry (MS) by means of FAB (fast atom bombardment): MS-FAB $(M+H)^+$.

The examples explain the invention without the latter being restricted thereto.

If the compounds described as examples are able to exist as various stereoisomers and no stereochemical data are given, mixtures of the stereoisomers are present in each case.

EXAMPLE 1

Synthesis of 3-biphenyl-4-yl-3-{2-[4-(pyridin-2-ylamino) pentanoylamino]-pentanoylamino}propionic acid

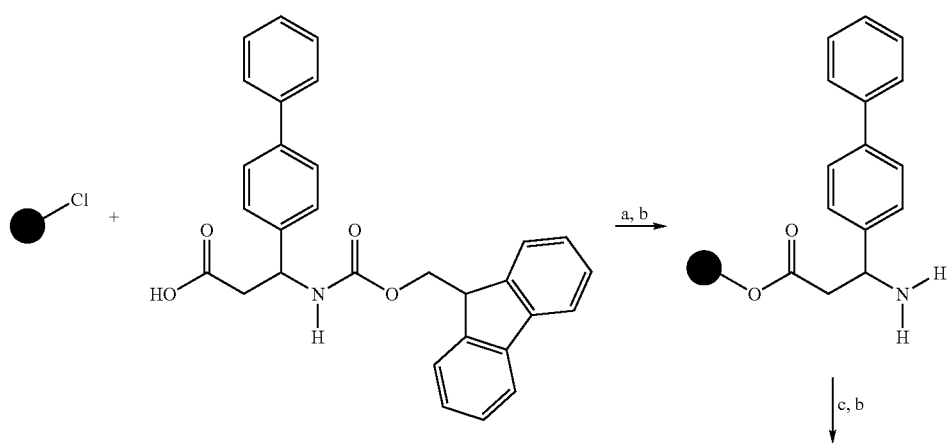

-continued

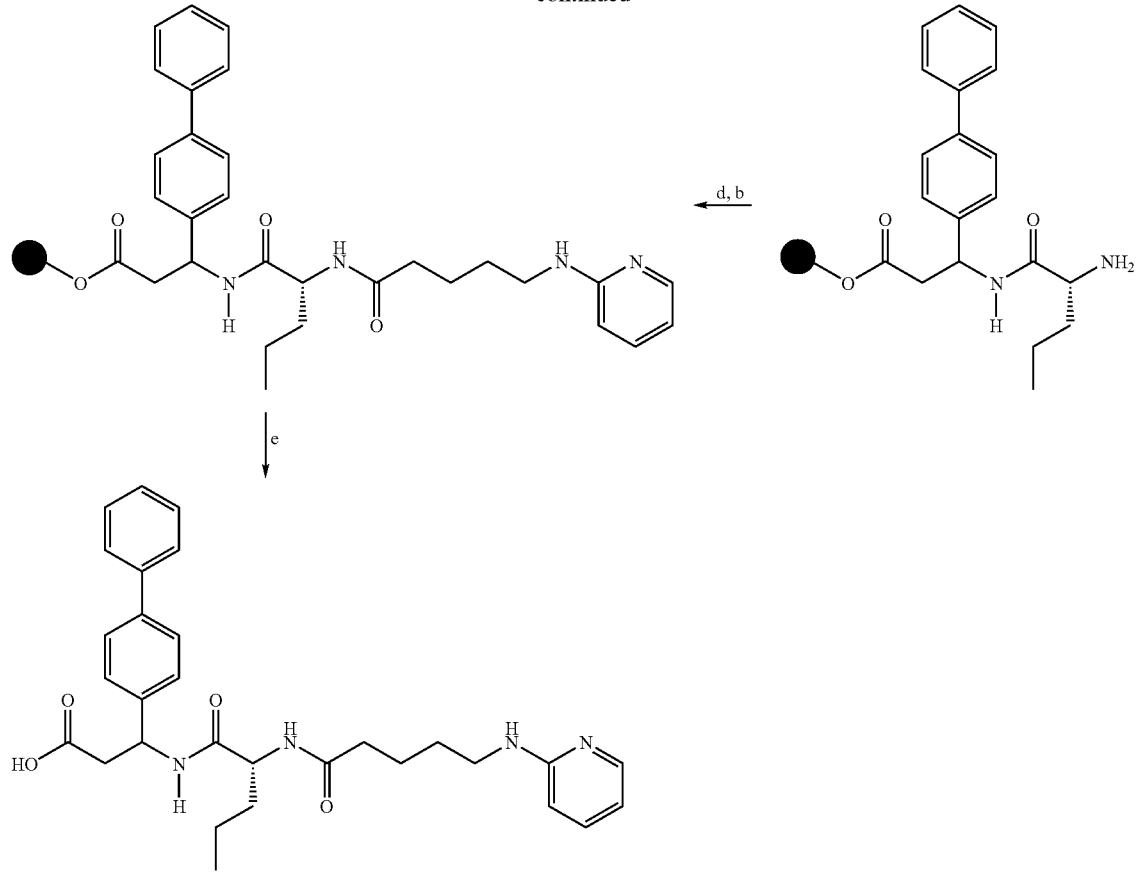

a 9.236 g of 2-chlorotrityl chloride resin (Novabiochem) are suspended in 80 ml of dichloromethane, and 3.9 ml of diisopropylethylamine are subsequently added. A solution of 7.00 g of Fmoc-diphenylamino-propionic acid in dichloromethane is added to this suspension, and the mixture is subsequently shaken at RT for 2 hours. For work-up, the solid phase is filtered off and washed three times with each of DMF, dichloromethane and methanol and dried in a vacuum drying cabinet.

b The solid phase is suspended in DMF, a 50% solution of piperidine in DMF is subsequently added, and the mixture is shaken at RT for 30 minutes. The solid phase is subsequently filtered off, and the same procedure is repeated twice. The solid phase is subsequently washed three times with each of DMF, dichloromethane and methanol and dried overnight in a vacuum drying cabinet, giving resin-bound 3-biphenyl-4-yl-3-aminopropionic acid "AB".

c 250 mg of solid phase are suspended in 2 ml of DMF, and 0.418 ml of diisopropylethylamine is added. 463 mg of Fmoc-D-norvalin, 292 mg of HOBt and 0.287 ml of diisopropylcarbodiimide in the form of a solution in 1 ml of DMF are subsequently added, and the reaction batch is shaken overnight at RT. For work-up, the solid phase is filtered off, washed three times with each of DMF, dichloromethane and methanol and dried overnight in a vacuum drying cabinet, giving resin-bound 2-aminopentanoylamino-3-(biphenyl-4-yl)propionic acid "BC".

d 150 mg of polymer are suspended in 1 ml of DMF, 84 μl of diisopropylethylamine are added, and a solution of 55.7 mg of 5-(2-pyridyl)aminovaleric acid, 63 mg of HOBt and 50 μl of diisopropylcarbodiimide is subsequently added. This suspension is shaken overnight at RT. For work-up, the solid phase is filtered off, washed three times with each of DMF, dichloromethane and methanol and dried overnight in a vacuum drying cabinet, giving resin-bound 3-biphenyl-4-yl-3-{2-[4-(pyridin-2-ylamino)pentanoylamino]pentanoylamino}propionic acid "CD".

e 150 mg of the polymer are suspended in 1 ml of dichloromethane, 3 ml of a 50% solution of TFA in dichloromethane are subsequently added, and the mixture is shaken at RT for 1 hour. The solid phase is removed by filtration, and the solution is evaporated to dryness in a Speedvac, giving 72.28 mg of the desired product as a slightly brownish oil.

EXAMPLE 2

Analogously to Example 1, the resin "AB" is reacted with FMOC-protected L-alanine and 4-(2-pyridin-2-ylamino)butanoic acid, giving 3-biphenyl-4-yl-3-{2-[4-(pyridin-2-ylamino)butanoylamino]-(2S)-propanoylamino}propionic acid.

Preparative HPLC gives 3-biphenyl-4-yl-3-{2-[4-(pyridin-2-ylamino)butanoylamino]-(2S)-propanoylamino}propionic acid trifluoroacetate, RT 1.131/1.169 min, FAB-MS (M+H)$^+$ 475.1.

Analogously to Example 1, the resin "AB" is reacted with FMOC-protected D-alanine and 4-(2-pyridin-2-ylamino)butanoic acid, giving 3-biphenyl-4-yl-3-{2-[4-(pyridin-2-ylamino)butanoylamino]-(2R)-propanoylamino}propionic acid.

Preparative HPLC gives 3-biphenyl-4-yl-3-{2-[4-(pyridin-2-ylamino)butanoylamino]-(2R)-propanoylamino}propionic acid trifluoroacetate, RT 1.137/1.172 min, FAB-MS (M+H)+ 475.1.

Analogously to Example 1, the resin "AB" is reacted with FMOC-protected L-methionine and 4-(2-pyridin-2-ylamino)butanoic acid, giving 3-biphenyl-4-yl-3-{4-methylsulfanyl-2-[4-(pyridin-2-ylamino)butanoylamino]-(2S)-butanoylamino}propionic acid.

Preparative HPLC gives 3-biphenyl-4-yl-3-{4-methylsulfanyl-2-[4-(pyridin-2-ylamino)butanoylamino]-(2S)-butanoylamino}propionic acid trifluoroacetate, RT 1.264/1.362 min, FAB-MS (M+H)+ 535.2.

Analogously to Example 1, the resin "AB" is reacted with FMOC-protected D-methionine and 4-(2-pyridin-2-ylamino)butanoic acid, giving 3-biphenyl-4-yl-3-{4-methylsulfanyl-2-[4-(pyridin-2-ylamino)butanoylamino]-(2R)-butanoylamino}propionic acid.

Preparative HPLC gives 3-biphenyl-4-yl-3-{4-methylsulfanyl-2-[4-(pyridin-2-ylamino)butanoylamino]-(2R)-butanoylamino}propionic acid trifluoroacetate, RT 1.256/1.357 min, FAB-MS (M+H)+ 535.2.

Analogously to Example 1, the resin "AB" is reacted with FMOC-protected L-valine and 4-(2-pyridin-2-ylamino)butanoic acid, giving 3-biphenyl-4-yl-3-{3-methyl-2-[4-(pyridin-2-ylamino)-(2S)-butanoylamino]butanoylamino}propionic acid.

Preparative HPLC gives 3-biphenyl-4-yl-3-{3-methyl-2-[4-(pyridin-2-ylamino)butanoylamino]-(2S)-butanoylamino}propionic acid trifluoroacetate, RT 1.195/1.331 min, FAB-MS (M+H)+ 503.1.

Analogously to Example 1, the resin "AB" is reacted with FMOC-protected D-valine and 4-(2-pyridin-2-ylamino)butanoic acid, giving 3-biphenyl-4-yl-3-{3-methyl-2-[4-(pyridin-2-ylamino)-(2R)-butanoylamino]butanoylamino}-propionic acid.

Preparative HPLC gives 3-biphenyl-4-yl-3-{3-methyl-2-[4-(pyridin-2-ylamino)butanoylamino]-(2R)-butanoylamino}propionic acid trifluoroacetate, RT 1.207/1.334 min, FAB-MS (M+H)+ 503.1.

Analogously to Example 1, the resin "AB" is reacted with FMOC-protected L-leucine and 4-(2-pyridin-2-ylamino)butanoic acid, giving 3-biphenyl-4-yl-3-{4-methyl-2-[4-(pyridin-2-ylamino)butanoylamino]-(2S)-pentanoylamino}-propionic acid.

Preparative HPLC gives 3-biphenyl-4-yl-3-{4-methyl-2-[4-(pyridin-2-ylamino)butanoylamino]-(2S)-pentanoylamino}propionic acid trifluoroacetate, RT 1.335/1.452 min, FAB-MS (M+H)+ 517.2.

Analogously to Example 1, the resin "AB" is reacted with FMOC-protected D-leucine and 4-(2-pyridin-2-ylamino)butanoic acid, giving 3-biphenyl-4-yl-3-{4-methyl-2-[4-(pyridin-2-ylamino)butanoylamino]-(2R)-pentanoylamino}-propionic acid.

Preparative HPLC gives 3-biphenyl-4-yl-3-{4-methyl-2-[4-(pyridin-2-ylamino)butanoylamino]-(2R)-pentanoylamino}propionic acid trifluoroacetate, RT 1.329/1.449 min, FAB-MS (M+H)+ 517.2.

Analogously to Example 1, the resin "AB" is reacted with FMOC-protected L-aspartic acid and 4-(2-pyridin-2-ylamino)butanoic acid, giving N-(1-biphenyl-4-yl-2-carboxyethyl)-3-[4-(pyridin-2-ylamino)butanoylamino]-(2S)-succinamic acid.

Preparative HPLC gives N-(1-biphenyl-4-yl-2-carboxyethyl)-3-[4-(pyridin-2-ylamino)butanoylamino]-(2S)-succinamic acid trifluoroacetate, RT 1.118 min, FAB-MS (M+H)+ 519.2.

Analogously to Example 1, the resin "AB" is reacted with FMOC-protected L-aspartic acid and 4-(2-pyridin-2-ylamino)butanoic acid, giving N-(1-biphenyl-4-yl-2-carboxyethyl)-3-[4-(pyridin-2-ylamino)butanoylamino]-(2R)-succinamic acid.

Preparative HPLC gives N-(1-biphenyl-4-yl-2-carboxyethyl)-3-[4-(pyridin-2-ylamino)butanoylamino]-(2R)-succinamic acid trifluoroacetate, RT 1.094 min, FAB-MS (M+H)+ 519.2.

Analogously to Example 1, the resin "AB" is reacted with FMOC-protected (2R)-2-amino-3-cyclohexyl-propanoic acid and 4-(2-pyridin-2-ylamino)-butanoic acid, giving 3-biphenyl-4-yl-3-{3-cyclohexyl-2-[4-(pyridin-2-ylamino)butanoylamino]-(2R)-propanoylamino}propionic acid.

Preparative HPLC gives 3-biphenyl-4-yl-3-{3-cyclohexyl-2-[4-(pyridin-2-ylamino)butanoylamino]-(2R)-propanoylamino}propionic acid trifluoroacetate, RT 1.527/1.653 min, FAB-MS (M+H)+ 557.3.

Analogously to Example 1, the resin "AB" is reacted with FMOC-protected L-glutamic acid and 4-(2-pyridin-2-ylamino)butanoic acid, giving 4-(1-biphenyl-4yl-2-carboxyethylcarbamoyl)4-[4-(pyridin-2-ylamino)butanoylamino]-(4S)-butanoic acid.

Preparative HPLC gives 4-(1-biphenyl-4yl-2-carboxy-ethylcarbamoyl)-4-[4-(pyridin-2-ylamino)butanoylamino]-(4S)-butanoic acid trifluoroacetate, RT 1.142 min, FAB-MS (M+H)+ 533.2.

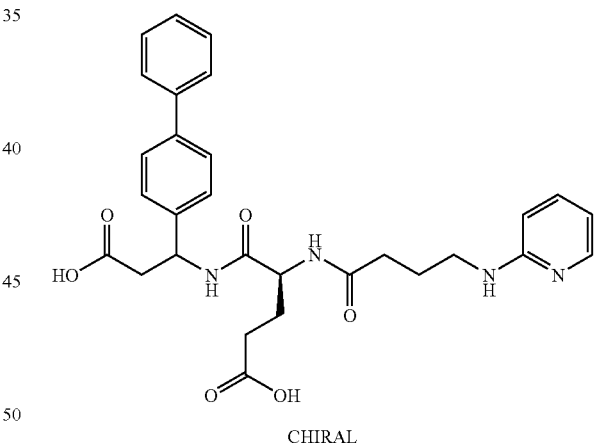

CHIRAL

Analogously to Example 1, the resin "AB" is reacted with FMOC-protected D-phenylalanine and 4-(2-pyridin-2-ylamino)butanoic acid, giving 3-biphenyl-4-yl-3-{3-phenyl-2-[4-(pyridin-2-ylamino)butanoylamino]-(2R)-propanoylamino}propionic acid.

Preparative HPLC gives 3-biphenyl-4-yl-3-{3-phenyl-2-[4-(pyridin-2-ylamino)butanoylamino]-(2R)-propanoylamino}propionic acid trifluoroacetate, RT 1.378/1.500 min, FAB-MS (M+H)+ 551.2.

Analogously to Example 1, the resin "AB" is reacted with FMOC-protected L-threonine and 4-(2-pyridin-2-ylamino)butanoic acid, giving 3-biphenyl-4-yl-3-{3-hydroxy-2-[4-(pyridin-2-ylamino)butanoylamino]-(2S)-butanoylamino}propionic acid.

Preparative HPLC gives 3-biphenyl-4-yl-3-{3-hydroxy-2-[4-(pyridin-2-ylamino)-(2S)-butanoylamino]butanoylamino}propionic acid trifluoroacetate, RT 1.097 min, FAB-MS (M+H)+ 505.2.

Analogously to Example 1, the resin "AB" is reacted with FMOC-protected L-tyrosine and 4-(2-pyridin-2-ylamino)butanoic acid, giving 3-biphenyl-4-yl-3-{3-(4-hydroxy-phenyl-)$_2$-[4-(pyridin-2-ylamino)butanoylamino]-(2S)-propanoylamino}propionic acid.

Preparative HPLC gives 3-biphenyl-4-yl-3-{3-(4-hydroxy-phenyl-)$_2$-[4-(pyridin-2-ylamino)butanoylamino]-(2S)-propanoylamino}propionic acid trifluoroacetate, RT 1.241/1.300 min, FAB-MS (M+H)+ 567.2.

Analogously to Example 1, the resin "AB" is reacted with FMOC-protected L-phenylalanine and 4-(2-pyridin-2-ylamino)butanoic acid, giving 3-biphenyl-4-yl-3-{3-phenyl-2-[4-(pyridin-2-ylamino)butanoylamino]-(2S)-propanoylamino}propionic acid.

Preparative HPLC gives 3-biphenyl-4-yl-3-{3-phenyl-2-[4-(pyridin-2-ylamino)butanoylamino]-(2S)-propanoylamino}propionic acid trifluoroacetate, RT 1.380/1.501 min, FAB-MS (M+H)+ 551.2.

Analogously to Example 1, the resin "AB" is reacted with FMOC-protected 2-amino-2-methylpropionic acid and 4-(2-pyridin-2-ylamino)butanoic acid, giving 3-biphenyl-4-yl-3-{2-methyl-2-[4-(pyridin-2-ylamino)butanoylamino]-propanoylamino}propionic acid.

Preparative HPLC gives 3-biphenyl-4-yl-3-{2-methyl-2-[4-(pyridin-2-ylamino)butanoylamino]propanoylamino}propionic acid trifluoroacetate, RT 1.156 min, FAB-MS (M+H)+ 489.1.

Analogously to Example 1, the resin "AB" is reacted with FMOC-protected L-serine and 4-(2-pyridin-2-ylamino)butanoic acid, giving 3-biphenyl-4-yl-3-{3-hydroxy-2-[4-(pyridin-2-ylamino)butanoylamino]-(2S)-propanoylamino}-propionic acid.

Preparative HPLC gives 3-biphenyl-4-yl-3-{3-hydroxy-2-[4-(pyridin-2-ylamino)butanoylamino]-(2S)-propanoylamino}propionic acid trifluoroacetate, RT 1.049 min, FAB-MS (M+H)+ 491.1.

Analogously to Example 1, the resin "AB" is reacted with FMOC-protected D-serine and 4-(2-pyridin-2-ylamino)butanoic acid, giving 3-biphenyl-4-yl-3-{3-hydroxy-2-[4-(pyridin-2-ylamino)butanoylamino]-(2R)-propanoylamino}propionic acid.

Preparative HPLC gives 3-biphenyl-4-yl-3-{3-hydroxy-2-[4-(pyridin-2-ylamino)butanoylamino]-(2R)-propanoylamino}propionic acid trifluoroacetate, RT 1.072 min, FAB-MS (M+H)+ 491.1.

Analogously to Example 1, the resin "AB" is reacted with FMOC-protected (2S)-2-aminohexanoic acid and 4-(2-pyridin-2-ylamino)butanoic acid, giving 3-biphenyl-4-yl-3-{2-[4-(pyridin-2-ylamino)butanoylamino]-(2S)-hexanoylamino}propionic acid.

Preparative HPLC gives 3-biphenyl-4-yl-3-{2-[4-(pyridin-2-ylamino)butanoylamino]-(2S)-hexanoylamino}propionic acid trifluoroacetate, RT 1.302/1.437 min, FAB-MS (M+H)+ 517.2.

Analogously to Example 1, the resin "AB" is reacted with FMOC-protected (2R)-2-aminohexanoic acid and 4-(2-pyridin-2-ylamino)butanoic acid, giving 3-biphenyl-4-yl-3-{2-[4-(pyridin-2-ylamino)butanoylamino]-(2R)-hexanoylamino}propionic acid.

Preparative HPLC gives 3-biphenyl-4-yl-3-{2-[4-(pyridin-2-ylamino)butanoylamino]-(2R)-hexanoylamino}propionic acid trifluoroacetate, RT 1.30211.425 min, FAB-MS (M+H)+ 517.2.

Analogously to Example 1, the resin "AB" is reacted with FMOC-protected S-trityl-L-cysteine and 4-(2-pyridin-2-ylamino)butanoic acid, giving 3-biphenyl-4-yl-3-{2-[4-(pyridin-2-ylamino)butanoylamino]-3-tritylsulfanyl-(2S)-propanoylamino}propionic acid.

Preparative HPLC gives 3-biphenyl-4-yl-3-{2-[4-(pyridin-2-ylamino)butanoylamino]-3-tritylsulfanyl-(2S)-propanoylamino}propionic acid trifluoroacetate, RT 1.884/1.969 min, FAB-MS (M+H)+ 750.2.

Analogously to Example 1, the resin "AB" is reacted with FMOC-protected S-trityl-D-cysteine and 4-(2-pyridin-2-ylamino)butanoic acid, giving 3-biphenyl-4-yl-3-{2-[4-(pyridin-2-ylamino)butanoylamino]-3-tritylsulfanyl-(2R)-propanoylamino}propionic acid.

Preparative HPLC gives 3-biphenyl-4-yl-3-{2-[4-(pyridin-2-ylamino)butanoylamino]-3-tritylsulfanyl-(2R)-propanoylamino}propionic acid trifluoroacetate, RT 1.894/1.978 min, FAB-MS (M+H)+ 750.2.

Analogously to Example 1, the resin "AB" is reacted with FMOC-protected L-lysine and 4-(2-pyridin-2-ylamino)butanoic acid, giving 3-biphenyl-4-yl-3-{6-amino-2-[(4-(pyridin-2-ylamino)butanoylamino]-(2S)-hexanoylamino}-propionic acid.

Preparative HPLC gives 3-biphenyl-4-yl-3-{6-amino-2-[4-(pyridin-2-ylamino)butanoylamino]-(2S)-hexanoylamino}propionic acid trifluoroacetate, RT 0.763/0.799 min, FAB-MS (M+H)+ 266.6/532.2.

Analogously to Example 1, the resin "AB" is reacted with FMOC-protected D-lysine and 4-(2-pyridin-2-ylamino)butanoic acid, giving 3-biphenyl-4-yl-3-{6-amino-2-[4-(pyridin-2-ylamino)butanoylamino]-(2R)-hexanoylamino}-propionic acid.

Preparative HPLC gives 3-biphenyl-4-yl-3-{6-amino-2-[4-(pyridin-2-ylamino)butanoylamino]-(2R)-hexanoylamino}propionic acid trifluoroacetate, RT 0.784/0.820 min, FAB-MS (M+H)+ 266.6/532.2.

Analogously to Example 1, the resin "AB" is reacted with FMOC-protected (S)-2-aminobutanoic acid and 4-(2-pyridin-2-ylamino)butanoic acid, giving 3-biphenyl-4-yl-3-{2-[4-(pyridin-2-ylamino)butanoylamino]-(2S)-butanoylamino}propionic acid.

Preparative HPLC gives 3-biphenyl-4-yl-3-{2-[4-(pyridin-2-ylamino)butanoylamino]-(2S)-butanoylamino}propionic acid trifluoroacetate, RT 1.154/1.242 min, FAB-MS (M+H)+ 489.2.

Analogously to Example 1, the resin "AB" is reacted with FMOC-protected D-tyrosine and 4-(2-pyridin-2-ylamino)butanoic acid, giving 3-biphenyl-4-yl-3-{3-(4-hydroxyphenyl)-2-[4-(pyridin-2-ylamino)butanoylamino]-(2R)-propanoylamino}propionic acid.

Preparative HPLC gives 33-biphenyl-4-yl-3-{3-(4-hydroxyphenyl)-2-[4-(pyridin-2-ylamino)butanoylamino]-(2R)-propanoylamino}propionic acid trifluoroacetate, RT 1.201/1.263 min, FAB-MS (M+H)+ 567.2.

Analogously to Example 1, the resin "AB" is reacted with FMOC-protected (2R)-2,5-diaminopentanoic acid and 4-(2-pyridin-2-ylamino)butanoic acid, giving 3-biphenyl-4-yl-3-{5-amino-2-[4-(pyridin-2-ylamino)butanoylamino]-(2R)-pentanoylamino}propionic acid.

Preparative HPLC gives 3-biphenyl-4-yl-3-{5-amino-2-[4-(pyridin-2-ylamino)butanoylamino]-(2R)-pentanoylamino}propionic acid trifluoroacetate, RT 0.772 min, FAB-MS (M+H)+ 259.6/518.2.

Analogously to Example 1, the resin "AB" is reacted with FMOC-protected D-arginine and 4-(2-pyridin-2-ylamino)butanoic acid, giving 3-biphenyl-4-yl-3-{5-guanidino-2-[4-

(pyridin-2-ylamino)butanoylamino]-(2R)-pentanoylamino}propionic acid.

Preparative HPLC gives 3-biphenyl-4-yl-3-{5-guanidino-2-[4-(pyridin-2-ylamino)butanoylamino]-(2R)-pentanoylamino}propionic acid trifluoroacetate, RT 0.341 min, FAB-MS (M+H)+ 280.6/560.3.

Analogously to Example 1, the resin "AB" is reacted with FMOC-protected D-histidine and 4-(2-pyridin-2-ylamino)butanoic acid, giving 3-biphenyl-4-yl-3-{3-1H-imidazol-4-yl-2-[4-(pyridin-2-ylamino)butanoylamino]-(2R)-propionylamino}propionic acid.

Preparative HPLC gives 3-biphenyl-4-yl-3-{3-1H-imidazol-4-yl-2-[4-(pyridin-2-ylamino)butanoylamino]-(2R)-propionylamino}propionic acid trifluoroacetate, RT 0.735 min, FAB-MS (M+H)+ 541.2.

Analogously to Example 1, the resin "AB" is reacted with FMOC-protected (2R)-2-amino-3,3-dimethylbutanoic acid and 4-(2-pyridin-2-ylamino)butanoic acid, giving 3-biphenyl-4-yl-3-{3,3-dimethyl-2-[4-(pyridin-2-ylamino)butanoylamino]-(2R)-butanoylamino}propionic acid.

Preparative HPLC gives 3-biphenyl-4-yl-3-{3,3-dimethyl-2-[4-(pyridin-2-ylamino)butanoylamino]-(2R)-butanoylamino}propionic acid trifluoroacetate, RT 1.290/1.387 min, FAB-MS (M+H)+ 517.2.

Analogously to Example 1, the resin "AB" is reacted with FMOC-protected (2R)-2-amino-2-phenylacetic acid and 4-(2-pyridin-2-ylamino)butanoic acid, giving 3-biphenyl-4-yl-3-{2-phenyl-2-[(4-(pyridin-2-ylamino)butanoylamino]-(2R)-ethanoylamino}propionic acid.

Preparative HPLC gives 3-biphenyl-4-yl-3-{2-phenyl-2-[4-(pyridin-2-ylamino)butanoylamino]-(2R)-ethanoylamino}propionic acid trifluoroacetate, RT 1.286/1.392 min, FAB-MS (M+H)+ 537.2.

Analogously to Example 1, the resin "AB" is reacted with FMOC-protected D-threonine and 4-(2-pyridin-2-ylamino)butanoic acid, giving 3-biphenyl-4-yl-3-{3-hydroxy-2-[4-(pyridin-2-ylamino)butanoylamino]-(2R)-butanoylamino}propionic acid.

Preparative HPLC gives 3-biphenyl-4-yl-3-{3-hydroxy-2-[4-(pyridin-2-ylamino)butanoylamino]-(2R)-butanoylamino}propionic acid trifluoroacetate, RT 1.083 min, FAB-MS (M+H)+ 505.2.

Analogously to Example 1, the resin "AB" is reacted with FMOC-protected D-glutamic acid and 4-(2-pyridin-2-ylamino)butanoic acid, giving 3-biphenyl-4-yl-3-{4-carboxy-2-[4-(pyridin-2-ylamino)butanoylamino]-(2R)-butanoylamino}propionic acid.

Preparative HPLC gives 3-biphenyl-4-yl-3-{4-carboxy-2-[4-(pyridin-2-ylamino)butanoylamino]-(2R)-butanoylamino}propionic acid trifluoroacetate, RT 1.092 min, FAB-MS (M+H)+ 533.2.

Analogously to Example 1, the resin "AB" is reacted with FMOC-protected L-glutamine and 4-(2-pyridin-2-ylamino)butanoic acid, giving 3-biphenyl-4-yl-3-{4-carbamoyl-2-[4-(pyridin-2-ylamino)butanoylamino]-(2S)-butanoylamino}propionic acid.

Preparative HPLC gives 3-biphenyl-4-yl-3-{4-carbamoyl-2-[4-(pyridin-2-ylamino)butanoylamino]-(2S)-butanoylamino}propionic acid trifluoroacetate, RT 1.066 min, FAB-MS (M+H)+ 532.2.

Analogously to Example 1, the resin "AB" is reacted with FMOC-protected (2S)-2-amino-4-hydroxybutanoic acid and 4-(2-pyridin-2-ylamino)butanoic acid, giving 3-biphenyl-4-yl-3-{4-hydroxy-2-[4-(pyridin-2-ylamino)butanoylamino]-(2S)-butanoylamino}propionic acid.

Preparative HPLC gives 3-biphenyl-4-yl-3-{4-hydroxy-2-[4-(pyridin-2-ylamino)butanoylamino]-(2S)-butanoylamino}propionic acid trifluoroacetate, RT 1.106/1.301 min, FAB-MS (M+H)+ 505.2.

Analogously to Example 1, the resin "AB" is reacted with FMOC-protected 1-amino-1-carboxycyclohexane and 4-(2-pyridin-2-ylamino)butanoic acid, giving 3-biphenyl-4-yl-3-{1-[1-[(4-(pyridin-2-ylaminobutanoylamino)cyclohexyl]methanoylamino}propionic acid.

Preparative HPLC gives 3-biphenyl-4-yl-3-{1-[1-(4-pyridin-2-ylaminobutanoylamino)cyclohexyl]methanoylamino}propionic acid trifluoroacetate, RT 1.284 min, FAB-MS (M+H)+ 529.2.

Analogously to Example 1, the resin "AB" is reacted with FMOC-protected (2S)-2-aminopentanoic acid and 4-(2-pyridin-2-ylamino)butanoic acid, giving 3-biphenyl-4-yl-3-{-2-[4-(pyridin-2-ylamino)butanoylamino]-(2S)-pentanoylamino}propionic acid.

Preparative HPLC gives 3-biphenyl-4-yl-3-{-2-[4-(pyridin-2-ylamino)butanoylamino]-(2S)-pentanoylamino}propionic acid trifluoroacetate, RT 1.189/1.314 min, FAB-MS (M+H)+ 503.2.

Analogously to Example 1, the resin "AB" is reacted with FMOC-protected (2R)-2-aminopentanoic acid and 4-(2-pyridin-2-ylamino)butanoic acid, giving 3-biphenyl-4-yl-3-{-2-[4-(pyridin-2-ylamino)butanoylamino]-(2R)pentanoylamino}propionic acid.

Preparative HPLC gives 3-biphenyl-4-yl-3-{-2-[4-(pyridin-2-ylamino)butanoylamino]-(2R)-pentanoylamino}propionic acid trifluoroacetate, RT 1.247/1.358 min, FAB-MS (M+H)+ 503.2.

Analogously to Example 1, the resin "AB" is reacted with FMOC-protected (2S)-2,5-diaminopentanoic acid and 4-(2-pyridin-2-ylamino)butanoic acid, giving 3-biphenyl-4-yl-3-{5-amino-2-[4-(pyridin-2-ylamino)butanoylamino]-(2S)-pentanoylamino}propionic acid.

Preparative HPLC gives 3-biphenyl-4-yl-3-{5-amino-2-[4-(pyridin-2-ylamino)butanoylamino]-(2S)-pentanoylamino}propionic acid trifluoroacetate, RT 0.634 min, FAB-MS (M+H)+ 518.2.

Analogously to Example 1, the resin "AB" is reacted with FMOC-protected (2S)-2-amino-3-thiophen-2-ylpropionic acid and 4-(2-pyridin-2-ylamino)butanoic acid, giving 3-biphenyl-4-yl-3-{-2-[4-(pyridin-2-ylamino)butanoylamino]-3-thiophen-2-yl-(2S)-propanoylamino}propionic acid.

Preparative HPLC gives 3-biphenyl-4-yl-3-{-2-[4-(pyridin-2-ylamino)-butanoylamino]-3-thiophen-2-yl-(2S)-propanoylamino}propionic acid trifluoroacetate, RT 1.286/1.416 min, FAB-MS (M+H)+ 557.2.

Analogously to Example 1, the resin "AB" is reacted with FMOC-protected (2S)-2-amino-3-pyridin-4-ylpropionic acid and 4-(2-pyridin-2-ylamino)-butanoic acid, giving 3-biphenyl-4-yl-3-{-3-pyridin-4-yl-2-[4-(pyridin-2-ylamino)butanoylamino]-(2S)-propanoylamino}propionic acid.

Preparative HPLC gives 3-biphenyl-4-yl-3-{-3-pyridin-4-yl-2-[4-(pyridin-2-ylamino)butanoylamino]-(2S)-propanoylamino}propionic acid trifluoroacetate, RT 0.821/0.904 min, FAB-MS (M+H)+ 276.6/552.2.

Analogously to Example 1, the resin "AB" is reacted with FMOC-protected (2R)-2-amino-3-pyridin-4-ylpropionic acid and 4-(2-pyridin-2-ylamino)-butanoic acid, giving 3-biphenyl-4-yl-3-{-3-pyridin-4-yl-2-[4-(pyridin-2-ylamino)butanoylamino]-(2R)-propanoylamino}propionic acid.

Preparative HPLC gives 3-biphenyl-4-yl-3-{-3-pyridin-4-yl-2-[4-(pyridin-2-ylamino)butanoylamino]-(2R)-propanoylamino}propionic acid trifluoroacetate, RT 0.875/0.936 min, FAB-MS (M+H)+ 276.6/552.2.

Analogously to Example 1, the resin "AB" is reacted with FMOC-protected 2-amino-3-indol-2-ylpropionic acid and 4-(2-pyridin-2-ylamino)butanoic acid, giving 3-biphenyl-4-yl-3-{-3-indol-2-yl-2-[4-(pyridin-2-ylamino)butanoylamino]propanoylamino}propionic acid.

Preparative HPLC gives 3-biphenyl-4-yl-3-{-3-indol-2-yl-2-[4-(pyridin-2-ylamino)butanoylamino]propanoic acid trifluoroacetate, RT 1.435/1.521 min, FAB-MS (M+H)$^+$ 590.2.

Analogously to Example 1, the resin "AB" is reacted with FMOC-protected L-histidine and 4-(2-pyridin-2-ylamino)butanoic acid, giving 3-biphenyl-4-yl-3-{3-1H-imidazol-4-yl-2-[4-(pyridin-2-ylamino)butanoylamino]-(2S)-propionylamino}propionic acid.

Preparative HPLC gives 3-biphenyl-4-yl-3-{3-1H-imidazol-4-yl-2-[4-(pyridin-2-ylamino)butanoylamino]-(2S)-propionylamino}propionic acid trifluoroacetate, RT 0.727 min, FAB-MS (M+H)$^+$ 541.2.

Analogously to Example 1, the resin "AB" is reacted with FMOC-protected (2S)-2-amino-3,3-dimethylbutanoic acid and 4-(2-pyridin-2-ylamino)-butanoic acid, giving 3-biphenyl-4-yl-3-{3,3-dimethyl-2-[4-(pyridin-2-ylamino)butanoylamino]-(2S)-butanoylamino}propionic acid.

Preparative HPLC gives 3-biphenyl-4-yl-3-{3,3-dimethyl-2-[4-(pyridin-2-ylamino)butanoylamino]-(2S)-butanoylamino}propionic acid trifluoroacetate, RT 1.252/1.419 min, FAB-MS (M+H)$^+$ 517.2.

Analogously to Example 1, the resin "AB" is reacted with FMOC-protected (2S)-2-amino-3-cyclohexylpropanoic acid and 4-(2-pyridin-2-ylamino)-butanoic acid, giving 3-biphenyl-4-yl-3-{3-cyclohexyl-2-[4-(pyridin-2-ylamino)butanoylamino]-(2S)-propanoylamino}propionic acid.

Preparative HPLC gives 3-biphenyl-4-yl-3-{3-cyclohexyl-2-[4-(pyridin-2-ylamino)butanoylamino]-(2S)-propanoylamino}propionic acid trifluoroacetate, RT 1.496/1.615 min, FAB-MS (M+H)$^+$ 557.4.

Analogously to Example 1, the resin "AB" is reacted with FMOC-protected L-arginine and 4-(2-pyridin-2-ylamino)butanoic acid, giving 3-biphenyl-4-yl-3-{5-guanidino-2-[4-(pyridin-2-ylamino)butanoylamino]-(2S)-pentanoylamino}propionic acid.

Preparative HPLC gives 3-biphenyl-4-yl-3-{5-guanidino-2-[4-(pyridin-2-ylamino)butanoylamino]-(2S)-pentanoylamino}propionic acid trifluoroacetate, RT 0.381 min, FAB-MS (M+H)$^+$ 280.6/560.3.

Analogously to Example 1, the resin "AB" is reacted with FMOC-protected (2S)-2-amino-3-indol-2-ylpropanoic acid and 4-(2-pyridin-2-ylamino)butanoic acid, giving 3-biphenyl-4-yl-3-{-3-indol-2-yl-2-[4-(pyridin-2-ylamino)butanoylamino]-(2S)-propanoylamino}propionic acid.

Preparative HPLC gives 3-biphenyl-4-yl-3-{-3-indol-2-yl-2-[4-(pyridin-2-ylamino)butanoylamino]-(2S)-propanoylamino}propionic acid trifluoroacetate, RT 1.421/1.515 min, FAB-MS (M+H)$^+$ 590.2.

Analogously to Example 1, the resin "AB" is reacted with FMOC-protected L-glutamine and 5-(2-pyridin-2-ylamino)pentanoic acid, giving 3-biphenyl-4-yl-3-{4-carbamoyl-2-[5-(pyridin-2-ylamino)pentanoylamino]-(2S)-butanoylamino}propionic acid.

Preparative HPLC gives 3-biphenyl-4-yl-3-{4-carbamoyl-2-[5-(pyridin-2-ylamino)pentanoylamino]-(2S)-butanoylamino}propionic acid trifluoroacetate, RT 0.956 min, FAB-MS (M+H)$^+$ 546.2.

Analogously to Example 1, the resin "AB" is reacted with FMOC-protected L-serine and 5-(2-pyridin-2-ylamino)pentanoic acid, giving 3-biphenyl-4-yl-3-{4-hydroxy-2-[5-(pyridin-2-ylamino)pentanoylamino]-(2S)-butanoylamino}-propionic acid.

Preparative HPLC gives 3-biphenyl-4-yl-3-{4-hydroxy-2-[5-(pyridin-2-ylamino)pentanoylamino]-(2S)-butanoylamino}propionic acid trifluoroacetate, RT 1.06 min, FAB-MS (M+H)$^+$ 519.2.

Analogously to Example 1, the resin "AB" is reacted with FMOC-protected 1-amino-1-carboxycyclohexane and 5-(2-pyridin-2-ylamino)pentanoic acid, giving 3-biphenyl-4-yl-3-{1-[1-(5-pyridin-2-ylaminopentanoylamino)cyclohexyl]methanoylamino}propionic acid.

Preparative HPLC gives 3-biphenyl-4-yl-3-{1-[1-(5-pyridin-2-ylaminopentanoylamino)cyclohexyl]methanoylamino}propionic acid trifluoroacetate, RT 1.275 min, FAB-MS (M+H)$^+$ 543.2.

Analogously to Example 1, the resin "AB" is reacted with FMOC-protected (2S)-2-aminopentanoic acid and 5-(2-pyridin-2-ylamino)pentanoic acid, giving 3-biphenyl-4-yl-3-{-2-[5-(pyridin-2-ylamino)pentanoylamino]-(2S)-pentanoylamino}propionic acid.

Preparative HPLC gives 3-biphenyl-4-yl-3-{-2-[5-(pyridin-2-ylamino)pentanoylamino]-(2S)-pentanoylamino}propionic acid trifluoroacetate, RT 1.147/1.253 min, FAB-MS (M+H)$^+$ 517.2.

Analogously to Example 1, the resin "AB" is reacted with FMOC-protected (2R)-2-aminopentanoic acid and 5-(2-pyridin-2-ylamino)pentanoic acid, giving 3-biphenyl-4-yl-3-{-2-[5-(pyridin-2-ylamino)pentanoylamino]-(2R)-pentanoylamino}propionic acid.

Preparative HPLC gives 3-biphenyl-4-yl-3-{-2-[5-(pyridin-2-ylamino)pentanoylamino]-(2R)-pentanoylamino}propionic acid trifluoroacetate, RT 1.150/1.258 min, FAB-MS (M+H)$^+$ 517.2.

Analogously to Example 1, the resin "AB" is reacted with FMOC-protected (2R)-2,5-diaminopentanoic acid and 5-(2-pyridin-2-ylamino)pentanoic acid, giving 3-biphenyl-4-yl-3-{5-amino-2-[5-(pyridin-2-ylamino)pentanoylamino]-(2R)-pentanoylamino}propionic acid.

Preparative HPLC gives 3-biphenyl-4-yl-3-{5-amino-2-[5-(pyridin-2-ylamino)pentanoylamino]-(2R)-pentanoylamino}propionic acid trifluoroacetate, RT 0.563 min, FAB-MS (M+H)$^+$ 266.6/532.4.

Analogously to Example 1, the resin "AB" is reacted with FMOC-protected (2S)-2-amino-3-thiophen-2-ylpropionic acid and 5-(2-pyridin-2-ylamino)pentanoic acid, giving 3-biphenyl-4-yl-3-{2-[5-(pyridin-2-ylamino)-pentanoylamino]-3-thiophen-2-yl-(2S)-propanoylamino}propionic acid.

Preparative HPLC gives 3-biphenyl-4-yl-3-{-2-[5-(pyridin-2-ylamino)pentanoylamino]-3-thiophen-2-yl-(2S)-propanoylamino}propionic acid trifluoroacetate, RT 1.238/1.351 min, FAB-MS (M+H)$^+$ 571.2.

Analogously to Example 1, the resin "AB" is reacted with FMOC-protected (2S)-2-amino-3-pyridin-4-ylpropionic acid and 5-(2-pyridin-2-ylamino)-pentanoic acid, giving 3-biphenyl-4-yl-3-{-3-pyridin-4-yl-2-[5-(pyridin-2-ylamino)pentanoylamino]-(2S)-propanoylamino}propionic acid.

Preparative HPLC gives 3-biphenyl-4-yl-3-{-3-pyridin-4-yl-2-[5-(pyridin-2-ylamino)pentanoylamino]-(2S)-propanoylamino}propionic acid trifluoroacetate, RT 0.730/0.845 min, FAB-MS (M+H)$^+$ 283.6/566.2.

Analogously to Example 1, the resin "AB" is reacted with FMOC-protected (2R)-2-amino-3-pyridin-4-ylpropionic acid and 5-(2-pyridin-2-ylamino)-pentanoic acid, giving 3-biphenyl-4-yl-3-{-3-pyridin-4-yl-2-[5-(pyridin-2-ylamino)pentanoylamino]-(2R)-propanoylamino}propionic acid.

Preparative HPLC gives 3-biphenyl-4-yl-3-{-3-pyridin-4-yl-2-[5-(pyridin-2-ylamino)pentanoylamino]-(2R)- propanoylamino}propionic acid trifluoroacetate, RT 0.742/0.849 min, FAB-MS (M+H)+ 283.6/566.2.

Analogously to Example 1, the resin "AB" is reacted with FMOC-protected (2R)-2-amino-3-indol-2-ylpropionic acid and 5-(2-pyridin-2-ylamino)-pentanoic acid, giving 3-biphenyl-4-yl-3-{-3-indol-2-yl-2-[5-(pyridin-2-ylamino)pentanoylamino]-(2R)-propanoylamino}propionic acid.

Preparative HPLC gives 3-biphenyl-4-yl-3-{-3-indol-2-yl-2-[5-(pyridin-2-ylamino)pentanoylamino]-(2R)-propanoylamino}propionic acid trifluoroacetate, RT 1.278/1.361 min, FAB-MS (M+H)+ 604.3.

Analogously to Example 1, the resin "AB" is reacted with FMOC-protected L-histidine and 5-(2-pyridin-2-ylamino)pentanoic acid, giving 3-biphenyl-4-yl-3-{3-1H-imidazol-4-yl-2-[5-(pyridin-2-ylamino)pentanoylamino]-(2S)-propionylamino}propionic acid.

Preparative HPLC gives 3-biphenyl-4-yl-3-{3-1H-imidazol-4-yl-2-[5-(pyridin-2-ylamino)pentanoylamino]-(2S)-propionylamino}propionic acid trifluoroacetate, RT 0.563 min, FAB-MS (M+H)+ 278.2/555.2.

Analogously to Example 1, the resin "AB" is reacted with FMOC-protected D-histidine and 5-(2-pyridin-2-ylamino)pentanoic acid, giving 3-biphenyl-4-yl-3-{3-1H-imidazol-4-yl-2-[5-(pyridin-2-ylamino)pentanoylamino]-(2R)-propionylamino}propionic acid.

Preparative HPLC gives 3-biphenyl-4-yl-3-{3-1H-imidazol-4-yl-2-[5-(pyridin-2-ylamino)pentanoylamino]-(2R)-propionylamino}propionic acid trifluoroacetate, RT 0.616 min, FAB-MS (M+H)+ 278.2/555.2.

Analogously to Example 1, the resin "AB" is reacted with FMOC-protected (2S)-2-amino-3,3-dimethylbutanoic acid and 5-(2-pyridin-2-ylamino)pentanoic acid, giving 3-biphenyl-4-yl-3-{3,3-dimethyl-2-[5-(pyridin-2-ylamino)pentanoylamino]-(2S)-butanoylamino}propionic acid.

Preparative HPLC gives 3-biphenyl-4-yl-3-{3,3-dimethyl-2-[5-(pyridin-2-ylamino)pentanoylamino]-(2S)-butanoylamino}propionic acid trifluoroacetate, RT 1.150/1.325 min, FAB-MS (M+H)+ 531.3.

Analogously to Example 1, the resin "AB" is reacted with FMOC-protected (2S)-2-amino-3-cyclohexylpropanoic acid and 5-(2-pyridin-2-ylamino)-pentanoic acid, giving 3-biphenyl-4-yl-3-{3-cyclohexyl-2-[5-(pyridin-2-ylamino)pentanoylamino]-(2S)-propanoylamino}propionic acid.

Preparative HPLC gives 3-biphenyl-4-yl-3-{3-cyclohexyl-2-[5-(pyridin-2-ylamino)pentanoylamino]-(2S)-propanoylamino}propionic acid trifluoroacetate, RT 1.404/1.518 min, FAB-MS (M+H)+ 571.35.

Analogously to Example 1, the resin "AB" is reacted with FMOC-protected L-arginine and 5-(2-pyridin-2-ylamino)pentanoic acid, giving 3-biphenyl-4-yl-3-{5-guanidino-2-[5-(pyridin-2-ylamino)pentanoylamino]-(2S)-pentanoylamino}propionic acid.

Preparative HPLC gives 3-biphenyl-4-yl-3-{5-guanidino-2-[5-(pyridin-2-ylamino)pentanoylamino]-(2S)-pentanoylamino}propionic acid trifluoroacetate, RT 0.331 min, FAB-MS (M+H)+ 287.8/574.3.

Analogously to Example 1, the resin "AB" is reacted with FMOC-protected D-arginine and 5-(2-pyridin-2-ylamino)pentanoic acid, giving 3-biphenyl-4-yl-3-{5-guanidino-2-[5-(pyridin-2-ylamino)pentanoylamino]-(2R)-pentanoylamino}propionic acid.

Preparative HPLC gives 3-biphenyl-4-yl-3-{5-guanidino-2-[5-(pyridin-2-ylamino)pentanoylamino]-(2R)-pentanoylamino}propionic acid trifluoroacetate, RT 0.325 min, FAB-MS (M+H)+ 287.8/574.3.

Analogously to Example 1, the resin "AB" is reacted with FMOC-protected (2S)-2-amino-3-indol-2-ylpropionic acid and 5-(2-pyridin-2-ylamino)-pentanoic acid, giving 3-biphenyl-4-yl-3-{-3-indol-2-yl-2-[5-(pyridin-2-ylamino)pentanoylamino]-(2S)-propanoylamino}propionic acid.

Preparative HPLC gives 3-biphenyl-4-yl-3-{-3-indol-2-yl-2-[5-(pyridin-2-ylamino)pentanoylamino]-(2S)-propanoylamino}propionic acid trifluoroacetate, RT 1.303/1.384 min, FAB-MS (M+H)+ 604.4.

Analogously to Example 1, the resin "AB" is reacted with FMOC-protected D-serine and 5-(2-pyridin-2-ylamino)pentanoic acid, giving 3-biphenyl-4-yl-3-{3-hydroxy-2-[5-(pyridin-2-ylamino)pentanoylamino]-(2R)-propanoylamino}propionic acid.

Preparative HPLC gives 3-biphenyl-4-yl-3-{3-hydroxy-2-[5-(pyridin-2-ylamino)pentanoylamino]-(2R)-propanoylamino}propionic acid trifluoroacetate, RT 0.984 min, FAB-MS (M+H)+ 505.2.

Analogously to Example 1, the resin "AB" is reacted with FMOC-protected (2S)-2-aminohexanoic acid and 5-(2-pyridin-2-ylamino)pentanoic acid, giving 3-biphenyl-4-yl-3-{2-[5-(pyridin-2-ylamino)pentanoylamino]-(2S)-hexanoylamino}propionic acid.

Preparative HPLC gives 3-biphenyl-4-yl-3-{2-[5-(pyridin-2-ylamino)pentanoylamino]-(2S)-hexanoylamino}propionic acid trifluoroacetate, RT 1.239/1.351 min, FAB-MS (M+H)+ 531.2.

Analogously to Example 1, the resin "AB" is reacted with FMOC-protected (2R)-2-aminohexanoic acid and 5-(2-pyridin-2-ylamino)pentanoic acid, giving 3-biphenyl-4-yl-3-{2-[5-(pyridin-2-ylamino)pentanoylamino]-(2R)-hexanoylamino}propionic acid.

Preparative HPLC gives 3-biphenyl-4-yl-3-{2-[5-(pyridin-2-ylamino)-pentanoylamino]-(2R)-hexanoylamino}propionic acid trifluoroacetate, RT 1.241/1.354 min, FAB-MS (M+H)+ 531.2.

Analogously to Example 1, the resin "AB" is reacted with FMOC-protected S-trityl-L-cysteine and 5-(2-pyridin-2-ylamino)pentanoic acid, giving 3-biphenyl-4-yl-3-{2-[5-(pyridin-2-ylamino)pentanoylamino]-3-tritylsulfanyl-(2S)-propanoylamino}propionic acid.

Preparative HPLC gives 3-biphenyl-4-yl-3-{2-[5-(pyridin-2-ylamino)-pentanoylamino]-3-tritylsulfanyl-(2S)-propanoylamino}propionic acid trifluoroacetate, RT 1.841/1.901 min, FAB-MS (M+H)+ 764.2.

Analogously to Example 1, the resin "AB" is reacted with FMOC-protected S-trityl-D-cysteine and 5-(2-pyridin-2-ylamino)pentanoic acid, giving 3-biphenyl-4-yl-3-{2-[5-(pyridin-2-ylamino)pentanoylamino]-3-tritylsulfanyl-(2R)-propanoylamino}propionic acid.

Preparative HPLC gives 3-biphenyl-4-yl-3-{2-[5-(pyridin-2-ylamino)-pentanoylamino]-3-tritylsulfanyl-(2R)-propanoylamino}propionic acid trifluoroacetate, RT 1.827/1.890 min, FAB-MS (M+H)+ 764.2.

Analogously to Example 1, the resin "AB" is reacted with FMOC-protected (R)-2,6-diaminohexanoic acid and 5-(2-pyridin-2-ylamino)pentanoic acid, giving 3-biphenyl-4-yl-3-{6-amino-2-[5-(pyridin-2-ylamino)pentanoylamino]-(2R)-hexanoylamino}propionic acid.

Preparative HPLC gives 3-biphenyl-4-yl-3-{6-amino-2-[5-(pyridin-2-ylamino)pentanoylamino]-(2R)-hexanoylamino}propionic acid trifluoroacetate, RT 0.323 min, FAB-MS (M+H)+ 546.2.

Analogously to Example 1, the resin "AB" is reacted with FMOC-protected L-tyrosine and 5-(2-pyridin-2-ylamino)pentanoic acid, giving 3-biphenyl-4-yl-3-{3-(4-hydroxyphenyl)-2-[5-(pyridin-2-ylamino)pentanoylamino]-(2S)-propanoylamino}propionic acid.

Preparative HPLC gives 3-biphenyl-4-yl-3-{3-(4-hydroxyphenyl)-2-[5-(pyridin-2-ylamino)pentanoylamino]-(2S)-propanoylamino}propionic acid trifluoroacetate, RT 1.138/ 1.197 min, FAB-MS (M+H)+ 581.3.

Analogously to Example 1, the resin "AB" is reacted with FMOC-protected (2S)-2,5-diaminopentanoic acid and 5-(2-pyridin-2-ylamino)pentanoic acid, giving 3-biphenyl-4-yl-3-{5-amino-2-[5-(pyridin-2-ylamino)pentanoylamino]-(2S)-pentanoylamino}propionic acid.

Preparative HPLC gives 3-biphenyl-4-yl-3{5-amino-2-[5-(pyridin-2-ylamino) pentanoylamino]-(2S)-pentanoylamino}propionic acid trifluoroacetate, RT 0.553 min, FAB-MS (M+H)+ 566.7/532.2.

Analogously to Example 1, the resin "AB" is reacted with FMOC-protected (2R)-2-amino-3,3-dimethylbutanoic acid and 5-(2-pyridin-2-ylamino)-pentanoic acid, giving 3-biphenyl-4-yl-3-{3,3-dimethyl-2-[5-(pyridin-2-ylamino)pentanoylamino]-(2R)-butanoylamino}propionic acid.

Preparative HPLC gives 3-biphenyl-4-yl-3-{3,3-dimethyl-2-[5-(pyridin-2-ylamino)pentanoylamino]-(2R)-butanoylamino}propionic acid trifluoroacetate, RT 1.160/ 1.334 min, FAB-MS (M+H)+ 531.3.

Analogously to Example 1, the resin "AB" is reacted with FMOC-protected (2R)-2-amino-2-phenylacetic acid and 5-(2-pyridin-2-ylamino)pentanoic acid, giving 3-biphenyl-4-yl-3-{2-phenyl-2-[5-(pyridin-2-ylamino)pentanoylamino]-(2R)-ethanoylamino}propionic acid.

Preparative HPLC gives 3-biphenyl-4-yl-3-{2-phenyl-2-[5-(pyridin-2-ylamino)pentanoylamino]-(2R)-ethanoylamino}propionic acid trifluoroacetate, RT 1.274/ 1.344 min, FAB-MS (M+H)+ 551.2.

Analogously to Example 1, the resin "AB" is reacted with FMOC-protected D-threonine and 5-(2-pyridin-2-ylamino)pentanoic acid, giving 3-biphenyl-4-yl-3-{3-hydroxy-2-[5-(pyridin-2-ylamino)pentanoylamino]-(2R)-butanoylamino}propionic acid.

Preparative HPLC gives 3-biphenyl-4-yl-3-{3-hydroxy-2-[5-(pyridin-2-ylamino)pentanoylamino]-(2R)-butanoylamino}propionic acid trifluoroacetate, RT 0.987/ 1.038 min, FAB-MS (M+H)+ 519.3.

Analogously to Example 1, the resin "AB" is reacted with FMOC-protected D-glutamic acid and 5-(2-pyridin-2-ylamino)pentanoic acid, giving 3-biphenyl-4-yl-3-{4-carboxy-2-[5-(pyridin-2-ylamino)pentanoylamino]-(2R)-butanoylamino}propionic acid.

Preparative HPLC gives 3-biphenyl-4-yl-3-{4-carboxy-2-[5-(pyridin-2-ylamino)-pentanoylamino]-(2R)-butanoylamino}propionic acid trifluoroacetate, RT 1.044 min, FAB-MS (M+H)+ 547.2.

Analogously to Example 1, the resin "AB" is reacted with FMOC-protected L-alanine and 5-(2-pyridin-2-ylamino)pentanoic acid, giving 3-biphenyl-4-yl-3-{2-[5-(pyridin-2-ylamino)pentanoylamino]-(2S)-propanoylamino}propionic acid.

Preparative HPLC gives 3-biphenyl-4-yl-3{2-[5-(pyridin-2-ylamino)-pentanoylamino]-(2S)-propanoylamino}propionic acid trifluoroacetate, RT 1.052/ 1.104 min, FAB-MS (M+H)+ 489.2.

Analogously to Example 1, the resin "AB" is reacted with FMOC-protected D-alanine and 5-(2-pyridin-2-ylamino) pentanoic acid, giving 3-biphenyl-4-yl-3-{2-[5-(pyridin-2-ylamino)pentanoylamino]-(2R)-propanoylamino}propionic acid.

Preparative HPLC gives 3-biphenyl-4-yl-3-{2-[5-(pyridin-2-ylamino)-pentanoylamino]-(2R)-propanoylamino}propionic acid trifluoroacetate, RT 1.007/ 1.068 min, FAB-MS (M+H)+ 489.2.

Analogously to Example 1, the resin "AB" is reacted with FMOC-protected L-methionine and 5-(2-pyridin-2-ylamino) pentanoic acid, giving 3-biphenyl-4-yl-3-{4-methylsulfanyl-2-[5-(pyridin-2-ylamino)pentanoylamino]-(2S)-butanoylamino}propionic acid.

Preparative HPLC gives 3-biphenyl-4-yl-3-{4-methylsulfanyl-2-[5-(pyridin-2-ylamino)pentanoylamino]-(2S)-butanoylamino}propionic acid trifluoroacetate, RT 1.151/ 1.261 min, FAB-MS (M+H)+ 549.2.

Analogously to Example 1, the resin "AB" is reacted with FMOC-protected D-methionine and 5-(2-pyridin-2-ylamino) pentanoic acid, giving 3-biphenyl-4-yl-3-{4-methylsulfanyl-2-[5-(pyridin-2-ylamino)pentanoylamino]-(2R)-butanoylamino}propionic acid.

Preparative HPLC gives 3-biphenyl-4-yl-3-{4-methylsulfanyl-2-[5-(pyridin-2-ylamino)pentanoylamino]-(2R)-butanoylamino}propionic acid trifluoroacetate, RT 1.163/ 1.272 min, FAB-MS (M+H)+ 549.2.

Analogously to Example 1, the resin "AB" is reacted with FMOC-protected (2S)-2-amino-3-methylbutanoic acid and 5-(2-pyridin-2-ylamino)pentanoic acid, giving 3-biphenyl-4-yl-3-{3-methyl-2-[5-(pyridin-2-ylamino)pentanoylamino]-(2S)-butanoylamino}propionic acid.

Preparative HPLC gives 3-biphenyl-4-yl-3-{3-methyl-2-[5-(pyridin-2-ylamino)pentanoylamino]-(2S)-butanoylamino}propionic acid trifluoroacetate, RT 1.148/ 1.280 min, FAB-MS (M+H)+ 517.4.

Analogously to Example 1, the resin "AB" is reacted with FMOC-protected (2R)-2-amino-3-methylbutanoic acid and 5-(2-pyridin-2-ylamino)pentanoic acid, giving 3-biphenyl-4-yl-3-{3-methyl-2-[5-(pyridin-2-ylamino)pentanoylamino]-(2R)-butanoylamino}propionic acid.

Preparative HPLC gives 3-biphenyl-4-yl-3-{3-methyl-2-[5-(pyridin-2-ylamino)pentanoylamino]-(2R)-butanoylamino}propionic acid trifluoroacetate, RT 1.248/ 1.278 min, FAB-MS (M+H)+ 517.2.

Analogously to Example 1, the resin "AB" is reacted with FMOC-protected (2S)-2-amino-4-methylpentanoic acid and 5-(2-pyridin-2-ylamino)pentanoic acid, giving 3-biphenyl-4-yl-3-{4-methyl-2-[5-(pyridin-2-ylamino)pentanoylamino]-(2S)-pentanoylamino}propionic acid.

Preparative HPLC gives 3-biphenyl-4-yl-3-{4-methyl-2-[5-(pyridin-2-ylamino)pentanoylamino]-(2S)-pentanoylamino}propionic acid trifluoroacetate, RT 1.225/ 1.351 min, FAB-MS (M+H)+ 531.4.

Analogously to Example 1, the resin "AB" is reacted with FMOC-protected (2R)-2-amino-4-methylpentanoic acid and 5-(2-pyridin-2-ylamino)pentanoic acid, giving 3-biphenyl-4-yl-3-{4-methyl-2-[5-(pyridin-2-ylamino)pentanoylamino]-(2R)-pentanoylamino}propionic acid.

Preparative HPLC gives 3-biphenyl-4-yl-3-{4-methyl-2-[5-(pyridin-2-ylamino)pentanoylamino]-(2R)-pentanoylamino}propionic acid trifluoroacetate, RT 1.210/ 1.337 min, FAB-MS (M+H)+ 531.3.

Analogously to Example 1, the resin "AB" is reacted with FMOC-protected L-aspartic acid and 5-(2-pyridin-2-ylamino)pentanoic acid, giving 3-biphenyl-4-yl-3-{3-carboxy-2-[5-(pyridin-2-ylamino)pentanoylamino]-(2S)-propanoylamino}propionic acid.

Preparative HPLC gives 3-biphenyl-4-yl-3-{3-carboxy-2-[5-(pyridin-2-ylamino)pentanoylamino]-(2S)-propanoylamino}propionic acid trifluoroacetate, RT 1.044 min, FAB-MS (M+H)+ 533.2.

Analogously to Example 1, the resin "AB" is reacted with FMOC-protected D-aspartic acid and 5-(2-pyridin-2-ylamino)pentanoic acid, giving 3-biphenyl-4-yl-3-{3-carboxy-2-[5-(pyridin-2-ylamino)pentanoylamino]-(2R)-propanoylamino}propionic acid.

Preparative HPLC gives 3-biphenyl-4-yl-3-{3-carboxy-2-[5-(pyridin-2-ylamino)pentanoylamino]-(2R)-propanoylamino}propionic acid trifluoroacetate, RT 1.033 min, FAB-MS (M+H)+ 533.2 (EMD 388500)

Analogously to Example 1, the resin "AB" is reacted with FMOC-protected (2R)-2-amino-3-cyclohexylpropanoic acid and 5-(2-pyridin-2-ylamino)-pentanoic acid, giving 3-biphenyl-4-yl-3-{3-cyclohexyl-2-[5-(pyridin-2-ylamino)pentanoylamino]-(2R)-propanoylamino}propionic acid.

Preparative HPLC gives 3-biphenyl-4-yl-3-{3-cylohexyl-2-[5-(pyridin-2-ylamino)pentanoylamino]-(2R)-propanoylamino}propionic acid trifluoroacetate, RT 1.393/1.512 min, FAB-MS (M+H)+ 571.4.

Analogously to Example 1, the resin "AB" is reacted with FMOC-protected L-glutamic acid and 5-(2-pyridin-2-ylamino)pentanoic acid, giving 3-biphenyl-4-yl-3-{4-carboxy-2-[5-(pyridin-2-ylamino)pentanoylamino]-(2S)-butanoylamino}propionic acid.

Preparative HPLC gives 3-biphenyl-4-yl-3-{4-carboxy-2-[5-(pyridin-2-ylamino)pentanoylamino]-(2S)-butanoylamino}propionic acid trifluoroacetate, RT 1.068 min, FAB-MS (M+H)+ 547.2.

Analogously to Example 1, the resin "AB" is reacted with FMOC-protected (2S)-2-amino-3-phenylpropionic acid and 5-(2-pyridin-2-ylamino)pentanoic acid, giving 3-biphenyl-4-yl-3-{3-phenyl-2-[5-(pyridin-2-ylamino)pentanoylamino]-(2S)-propanoylamino}propionic acid.

Preparative HPLC gives 3-biphenyl-4-yl-3-{3-phenyl-2-[5-(pyridin-2-ylamino)pentanoylamino]-(2S)-propanoylamino}propionic acid trifluoroacetate, RT 1.299/1.413 min, FAB-MS (M+H)+ 565.4.

Analogously to Example 1, the resin "AB" is reacted with FMOC-protected (2R)-2-amino-3-phenylpropionic acid and 5-(2-pyridin-2-ylamino)pentanoic acid, giving 3-biphenyl-4-yl-3-{3-phenyl-2-[5-(pyridin-2-ylamino)pentanoylamino]-(2R)-propanoylamino}propionic acid.

Preparative HPLC gives 3-biphenyl-4-yl-3-{3-phenyl-2-[5-(pyridin-2-ylamino)pentanoylamino]-(2R)-propanoylamino}propionic acid trifluoroacetate, RT 1.299/1.418 min, FAB-MS (M+H)+ 565.4.

Analogously to Example 1, the resin "AB" is reacted with FMOC-protected L-threonine and 5-(2-pyridin-2-ylamino)pentanoic acid, giving 3-biphenyl-4-yl-3-{3-hydroxy-2-[5-(pyridin-2-ylamino)pentanoylamino]-(2S)-butanoylamino}propionic acid.

Preparative HPLC gives 3-biphenyl-4-yl-3-{3-hydroxy-2-[5-(pyridin-2-ylamino)pentanoylamino]-(2S)-butanoylamino}propionic acid trifluoroacetate, RT 1.005/1.054 min, FAB-MS (M+H)+ 519.3.

Analogously to Example 1, the resin "AB" is reacted with FMOC-protected D-tyrosine and 5-(2-pyridin-2-ylamino)pentanoic acid, giving 3-biphenyl-4-yl-3-{4-hydroxyphenyl-2-[5-(pyridin-2-ylamino)pentanoylamino]-(2R)-propanoylamino}propionic acid.

Preparative HPLC gives 3-biphenyl-4-yl-3-{4-hydroxyphenyl-2-[5-(pyridin-2-ylamino)pentanoylamino]-(2R)-propanoylamino}propionic acid trifluoroacetate, RT 1.172/1.230 min, FAB-MS (M+H)+ 581.2.

Analogously to Example 1, the resin "AB" is reacted with FMOC-protected (2S)-2-aminobutanoic acid and 5-(2-pyridin-2-ylamino)pentanoic acid, giving 3-biphenyl-4-yl-3-{2-[5-(pyridin-2-ylamino)pentanoylamino]-(2S)-butanoylamino}propionic acid.

Preparative HPLC gives 3-biphenyl-4-yl-3-{2-[5-(pyridin-2-ylamino)-pentanoylamino]-(2S)-butanoylamino}propionic acid trifluoroacetate, RT 1.103/1.187 min, FAB-MS (M+H)+ 503.2.

Analogously to Example 1, the resin "AB" is reacted with FMOC-protected 2-amino-2-methylpropanoic acid and 5-(2-pyridin-2-ylamino)pentanoic acid, giving 3-biphenyl-4-yl-3-{2-methyl-2-[5-(pyridin-2-ylamino)pentanoylamino]propanoylamino}propionic acid.

Preparative HPLC gives 3-biphenyl-4-yl-3-{2-methyl-2-[5-(pyridin-2-ylamino)pentanoylamino]propanoylamino}propionic acid trifluoroacetate, RT 1.007/1.116 min, FAB-MS (M+H)+ 503.2.

Analogously to Example 1, the resin "AB" is reacted with FMOC-protected L-serine and 5-(2-pyridin-2-ylamino)pentanoic acid, giving 3-biphenyl-4-yl-3-{3-hydroxy-2-[5-(pyridin-2-ylamino)pentanoylamino]-(2S)-propanoylamino}propionic acid.

Preparative HPLC gives 3-biphenyl-4-yl-3-{3-hydroxy-2-[5-(pyridin-2-ylamino)pentanoylamino]-(2S)-propanoylamino}propionic acid trifluoroacetate, RT 1.028 min, FAB-MS (M+H)+ 505.2.

Analogously to Example 1, the resin "AB" is reacted with FMOC-protected (2S)-2-amino-2-phenylethanoic acid and 5-(2-pyridin-2-ylamino)pentanoic acid, giving 3-biphenyl-4-yl-3-{2-phenyl-2-[5-(pyridin-2-ylamino)pentanoylamino]-(2S)-ethanoylamino}propionic acid.

Preparative HPLC gives 3-biphenyl-4-yl-3-{2-phenyl-2-[5-(pyridin-2-ylamino)pentanoylamino]-(2S)-ethanoylamino}propionic acid trifluoroacetate, RT 1.274/1.377 min, FAB-MS (M+H)+ 551.2.

Analogously to Example 1, the resin "AB" is reacted with FMOC-protected (2R)-2-amino-3-thiophen-2-ylpropanoic acid and 5-(2-pyridin-2-ylamino)-pentanoic acid, giving 3-biphenyl-4-yl-3-{3-thiophen-2-[5-(pyridin-2-ylamino)pentanoylamino]-(2R)-propanoylamino}propionic acid.

Preparative HPLC gives 3-biphenyl-4-yl-3-{3-thiophen-2-[5-(pyridin-2-ylamino)pentanoylamino]-(2R)-propanoylamino}propionic acid trifluoroacetate, RT 1.291/1.404 min, FAB-MS (M+H)+ 571.2.

Analogously to Example 1, the resin "AB" is reacted with FMOC-protected D-glutamine and 5-(2-pyridin-2-ylamino)pentanoic acid, giving 3-biphenyl-4-yl-3-{4-carbamoyl-2-[5-(pyridin-2-ylamino)pentanoylamino]-(2R)-butanoylamino}propionic acid.

Preparative HPLC gives 3-biphenyl-4-yl-3-{4-carbamoyl-2-[5-(pyridin-2-ylamino)pentanoylamino]-(2R)-butanoylamino}propionic acid trifluoroacetate, RT 0.983 min, FAB-MS (M+H)+ 546;3.

Analogously to Example 1, the resin "AB" is reacted with FMOC-protected (2S)-2-amino-2-phenylethanoic acid and 4-(2-pyridin-2-ylamino)butanoic acid, giving 3-biphenyl-4-yl-3-{2-phenyl-2-[4-(pyridin-2-ylamino)butanoylamino]-(2S)-ethanoylamino}propionic acid.

Preparative HPLC gives 3-biphenyl-4-yl-3-{2-phenyl-2-[4-(pyridin-2-ylamino)butanoylamino]-(2S)-ethanoylamino}propionic acid trifluoroacetate, RT 1.231/1.340 min, FAB-MS (M+H)+ 537.2.

Analogously to Example 1, the resin "AB" is reacted with FMOC-protected (2R)-2-amino-3-thiophen-2-ylpropanoic acid and 4-(2-pyridin-2-ylamino)-butanoic acid, giving 3-biphenyl-4-yl-3-{3-thiophen-2-[4-(pyridin-2-ylamino)-butanoylamino]-(2R)-propanoylamino}propionic acid.

Preparative HPLC gives 3-biphenyl-4-yl-3-{3-thiophen-2-[4-(pyridin-2-ylamino)butanoylamino]-(2R)-propanoylamino}propionic acid trifluoroacetate, RT 1.266/1.389 min, FAB-MS (M+H)+ 557.2.

Analogously to Example 1, the resin "AB" is reacted with FMOC-protected D-glutamine and 4-(2-pyridin-2-ylamino)

butanoic acid, giving 3-biphenyl-4-yl-3-{4-carbamoyl-2-[4-(pyridin-2-ylamino)butanoylamino]-(2R)-butanoylamino}propionic acid.

Preparative HPLC gives 3-biphenyl-4-yl-3-{4-carbamoyl-2-[4-(pyridin-2-ylamino)butanoylamino]-(2R)-butanoylamino}propionic acid trifluoroacetate, RT 1.012 min, FAB-MS (M+H)$^+$ 532.2.

Analogously to Example 1, the resin "AB" is reacted with FMOC-protected (2S)-2,6-diaminohexanoic acid and 5-(2-pyridin-2-ylamino)pentanoic acid, giving 3-biphenyl-4-yl-3-{6-amino-2-[5-(pyridin-2-ylamino)pentanoylamino]-(2S)-hexanoylamino}propionic acid.

Preparative HPLC gives 3-biphenyl-4-yl-3-{6-amino-2-[5-(pyridin-2-ylamino)pentanoylamino]-(2S)-hexanoylamino}propionic acid trifluoroacetate, RT 0.334 min, FAB-MS (M+H)$^+$ 546.2.

Analogously to Example 1, the resin "AB" is reacted with FMOC-protected S-tert-butyl-L-cysteine and 5-(2-pyridin-2-ylamino)pentanoic acid, giving 3-biphenyl-4-yl-3-{3-tert-butylsulfanyl-2-[5-(pyridin-2-ylamino)pentanoylamino]-(2S)-propanoylamino}propionic acid.

Preparative HPLC gives 3-biphenyl-4-yl-3-{3-tert-butylsulfanyl-2-[5-(pyridin-2-ylamino)pentanoylamino]-(2S)-propanoylamino}propionic acid trifluoroacetate, RT 1.323/1.444 min, FAB-MS (M+H)$^+$ 577.4.

Analogously to Example 1, the resin "AB" is reacted with FMOC-protected (2S)-2-amino-3-(tert-butphenylethanoic)propanoic acid and 5-(2-pyridin-2-ylamino)pentanoic acid, giving 3-biphenyl-4-yl-3-{3-tert-butphenylethanoic-2-[5-(pyridin-2-ylamino)pentanoylamino]-(2S)-propanoylamino}propionic acid.

Preparative HPLC gives 3-biphenyl-4-yl-3-{3-tert-butphenylethanoic-2-[5-(pyridin-2-ylamino)pentanoylamino]-(2S)-propanoylamino}propionic acid trifluoroacetate, RT 1.520/1.636 min, FAB-MS (M+H)$^+$ 577.4.

Analogously to Example 1, the resin "AB" is reacted with FMOC-protected S-benzyl-L-cysteine and 5-(2-pyridin-2-ylamino)pentanoic acid, giving 3-biphenyl-4-yl-3-{3-(benzylsulfanyl)-2-[5-(pyridin-2-ylamino)pentanoylamino]-(2S)-propanoylamino}propionic acid.

Preparative HPLC gives 3-biphenyl-4-yl-3-{3-(benzylsulfanyl)-2-[5-(pyridin-2-ylamino)pentanoylamino]-(2S)-propanoylamino}propionic acid trifluoroacetate, RT 1.467/1.583 min, FAB-MS (M+H)$^+$ 611.4.

Analogously to Example 1, the resin "AB" is reacted with FMOC-protected (2S)-2-amino-3-(acetylaminomethylsulfanyl)propanoic acid and 5-(2-pyridin-2-ylamino)pentanoic acid, giving 3-biphenyl-4-yl-3-{3-(acetylaminomethylsulfanyl)-2-[5-(pyridin-2-ylamino)pentanoylamino]-(2S)-propanoylamino}propionic acid.

Preparative HPLC gives 3-biphenyl-4-yl-3-{3-(acetylaminomethylsulfanyl)-2-[5-(pyridin-2-ylamino)pentanoylamino]-(2S)-propanoylamino}propionic acid trifluoroacetate, RT 1.110 min, FAB-MS (M+H)$^+$ 691.7.

Analogously to Example 1, the resin "AB" is reacted with FMOC-protected S-diphenylmethyl-L-cysteine and 5-(2-pyridin-2-ylamino)pentanoic acid, giving 3-biphenyl-4-yl-3-{3-(diphenylmethylsulfanyl)-2-[5-(pyridin-2-ylamino)pentanoylamino]-(2S)-propanoylamino}propionic acid.

Preparative HPLC gives 3-biphenyl-4-yl-3-{3-(diphenylmethylsulfanyl)-2-[5-(pyridin-2-ylamino)pentanoylamino]-(2S)-propanoylamino}propionic acid trifluoroacetate, RT 1.697/1.788 min, FAB-MS (M+H)$^+$ 687.4.

Analogously to Example 1, the resin "AB" is reacted with FMOC-protected S-methyl-L-cysteine and 5-(2-pyridin-2-ylamino)pentanoic acid, giving 3-biphenyl-4-yl-3-{3-(methylsulfanyl)-2-[5-(pyridin-2-ylamino)pentanoylamino]-(2S)-propanoylamino}propionic acid.

Preparative HPLC gives 3-biphenyl-4-yl-3-{3-(methylsulfanyl)-2-[5-(pyridin-2-ylamino)pentanoylamino]-(2S)-propanoylamino}propionic acid trifluoroacetate, RT 1.184/1.289 min, FAB-MS (M+H)$^+$ 635.3.

Analogously to Example 1, the resin "AB" is reacted with FMOC-protected (2S)-2-amino-4-tritylbutanoic acid and 5-(2-pyridin-2-ylamino)pentanoic acid, giving 3-biphenyl-4-yl-3-{4-trityl-2-[5-(pyridin-2-ylamino)pentanoylamino]-(2S)-butanoylamino}propionic acid.

Preparative HPLC gives 3-biphenyl-4-yl-3-{4-trityl-2-[5-(pyridin-2-ylamino)-pentanoylamino]-(2S)-butanoylamino}propionic acid trifluoroacetate, RT 1.843 min, FAB-MS (M+H)$^+$ 745.4.

Analogously to Example 1, the resin "AB" is reacted with FMOC-protected (2S)-2-amino-6-tritylhexanoic acid and 5-(2-pyridin-2-ylamino)pentanoic acid, giving 3-biphenyl-4-yl-3-{6-trityl-2-[5-(pyridin-2-ylamino)pentanoylamino]-(2S)-hexanoylamino}propionic acid.

Preparative HPLC gives 3-biphenyl-4-yl-3-{6-trityl-2-[5-(pyridin-2-ylamino)-pentanoylamino]-(2S)-hexanoylamino}propionic acid trifluoroacetate, RT 1.973/2.005 min, FAB-MS (M+H)$^+$ 773.4.

Analogously to Example 1, the resin "AB" is reacted with FMOC-protected S-ethyl-L-cysteine and 5-(2-pyridin-2-ylamino)pentanoic acid, giving 3-biphenyl-4-yl-3-{3-(ethylsulfanyl)-2-[5-(pyridin-2-ylamino)pentanoylamino]-(2S)-propanoylamino}propionic acid.

Preparative HPLC gives 3-biphenyl-4-yl-3-{3-(ethylsulfanyl)-2-[5-(pyridin-2-ylamino)pentanoylamino]-(2S)-propanoylamino}propionic acid trifluoroacetate, RT 1.234/1.344 min, FAB-MS (M+H)$^+$ 549.4.

Analogously to Example 1, the resin "AB" is reacted with FMOC-protected (2R)-2-amino-4-hydroxybutanoic acid and 5-(2-pyridin-2-ylamino)pentanoic acid, giving 3-biphenyl-4-yl-3-{4-hydroxy-2-[5-(pyridin-2-ylamino)pentanoylamino]-(2R)-butanoylamino}propionic acid.

Preparative HPLC gives 3-biphenyl-4-yl-3-{4-hydroxy-2-[5-(pyridin-2-ylamino)pentanoylamino]-(2R)-butanoylamino}propionic acid trifluoroacetate, RT 1.017 min, FAB-MS (M+H)$^+$ 519.3.

Analogously to Example 1, the resin "AB" is reacted with FMOC-protected (2R)-2-amino-4-hydroxybutanoic acid and 4-(2-pyridin-2-ylamino)butanoic acid, giving 3-biphenyl-4-yl-3-{4-hydroxy-2-[4-(pyridin-2-ylamino)butanoylamino]-(2R)-butanoylamino}propionic acid.

Preparative HPLC gives 3-biphenyl-4-yl-3-{4-hydroxy-2-[4-(pyridin-2-ylamino)butanoylamino]-(2R)-butanoylamino}propionic acid trifluoroacetate, RT 1 min, FAB-MS (M+H)$^+$ 505.2.

Analogously to Example 1, the resin "AB" is reacted with FMOC-protected (2S)-2-amino-4-(tritylsulfanyl)butanoic acid and 4-(2-pyridin-2-ylamino)-butanoic acid, giving 3-biphenyl-4-yl-3-{2-[4-(pyridin-2-ylamino)-butanoylamino]-4-tritylsulfanyl-(2S)-butanoylamino}propionic acid.

Preparative HPLC gives 3-biphenyl-4-yl-3-{2-[4-(pyridin-2-ylamino)butanoylamino]-4-tritylsulfanyl-(2S)-butanoylamino}propionic acid trifluoroacetate, RT 2.130 min, FAB-MS (M+H)$^+$ 763.6.

Analogously to Example 1, the resin "AB" is reacted with FMOC-protected (2S)-2-amino-4-methoxybutanoic acid and 4-(2-pyridin-2-ylamino)butanoic acid, giving 3-biphenyl-4-yl-3-{4-methoxy-2-[4-(pyridin-2-ylamino)butanoylamino]-(2S)-butanoylamino}propionic acid.

Preparative HPLC gives 3-biphenyl-4-yl-3-{4-methoxy-2-[4-(pyridin-2-ylamino)butanoylamino]-(2S)- butanoylamino}propionic acid trifluoroacetate, RT 1.188/ 1.256 min, FAB-MS (M+H)+ 519.2.

Analogously to Example 1, the resin "AB" is reacted with FMOC-protected (2S)-2-amino-4-methanesulfinylbutanoic acid and 4-(2-pyridin-2-ylamino)-butanoic acid, giving 3-biphenyl-4-yl-3-{4-methanesulfinyl-2-[4-(pyridin-2-ylamino) butanoylamino]-(2S)-butanoylamino}propionic acid.

Preparative HPLC gives 3-biphenyl-4-yl-3-{4-methanesulfinyl-2-[4-(pyridin-2-ylamino)butanoylamino]-(2S)-butanoylamino}propionic acid trifluoroacetate, RT 1.103 min, FAB-MS (M+H)+ 551.2.

Analogously to Example 1, the resin "AB" is reacted with FMOC-protected (2S)-2-amino-4-methanesulfonylbutanoic acid and 4-(2-pyridin-2-ylamino)-butanoic acid, giving 3-biphenyl-4-yl-3-{4-methanesulfonyl-2-[4-(pyridin-2-ylamino)butanoylamino]-(2S)-butanoylamino}propionic acid.

Preparative HPLC gives 3-biphenyl-4-yl-3-{4-methanesulfonyl-2-[4-(pyridin-2-ylamino)butanoylamino]-(2S)-butanoylamino}propionic acid trifluoroacetate, RT 1.195 min, FAB-MS (M+H)+ 567.2.

Analogously to Example 1, the resin "AB" is reacted with FMOC-protected (2S)-2-amino-3-benzyloxypropanoic acid and 4-(2-pyridin-2-ylamino)-butanoic acid, giving 3-biphenyl-4-yl-3-{3-benzyloxy-2-[4-(pyridin-2-ylamino)butanoylamino]-(2S)-propanoylamino}propionic acid.

Preparative HPLC gives 3-biphenyl-4-yl-3-{3-benzyloxy-2-[4-(pyridin-2-ylamino)butanoylamino]-(2S)-propanoylamino}propionic acid trifluoroacetate, RT 1.509 min, FAB-MS (M+H)+ 581.2.

Analogously to Example 1, the resin "AB" is reacted with FMOC-protected (2S)-2-amino-6-ureidohexanoic acid and 4-(2-pyridin-2-ylamino)butanoic acid, giving 3-biphenyl-4-yl-3-{6-ureido-2-[4-(pyridin-2-ylamino)butanoylamino]-(2S)-hexanoylamino}propionic acid.

Preparative HPLC gives 3-biphenyl-4-yl-3-{6-ureido-2-[4-(pyridin-2-ylamino)butanoylamino]-(2S)-hexanoylamino}propionic acid trifluoroacetate, RT 1.116 min, FAB-MS (M+H)+ 575.2.

Analogously to Example 1, the resin "AB" is reacted with FMOC-protected (2S)-2-amino-6-benzyloxycarbonylaminohexanoic acid and 4-(2-pyridin-2-ylamino)butanoic acid, giving 3-biphenyl-4-yl-3-{6-benzyloxycarbonylamino-2-[4-(pyridin-2-ylamino)butanoylamino]-(2S)-hexanoylamino}propionic acid.

Preparative HPLC gives 3-biphenyl-4-yl-3-{6-benzyloxycarbonylamino-2-[4-(pyridin-2-ylamino)butanoylamino]-(2S)-hexanoylamino}propionic acid trifluoroacetate, RT 1.568 min, FAB-MS (M+H)+ 666.4.

Analogously to Example 1, the resin "AB" is reacted with FMOC-protected (2S)-2-amino-6-acetylaminohexanoic acid and 4-(2-pyridin-2-ylamino)-butanoic acid, giving 3-biphenyl-4-yl-3-{6-acetylamino-2-[4-(pyridin-2-ylamino)butanoylamino]-(2S)-hexanoylamino}propionic acid.

Preparative HPLC gives 3-biphenyl-4-yl-3-{6-acetylamino-2-[4-(pyridin-2-ylamino)butanoylamino]-(2S)-hexanoylamino}propionic acid trifluoroacetate, RT 1.146 min, FAB-MS (M+H)+ 574.3.

Analogously to Example 1, the resin "AB" is reacted with FMOC-protected (2S)-2-amino-6-allyloxycarbonylaminohexanoic acid and 4-(2-pyridin-2-ylamino)butanoic acid, giving 3-biphenyl-4-yl-3-{6-allyloxycarbonylamino-2-[4-(pyridin-2-ylamino)butanoylamino]-(2S)-hexanoylamino}propionic acid.

Preparative HPLC gives 3-biphenyl-4-yl-3-{6-allyloxycarbonylamino-2-[4-(pyridin-2-ylamino)butanoylamino]-(2S)-hexanoylamino}propionic acid trifluoroacetate, RT 1.383 min, FAB-MS (M+H)+ 616.3.

Analogously to Example 1, the resin "AB" is reacted with FMOC-protected (2S)-2-amino-4-tritylsulfanylbutanoic acid and 5-(2-pyridin-2-ylamino)-pentanoic acid, giving 3-biphenyl-4-yl-3-{4-tritylsulfanyl-2-[5-(pyridin-2-ylamino)pentanoylamino]-(2S)-butanoylamino}propionic acid.

Preparative HPLC gives 3-biphenyl-4-yl-3-{4-tritylsulfanyl-2-[4-(pyridin-2-ylamino)pentanoylamino]-(2S)-butanoylamino}propionic acid trifluoroacetate, RT 2.041/ 2.104 min, FAB-MS (M+H)+ 777.6.

Analogously to Example 1, the resin "AB" is reacted with FMOC-protected (2S)-2-amino-4-methoxybutanoic acid and 5-(2-pyridin-2-ylamino)pentanoic acid, giving 3-biphenyl-4-yl-3-{4-methoxy-2-[5-(pyridin-2-ylamino)pentanoylamino]-(2S)-butanoylamino}propionic acid.

Preparative HPLC gives 3-biphenyl-4-yl-3-{4-methoxy-2-[5-(pyridin-2-ylamino)pentanoylamino]-(2S)-butanoylamino}propionic acid trifluoroacetate, RT 1.199/ 1.269 min, FAB-MS (M+H)+ 533.2.

Analogously to Example 1, the resin "AB" is reacted with FMOC-protected (2S)-2-amino-4-methanesulfinylbutanoic acid and 5-(2-pyridin-2-ylamino)-pentanoic acid, giving 3-biphenyl-4-yl-3-{4-methanesulfinyl-2-[5-(pyridin-2-ylamino)pentanoylamino]-(2S)-butanoylamino}propionic acid.

Preparative HPLC gives 3-biphenyl-4-yl-3-{4-methanesulfinyl-2-[5-(pyridin-2-ylamino)pentanoylamino]-(2S)-butanoylamino}propionic acid trifluoroacetate, RT 1.100 min, FAB-MS (M+H)+ 565.3.

Analogously to Example 1, the resin "AB" is reacted with FMOC-protected (2S)-2-amino-4-methanesulfonylbutanoic acid and 5-(2-pyridin-2-ylamino)-pentanoic acid, giving 3-biphenyl-4-yl-3-{4-methanesulfonyl-2-[5-(pyridin-2-ylamino)pentanoylamino]-(2S)-butanoylamino}propionic acid.

Preparative HPLC gives 3-biphenyl-4-yl-3-{4-methanesulfonyl-2-[5-(pyridin-2-ylamino)pentanoylamino]-(2S)-butanoylamino}propionic acid trifluoroacetate, RT 1.203 min, FAB-MS (M+H)+ 581.3.

Analogously to Example 1, the resin "AB" is reacted with FMOC-protected (2S)-2-amino-3-benzyloxypropanoic acid and 5-(2-pyridin-2-ylamino)-pentanoic acid, giving 3-biphenyl-4-yl-3-{3-benzyloxy-2-[5-(pyridin-2-ylamino)pentanoylamino]-(2S)-propanoylamino}propionic acid.

Preparative HPLC gives 3-biphenyl-4-yl-3-{3-benzyloxy-2-[5-(pyridin-2-ylamino)pentanoylamino]-(2S)-propanoylamino}propionic acid trifluoroacetate, RT 1.510 min, FAB-MS (M+H)+ 595.3.

Analogously to Example 1, the resin "AB" is reacted with FMOC-protected (2S)-2-amino-6-ureidohexanoic acid and 5-(2-pyridin-2-ylamino)pentanoic acid, giving 3-biphenyl-4-yl-3-{6-ureido-2-[5-(pyridin-2-ylamino)pentanoylamino]-(2S)-hexanoylamino}propionic acid.

Preparative HPLC gives 3-biphenyl-4-yl-3-{6-ureido-2-[5-(pyridin-2-ylamino)pentanoylamino]-(2S)-hexanoylamino}propionic acid trifluoroacetate, RT 1.120 min, FAB-MS (M+H)+ 589.3.

Analogously to Example 1, the resin "AB" is reacted with FMOC-protected (2S)-2-amino-6-benzyloxycarbonylaminohexanoic acid and 5-(2-pyridin-2-ylamino)pentanoic acid, giving 3-biphenyl-4-yl-3-{6-benzyloxycarbonylamino-2-[5-(pyridin-2-ylamino)pentanoylamino]-(2S)-hexanoylamino}propionic acid.

Preparative HPLC gives 3-biphenyl-4-yl-3-{6-benzyloxycarbonylamino-2-[5-(pyridin-2-ylamino)pentanoylamino]-

(2S)-hexanoylamino}propionic acid trifluoroacetate, RT 1.564 min, FAB-MS (M+H)⁺ 680.5.

Analogously to Example 1, the resin "AB" is reacted with FMOC-protected (2S)-2-amino-6-acetylaminohexanoic acid and 5-(2-pyridin-2-ylamino)-pentanoic acid, giving 3-biphenyl-4-yl-3-{6-acetylamino-2-[5-(pyridin-2-ylamino)pentanoylamino]-(2S)-hexanoylamino}propionic acid.

Preparative HPLC gives 3-biphenyl-4-yl-3-{6-acetylamino-2-[5-(pyridin-2-ylamino)pentanoylamino]-(2S)-hexanoylamino}propionic acid trifluoroacetate, RT 1.147 min, FAB-MS (M+H)⁺ 588.3.

Analogously to Example 1, the resin "AB" is reacted with FMOC-protected (2S)-2-amino-6-allyloxycarbonylaminohexanoic acid and 5-(2-pyridin-2-ylamino)-pentanoic acid, giving 3-biphenyl-4-yl-3-{6-allyloxycarbonylamino-2-[5-(pyridin-2-ylamino)pentanoylamino]-(2S)-hexanoylamino}propionic acid.

Preparative HPLC gives 3-biphenyl-4-yl-3-{6-allyloxycarbonylamino-2-[5-(pyridin-2-ylamino)pentanoylamino]-(2S)-hexanoylamino}propionic acid trifluoroacetate, RT 1.400 min, FAB-MS (M+H)⁺ 630.3.

Analogously to Example 1, the resin "AB" is reacted with FMOC-protected (2S)-2-amino-4-tritylsulfanylbutanoic acid and 6-(2-pyridin-2-ylamino)-hexanoic acid, giving 3-biphenyl-4-yl-3-{4-tritylsulfanyl-2-[6-(pyridin-2-ylamino)hexanoylamino]-(2S)-butanoylamino}propionic acid.

Preparative HPLC gives 3-biphenyl-4-yl-3-{4-tritylsulfanyl-2-[6-(pyridin-2-ylamino)hexanoylamino]-(2S)-butanoylamino}propionic acid trifluoroacetate, RT 2.089/2.155 min, FAB-MS (M+H)⁺ 791.7.

Analogously to Example 1, the resin "AB" is reacted with FMOC-protected (2S)-2-amino-4-methoxybutanoic acid and 6-(2-pyridin-2-ylamino)-hexanoic acid, giving 3-biphenyl-4-yl-3-{4-methoxy-2-[6-(pyridin-2-ylamino)hexanoylamino]-(2S)-butanoylamino}propionic acid.

Preparative HPLC gives 3-biphenyl-4-yl-3-{4-methoxy-2-[6-(pyridin-2-ylamino)hexanoylamino]-(2S)-butanoylamino}propionic acid trifluoroacetate, RT 1.219/1.288 min, FAB-MS (M+H)⁺ 547.2.

Analogously to Example 1, the resin "AB" is reacted with FMOC-protected (2S)-2-amino-4-methanesulfinylbutanoic acid and 6-(2-pyridin-2-ylamino)-hexanoic acid, giving 3-biphenyl-4-yl-3-{4-methanesulfinyl-2-[6-(pyridin-2-ylamino)hexanoylamino]-(2S)-butanoylamino}propionic acid.

Preparative HPLC gives 3-biphenyl-4-yl-3-{4-methanesulfinyl-2-[6-(pyridin-2-ylamino)hexanoylamino]-(2S)-butanoylamino}propionic acid trifluoroacetate, RT 1.129 min, FAB-MS (M+H)⁺ 588.3.

Analogously to Example 1, the resin "AB" is reacted with FMOC-protected (2S)-2-amino-4-methanesulfonylbutanoic acid and 6-(2-pyridin-2-ylamino)-hexanoic acid, giving 3-biphenyl-4-yl-3-{4-methanesulfonyl-2-[6-(pyridin-2-ylamino)hexanoylamino]-(2S)-butanoylamino}propionic acid.

Preparative HPLC gives 3-biphenyl-4-yl-3-{4-methanesulfonyl-2-[6-(pyridin-2-ylamino)hexanoylamino]-(2S)-butanoylamino}propionic acid trifluoroacetate, RT 1.231 min, FAB-MS (M+H)⁺ 595.3.

Analogously to Example 1, the resin "AB" is reacted with FMOC-protected (2S)-2-amino-3-benzyloxypropanoic acid and 6-(2-pyridin-2-ylamino)-hexanoic acid, giving 3-biphenyl-4-yl-3-{3-benzyloxy-2-[6-(pyridin-2-ylamino)hexanoylamino]-(2S)-propanoylamino}propionic acid.

Preparative HPLC gives 3-biphenyl-4-yl-3-{3-benzyloxy-2-[6-(pyridin-2-ylamino)hexanoylamino]-(2S)-propanoylamino}propionic acid trifluoroacetate, RT 1.531 min, FAB-MS (M+H)⁺ 609.3.

Analogously to Example 1, the resin "AB" is reacted with FMOC-protected (2S)-2-amino-6-ureidohexanoic acid and 6-(2-pyridin-2-ylamino)-hexanoic acid, giving 3-biphenyl-4-yl-3-{6-ureido-2-[6-(pyridin-2-ylamino)hexanoylamino]-(2S)-hexanoylamino}propionic acid.

Preparative HPLC gives 3-biphenyl-4-yl-3-{6-ureido-2-[6-(pyridin-2-ylamino)hexanoylamino]-(2S)-hexanoylamino}propionic acid trifluoroacetate, RT 1.156 min, FAB-MS (M+H)⁺ 603.3.

Analogously to Example 1, the resin "AB" is reacted with FMOC-protected (2S)-2-amino-6-benzyloxycarbonylaminohexanoic acid and 6-(2-pyridin-2-ylamino)hexanoic acid, giving 3-biphenyl-4-yl-3-{6-benzyloxycarbonylamino-2-[6-(pyridin-2-ylamino)hexanoylamino]-(2S)-hexanoylamino}propionic acid.

Preparative HPLC gives 3-biphenyl-4-yl-3-{6-benzyloxycarbonylamino-2-[6-(pyridin-2-ylamino)hexanoylamino]-(2S)-hexanoylamino}propionic acid trifluoroacetate, RT 1.605 min, FAB-MS (M+H)⁺ 693.3.

Analogously to Example 1, the resin "AB" is reacted with FMOC-protected (2S)-2-amino-6-acetylaminohexanoic acid and 6-(2-pyridin-2-ylamino)-hexanoic acid, giving 3-biphenyl-4-yl-3-{6-acetylamino-2-[6-(pyridin-2-ylamino)hexanoylamino]-(2S)-hexanoylamino}propionic acid.

Preparative HPLC gives 3-biphenyl-4-yl-3-{6-acetylamino-2-[6-(pyridin-2-ylamino)hexanoylamino]-(2S)-hexanoylamino}propionic acid trifluoroacetate, RT 1.171 min, FAB-MS (M+H)⁺ 602.3.

Analogously to Example 1, FMOC-protected 3-amino-3-(3-chloro-phenyl)-propanoic acid is firstly converted into resin-bound 3-amino-3-(3-chlorophenyl)propanoic acid, and this is subsequently reacted with FMOC-protected (2S)-2-amino-3-benzyloxypropanoic acid and 5-(2-pyridin-2-ylamino)pentanoic acid, giving 3-{3-benzyloxy-2-[5-(pyridin-2-ylamino)-pentanoylamino]propionylamino}-3-(3-chloro-phenyl)propionic acid.

Preparative HPLC gives 3-{3-benzyloxy-2-[5-(pyridin-2-ylamino)pentanoylamino]propionylamino}-3-(3-chlorophenyl)propionic acid trifluoroacetate, RT 13.92 min (diastereoisomer 1), 14.83 min (diastereoisomer 2), FAB-MS (M+H)⁺ 553.8/554.8/555.8.

Analogously to Example 1, FMOC-protected 3-amino-3-(3-bromo-phenyl)-propanoic acid is firstly converted into resin-bound 3-amino-3-(3-bromophenyl)propanoic acid, and this is subsequently reacted with FMOC-protected 2-amino-3-benzyloxypropanoic acid and 5-(2-pyridin-2-ylamino)-pentanoic acid, giving 3-{3-benzyloxy-2-[5-(pyridin-2-ylamino)pentanoylamino]propionylamino}-3-(3-bromophenyl)propionic acid.

Preparative HPLC gives 3-{3-benzyloxy-2-[5-(pyridin-2-ylamino)pentanoylamino]propionylamino}-3-(3-bromophenyl)propionic acid trifluoroacetate, RT 14.69 min (diastereoisomer 1), 15.63 min (diastereoisomer 2), FAB-MS (M+H)⁺ 597.2/599.2.

Analogously to Example 1, FMOC-protected 3-amino-3-(4-chloro-phenyl)-propanoic acid is firstly converted into resin-bound 3-amino-3-(4-chlorophenyl)propanoic acid, and this is subsequently reacted with FMOC-protected (2S)-2-amino-3-benzyloxypropanoic acid and 5-(2-pyridin-2-ylamino)pentanoic acid, giving 3-{3-benzyloxy-2-[5-(pyridin-2-ylamino)-pentanoylamino]propionylamino}-3-(4-chlorophenyl)propionic acid.

Preparative HPLC gives 3-{3-benzyloxy-2-[5-(pyridin-2-ylamino)pentanoylamino]propionylamino}-3-(4-chlorophenyl)propionic acid trifluoroacetate, RT 14.12 min (diastereoisomer 1), 14.98 min (diastereoisomer 2), FAB-MS (M+H)⁺ 553.8/554.8/555.8.

The examples below relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4.2H_2O$, 28.48 g of $Na_2HPO_4.12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation Spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:

1. Compounds of the formula I in which $R^1$, $R^{1'}$ and $R^{1''}$ are H or phenyl, $R^2$ is A, Ar, $(CH_2)_mXA$, $(CH_2)_mOH$, $(CH_2)_mNH_2$, $(CH_2)_mNHA$, $(CH_2)_mNA_2$, $(CH_2)_mNHCOA$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_mXCOYA$, $(CH_2)_mXCOY$, $(CH_2)_oAr$, $(CH_2)_mX(CH_2)_oYA$, $(CH_2)_mX(CH_2)_oNHCOA$, $(CH_2)_mNHCONHR^{2'}$, $(CH_2)_mCH_2A$, $(CH_2)_mCHA_2$, $(CH_2)_mCA_3$, $(CH_2)_mAr(CH_2)_m$, $CHAr_2(CH_2)_m$, $CAr_3(CH_2)_m$cycloalkyl, $(CH_2)_m$—NH—C(=NH)—$_2$, or $(CH_2)_m$—(HN=)C—NH$_2$, where X and Y, independently of one another, are S, O, S=O, SO$_2$ or NH, where, if $R^2$=(CH$_2$)$_m$XCOYA or (CH$_2$)$_m$XCOY(CH$_2$)$_o$Ar, X and Y cannot be S=O or SO$_2$, $R^{2'}$ is H or A, $R^3$ is Het$^2$-NH—, where the primary amino group is optionally provided with an amino-protecting group, A is alkyl having from 1 to 8 carbon atoms, Ar is phenyl, naphthyl, anthranyl or biphenyl, each of which is unsubstituted or monosubstituted or polysubstituted by Hal, A, OA, OH, CO-A, CN, COOA, COOH, CONH$_2$, CONHA, CONA$_2$, CF$_3$, OCF$_3$ or NO$_2$, Het$^2$ is pyridyl which is unsubstituted or monosubstituted or disubstituted by NH$_2$ or NHA, Hal F, Cl, Br or iodine, m is 0, 1, 2, 3, 4, 5, 6 or 8, n is 1, 2, 3, 4, 5 or 6, and o is 0, 1, 2 or 3, or a physiologically acceptable salt thereof.

2. A compound, which is
3-biphenyl-4-yl-3-{2-[4-(pyridin-2-ylamino)pentanoylamino]pentanoylamino}propionic acid, 3-biphenyl-4-yl-3-{-2-[4-(pyridin-2-ylamino)butanoy-
lamino]-(2S)-propanoylamino}propionic acid,
3-biphenyl-4-yl-3-{2-[4-(pyridin-2-ylamino)butanoy-
lamino]-(2R)-propanoylamino}propionic acid,
3-biphenyl-4-yl-3-{4-methylsulfanyl-2-[4-(pyridin-2-
ylamino)butanoylamino]-(2S)-
butanoylamino}propionic acid,
3-biphenyl-4-yl-3-{4-methylsulfanyl-2-[4-(pyridin-2-
ylamino)butanoylamino]-(2R)-
butanoylamino}propionic acid,
3-biphenyl-4-yl-3-{3-methyl-2-[4-(pyridin-2-ylamino)-
(2S)-butanoylamino]butanoylamino}propionic acid,
3-biphenyl-4-yl-3{-3-methyl-2-[4-(pyridin-2-ylamino)-
(2R)-butanoylamino]butanoylamino}propionic acid,
3-biphenyl-4-yl-3-{4-methyl-2-[4-(pyridin-2-ylamino)
butanoylamino]-(2S-)pentanoylamino}propionic acid,
3-biphenyl-4-yl-3-{4-methyl-2-[4-(pyridin-2-ylamino)
butanoylamino]-(2R)-pentanoylamino}propionic acid,
N-(1-biphenyl-4-yl-2-carboxyethyl)-3-[4-(pyridin-2-
ylamino)butanoylamino]-(2S)-succinamic acid,
N-(1-biphenyl-4-yl-2-carboxyethyl)-3-[4-(pyridin-2-
ylamino)butanoylamino]-(2R)-succinamic acid,
3-biphenyl-4-yl-3-{3-cyclohexyl-2-[4-(pyridin-2-
ylamino)butanoylamino]-(2R)-
propanoylamino}propionic acid,
4-(1-biphenyl-4-yl-2-carboxy-ethylcarbamoyl)-4-[4-(py-
ridin-2-ylamino)-butanoylamino]-(4S)-butanoic acid,

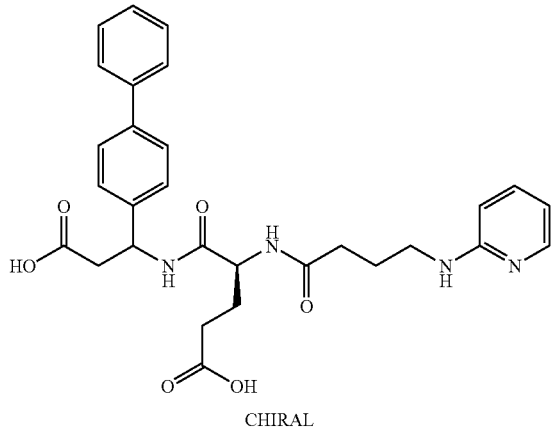
CHIRAL 3-biphenyl-4-yl-3-{3-phenyl-2-[4-(pyridin-2-ylamino)
butanoylamino]-(2R)-propanoylamino}propionic acid,
3-biphenyl-4-yl-3{-3-hydroxy-2-[4-(pyridin-2-ylamino)
butanoylamino]-(2S)-butanoylamino}propionic acid,
3-biphenyl-4-yl-3-{3-(4-hydroxyphenyl-)2-[4-(pyridin-2-
ylamino)butanoylamino]-(2S)-
propanoylamino}propionic acid,
3-biphenyl-4-yl-3-{3-phenyl-2-[4-(pyridin-2-ylamino)
butanoylamino]-(2S)-propanoylamino}propionic acid,
3-biphenyl-4-yl-3-{2-methyl-2-[4-(pyridin-2-ylamino)
butanoylamino]-propanoylamino}propionic acid,
3-biphenyl-4-yl-3-{3-hydroxy-2-[4-(pyridin-2-ylamino)
butanoylamino]-(2S)-propanoylamino}propionic acid,
3-biphenyl-4-yl-3-{3-hydroxy-2-[4-(pyridin-2-ylamino)
butanoylamino]-(2R)-propanoylamino}propionic acid,
3-biphenyl-4-yl-3-{2-[4-(pyridin-2-ylamino)butanoy-
lamino]-(2S)-hexanoylamino}propionic acid,
3-biphenyl-4-yl-3{-2-[4-(pyridin-2-ylamino)butanoy-
lamino]-(2R)-hexanoylamino}propionic acid,
3-biphenyl-4-yl-3-{2-[4-(pyridin-2-ylamino)butanoy-
lamino]-3-tritylsulfanyl-(2S)-
propanoylamino}propionic acid,
3-biphenyl-4-yl-3-{2-[4-(pyridin-2-ylamino)butanoy-
lamino]-3-tritylsulfanyl-(2R)-
propanoylamino}propionic acid,
3-biphenyl-4-yl-3-{6-amino-2-[4-(pyridin-2-ylamino)bu-
tanoylamino]-(2S)-hexanoylamino}propionic acid,
3-biphenyl-4-yl-3-{6-amino-2-[4-(pyridin-2-ylamino)bu-
tanoylamino]-(2R)-hexanoylamino}propionic acid,
3-biphenyl-4-yl-3-{2-[4-(pyridin-2-ylamino)butanoy-
lamino]-(2S)-butanoylamino}propionic acid,
3-biphenyl-4-yl-3-{3-(4-hydroxyphenyl)-2-[4-(pyridin-2-
ylamino)butanoylamino]-(2R)-
propanoylamino}propionic acid,
3-biphenyl-4-yl-3-{5-amino-2-[4-(pyridin-2-ylamino)bu-
tanoylamino]-(2R)-pentanoylamino}propionic acid,
3-biphenyl-4-yl-3-{5-guanidino-2-[4-(pyridin-2-
ylamino)butanoylamino]-(2R)-
pentanoylamino}propionic acid,
3-biphenyl-4-yl-3{-3,3-dimethyl-2-[4-(pyridin-2-
ylamino)butanoylamino]-(2R)-
butanoylamino}propionic acid,
'3-biphenyl-4-yl-3-{2-phenyl-2-[4-(pyridin-2-ylamino)
butanoylamino]-(2R)-ethanoylamino}propionic acid,
'3-biphenyl-4-yl-3-{3-hydroxy-2-[4-(pyridin-2-ylamino)
butanoylamino]-(2R)-butanoylamino}propionic acid,
3-biphenyl-4-yl-3-{4-carboxy-2-[4-(pyridin-2-ylamino)
butanoylamino]-(2R)-butanoylamino}propionic acid,
3-biphenyl-4-yl-3-{4-carbamoyl-2-[4-(pyridin-2-
ylamino)butanoylamino]-(2S)-
butanoylamino}propionic acid,
3-biphenyl-4-yl-3-{4-hydroxy-2-[4-(pyridin-2-ylamino)
butanoylamino]-(2S)-butanoylamino}propionic acid,
3-biphenyl-4-yl-3-{1-[1-(4-pyridin-2-ylaminobutanoy-
lamino)cyclohexyl]-methanoylamino}propionic acid,
3-biphenyl-4-yl-3-{-2-[4-(pyridin-2-ylamino)butanoy-
lamino]-(2R)-pentanoylamino}propionic acid,
3-biphenyl-4-yl-3-{-2-[4-(pyridin-2-ylamino)butanoy-
lamino]-(2S)-pentanoylamino}propionic acid,
3-biphenyl-4-yl-3-{3,3-dimethl-2-[4-(pyridin-2-ylamino)
butanoylamino]-(2S)-butanoylamino}propionic acid,
3-biphenyl-4-yl-3-{-3-cyclohexyl-2-[4-(pyridin-2-
ylamino)butanoylamino]-(2S)-
propanoylamino}propionic acid,
3-biphenyl-4-yl-3-{-5-guanidino-2-[4-(pyridin-2-
ylamino)butanoylamino]-(2S)-
propanoylamino}propionic acid,
3-biphenyl-4-yl-3-{-4-carbamoyl-2-[5-(pyridin-2-
ylamino)pentanoylamino]-(2S)-
butanoylamino}propionic acid,
3-biphenyl-4-yl-3-{4-hydroxy-2-[5-(pyridin-2-ylamino)
pentanoylamino]-(2S)-butanoylamino}propionic acid,
3-biphenyl-4-yl-3-{1-[1-(5-(pyridin-2-ylaminopentanoy-
lamino)cyclohexyl]-(methanoylamino}propionic acid,
3-biphenyl-4-yl-3-{-2-[5-(pyridin-2-ylamino)pentanoy-
lamino]-(2S)-pentanoylamino}propionic acid,
3-biphenyl-4-yl-3-{-2-[5-(pyridin-2-ylamino)pentanoy-
lamino]-(2R)-pentanoylamino}propionic acid,
3-biphenyl-4-yl-3-{-5-amino-2-[5-(pyridin-2-ylamino)
pentanoylamino]-(2R)-pentanoylamino}propionic
acid,
3-biphenyl-4-yl-3{-3,3-dimethyl-2-[5-(pyridin-2-
ylamino)pentanoylamino]-(2S)-
butanoylamino}propionic acid, 3-biphenyl-4-yl-3-{3-cyclohexyl-2-[5-(pyridin-2-ylamino)pentanoylamino]-(2S)-propanoylamino}propionic acid,
3-biphenyl-4-yl-3-{5-guanidino-2-[5-(pyridin-2-ylamino)pentanoylamino]-(2S)-pentanoylamino}propionic acid,
3-biphenyl-4-yl-3-{5-guanidino-2-[5-(pyridin-2-ylamino)pentanoylamino]-(2R)-pentanoylamino}propionic acid,
3-biphenyl-4-yl-3-{3-hydroxy-2-[5-(pyridin-2-ylamino)pentanoylamino]-(2R)-propanoylamino}propionic acid,
3-biphenyl-4-yl-3-{2-[5-(pyridin-2-ylamino)pentanoylamino]-(2S)-hexanoylamino}propionic acid,
3-biphenyl-4-yl-3-{2-[5-(pyridin-2-ylamino)pentanoylamino]-(2R)-hexanoylamino}propionic acid,
3-biphenyl-4-yl-3-{2-[5-(pyridin-2-ylamino)pentanoylamino]-3-tritylsulfanyl-(2S)-propanoylamino}propionic acid,
3-biphenyl-4-yl-3-{2-[5-(pyridin-2-ylamino)pentanoylamino]-3-tritylsulfanyl-(2R)-propanoylamino}propionic acid,
3-biphenyl-4-yl-3-{6-amino-2-[5-(pyridin-2-ylamino)pentanoylamino]-(2R)-hexanoylamino}propionic acid,
3-biphenyl-4-yl-3-{3-(4-hydroxyphenyl)-2-[5-(pyridin-2-ylamino)pentanoylamino]-(2S)-propanoylamino}propionic acid,
3-biphenyl-4-yl-3-{5-amino-2-[5-(pyridin-2-ylamino)pentanoylamino]-(2S)-pentanoylamino}propionic acid,
3-biphenyl-4-yl-3-{3,3-dimethyl-2-[5-(pyridin-2-ylamino)pentanoylamino]-(2R)-butanoylamino}propionic acid,
3-biphenyl-4-yl-3-{2-phenyl-2-[5-(pyridin-2-ylamino)pentanoylamino]-(2R)-ethanoylamino}propionic acid,
3-biphenyl-4-yl-3-{3-hydroxy-2-[5-(pyridin-2-ylamino)pentanoylamino]-(2R)-butanoylamino}propionic acid,
3-biphenyl-4-yl-3-{4-carboxy-2-[5-(pyridin-2-ylamino)pentanoylamino]-(2R)-butanoylamino}propionic acid,
3-biphenyl-4-yl-3-{2-[5-(pyridin-2-ylamino)pentanoylamino]-(2S)-propanoylamino}propionic acid,
3-biphenyl-4-yl-3-{2-[5-(pyridin-2-ylamino)pentanoylamino]-(2R)-propanoylamino}propionic acid,
3-biphenyl-4-yl-3-{4-methylsulfanyl-2-[5-(pyridin-2-ylamino)pentanoylamino]-(2S)-butanoylamino}propionic acid,
3-biphenyl-4-yl-3{-4-methylsulfanyl-2-[5-(pyridin-2-ylamino)pentanoylamino]-(2R)-butanoylamino}propionic acid,
3-biphenyl-4-yl-3-{3-methyl-2-[5-(pyridin-2-ylamino)pentanoylamino]-(2S)-butanoylamino}propionic acid,
3-biphenyl-4-yl-3-{3-methyl-2-[5-(pyridin-2-ylamino)pentanoylamino]-(2R)-butanoylamino}propionic acid,
3-biphenyl-4-yl-3-{4-methyl-2-[5-(pyridin-2-ylamino)pentanoylamino]-(2S)-pentanoylamino}propionic acid,
3-biphenyl-4-yl-3-{4-methyl-2-[5-(pyridin-2-ylamino)pentanoylamino]-(2R)-pentanoylamino}propionic acid,
3-biphenyl-4-yl-3-{3-carboxy-2-[5-(pyridin-2-ylamino)pentanoylamino]-(2S)-propanoylamino}propionic acid,
3-biphenyl-4-yl-3-{3-carboxy-2-[5-(pyridin-2-ylamino)pentanoylamino]-(2R)-propanoylamino}propionic acid,
3-biphenyl-4-yl-3-{3-cyclohexyl-2-[5-(pyridin-2-ylamino)pentanoylamino]-(2R)-propanoylamino}propionic acid,
3-biphenyl-4-yl-3-{4-carboxy-2-[5-(pyridin-2-ylamino)pentanoylamino]-(2S)-butanoylamino}propionic acid,
3-biphenyl-4-yl-3-{3-phenyl-2-[5-(pyridin-2-ylamino)pentanoylamino]-(2S)-propanoylamino}propionic acid,
3-biphenyl-4-yl-3-{3-phenyl-2-[5-(pyridin-2-ylamino)pentanoylamino]-(2R)-propanoylamino}propionic acid,
3-biphenyl-4-yl-3-{3-hydroxy-2-[5-(pyridin-2-ylamino)pentanoylamino]-(2S)-butanoylamino}propionic acid,
3-biphenyl-4-yl-3-{4-hydroxyphenyl-2-[5-(pyridin-2-ylamino)pentanoylamino]-(2R)-propanoylamino}propionic acid,
3-biphenyl-4-yl-3-{2-[5-(pyridin-2-ylamino)pentanoylamino]-(2S)-butanoylamino}propionic acid,
3-biphenyl-4-yl-3-{2-methyl-2-[5-(pyridin-2-ylamino)pentanoylamino]-propanoylamino}propionic acid,
3-biphenyl-4-yl-3-{3-hydroxy-2-[5-(pyridin-2-ylamino)pentanoylamino]-(2S)-propanoylamino}propionic acid,
3-biphenyl-4-yl-3-{2-phenyl-2-[5-(pyridin-2-ylamino)pentanoylamino]-(2S)-ethanoylamino}propionic acid,
3-biphenyl-4-yl-3-{4-carbamoyl-2-[5-(pyridin-2-ylamino)pentanoylamino]-(2R)-butanoylamino}propionic acid,
3-biphenyl-4-yl-3-{2-phenyl-2-[4-(pyridin-2-ylamino)butanoylamino]-(2S)-ethanoylamino}propionic acid,
3-biphenyl-4-yl-3-{4-carbamoyl-2-[4-(pyridin-2-ylamino)butanoylamino]-(2R)-butanoylamino}propionic acid,
3-biphenyl-4-yl-3-{6-amino-2-[5-(pyridin-2-ylamino)pentanoylamino]-(2S)-hexanoylamino}propionic acid,
3-biphenyl-4-yl-3-{3-tert-butylsulfanyl-2-[5-(pyridin-2-ylamino)pentanoylamino]-(2S)-propanoylamino}propionic acid,
3-biphenyl-4-yl-3-{3-tert-butphenylethanoic-2-[5-(pyridin-2-ylamino)pentanoylamino]-(2S)-propanoylamino}propionic acid,
3-biphenyl-4-yl-3-{3-(benzylsulfanyl)-2-[5-(pyridin-2-ylamino)pentanoylamino]-(2S)-propanoylamino}propionic acid,
3-biphenyl-4-yl-3-{3-(acetylaminomethylsulfanyl)-2-[5-(pyridin-2-ylamino)pentanoylamino]-(2S)-propanoylamino}propionic acid,
3-biphenyl-4-yl-3-{3-(diphenylmethylsulfanyl)-2-[5-(pyridin-2-ylamino)pentanoylamino]-(2S)-propanoylamino}propionic acid,
3-biphenyl-4-yl-3-{3-(methylsulfanyl)-2-[5-(pyridin-2-ylamino)pentanoylamino]-(2S)-propanoylamino}propionic acid,
3-biphenyl-4-yl-3-{4-trityl-2-[5-(pyridin-2-ylamino)pentanoylamino]-(2S)-butanoylamino}propionic acid,
3-biphenyl-4-yl-3-{6-trityl-2-[5-(pyridin-2-ylamino)pentanoylamino]-(2S)-hexanoylamino}propionic acid,
3-biphenyl-4-yl-3-{3-(ethylsulfanyl)-2-[5-(pyridin-2-ylamino)pentanoylamino]-(2S)-propanoylamino}propionic acid,
3-biphenyl-4-yl-3-{4-hydroxy-2-[5-(pyridin-2-ylamino)pentanoylamino]-(2R)-butanoylamino}propionic acid,
3-biphenyl-4-yl-3-{4-hydroxy-2-[4-(pyridin-2-ylamino)butanoylamino]-(2R)-butanoylamino}propionic acid,
3-biphenyl-4-yl-3-{2-[4-(pyridin-2-ylamino)-butanoylamino]4-tritylsulfanyl-(2S)-butanoylamino}propionic acid,
3-biphenyl-4-yl-3-{4-methoxy-2-[4-(pyridin-2-ylamino)butanoylamino]-(2S)-butanoylamino}propionic acid, 3-biphenyl-4-yl-3{-4-methanesulfinyl-2-[4-(pyridin-2-ylamino)butanoylamino]-(2S)-butanoylamino}propionic acid,
3-biphenyl-4-yl-3-{4-methanesulfonyl-2-[4-(pyridin-2-ylamino)butanoylamino]-(2S)-butanoylamino}propionic acid,
3-biphenyl-4-yl-3-{3-benzyloxy-2-[4-(pyridin-2-ylamino)butanoylamino]-(2S)-propanoylamino}propionic acid,
3-biphenyl-4-yl-3-{6-ureido-2-[4-(pyridin-2-ylamino)butanoylamino]-(2S)-hexanoylamino}propionic acid,
3-biphenyl-4-yl-3-{6-benzyloxycarbonylamino-2-[4-(pyridin-2-ylamino)butanoylamino]-(2S)-hexanoylamino}propionic acid,
3-biphenyl-4-yl-3-{6-acetylamino-2-[4-(pyridin-2-ylamino)butanoylamino]-(2S)-hexanoylamino}propionic acid,
3-biphenyl-4-yl-3-{6-allyloxycarbonylamino-2-[4-(pyridin-2-ylamino)butanoylamino]-(2S)-hexanoylamino}propionic acid,
3-biphenyl-4-yl-3{-4-tritylsulfanyl-2-[5-(pyridin-2-ylamino)pentanoylamino]-(2S)-butanoylamino}propionic acid,
3-biphenyl-4-yl-3{-4-methoxy-2-[5-(pyridin-2-ylamino)pentanoylamino]-(2S)-butanoylamino}propionic acid,
3-biphenyl-4-yl-3-{4-methanesulfinyl-2-[5-(pyridin-2-ylamino)pentanoylamino]-(2S)-butanoylamino}propionic acid,
3-biphenyl-4-yl-3-{4-methanesulfonyl-2-[5-(pyridin-2-ylamino)pentanoylamino]-(2S)-butanoylamino}propionic acid,
3-biphenyl-4-yl-3-{3-benzyloxy-2-[5-(pyridin-2-ylamino)pentanoylamino]-(2S)-propanoylamino}propionic acid,
3-biphenyl-4-yl-3-{6-ureido-2-[5-(pyridin-2-ylamino)pentanoylamino]-(2S)-hexanoylamino}propionic acid,
3-biphenyl-4-yl-3-{6-benzyloxycarbonylamino-2-[5-(pyridin-2-ylamino)pentanoylamino]-(2S)-hexanoylamino}propionic acid,
3-biphenyl-4-yl-3-{6-acetylamino-2-[5-(pyridin-2-ylamino)pentanoylamino]-(2S)-hexanoylamino}propionic acid,
3-biphenyl-4-yl-3-{6-allyloxycarbonylamino-2-[5-(pyridin-2-ylamino)pentanoylamino]-(2S)-hexanoylamino}propionic acid,
3-biphenyl-4-yl-3-{4-tritylsulfanyl-2-[6-(pyridin-2-ylamino)hexanoylamino]-(2S)-butanoylamino}propionic acid,
3-biphenyl-4-yl-3-{4-methoxy-2-[6-(pyridin-2-ylamino)hexanoylamino]-(2S)-butanoylamino}propionic acid,
3-biphenyl-4-yl-3{-4-methanesulfinyl-2-[6-(pyridin-2-ylamino)hexanoylamino]-(2S)-butanoylamino}propionic acid,
3-biphenyl-4-yl-3-{4-methanesulfonyl-2-[6-(pyridin-2-ylamino)hexanoylamino]-(2S)-butanoylamino}propionic acid,
3-biphenyl-4-yl-3-{3-benzyloxy-2-[6-(pyridin-2-ylamino)hexanoylamino]-(2S)-propanoylamino}propionic acid,
3-biphenyl-4-yl-3{-6-ureido-2-[6-(pyridin-2-ylamino)hexanoylamino]-(2S)-hexanoylamino}propionic acid,
3-biphenyl-4-yl-3-{6-benzyloxycarbonylamino-2-[6-(pyridin-2-ylamino)hexanoylamino]-(2S)-hexanoylamino}propionic acid,
3-biphenyl-4-yl-3-{6-acetylamino-2-[6-(pyridin-2-ylamino)hexanoylamino]-(2S)-hexanoylamino}propionic acid,
3-{3-benzyloxy-2-[5-(pyridin-2-ylamino)pentanoylamino]propionylamino}-3-(3-chlorophenyl)propionic acid,
3-{3-benzyloxy-2-[5-(pyridin-2-ylamino)pentanoylamino]propionylamino}-3-(3-bromophenyl)propionic acid, or
3-{3-benzyloxy-2-[5-(pyridin-2-ylamino)pentanoylamino]propionylamino}-3-(4-chlorophenyl)propionic acid, or a physiologically acceptable salt thereof.

3. A process for preparing a compound of formula I according to claim 1 or a salt thereof, comprising
(a) reacting a compound of formula II

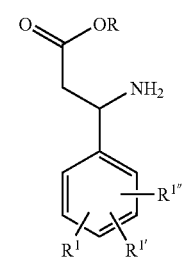

in which R is a protecting group, and $R^1$, $R^{1'}$ and $R^{1''}$ are as defined in formula I and in which, in the case where $R^1$, $R^{1'}$ and/or $R^{1''}$ has a free hydroxyl or amino group, this is in each case protected by a protecting group,
with a compound of formula III

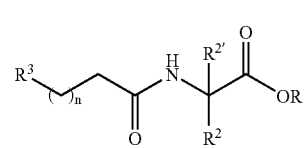

in which $R^2$, $R^{2'}$, $R^3$ and n are as defined in formula I and in which, in the case where $R^2$, $R^{2'}$ and/or $R^3$ contain free hydroxyl or amino groups, these are in each case protected by protecting groups,
and removing the protecting group R and any protecting groups present on $R^1$, $R^{1'}$, $R^{1''}$, $R^2$, $R^{2'}$ and/or $R^3$,
or
(b) reacting a compound of formula IV

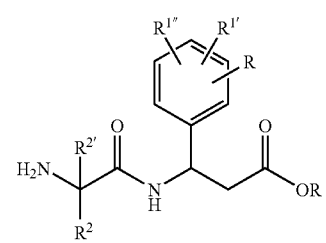

in which R is a protecting group, and $R^1$, $R^{1'}$, $R''$, $R^2$ and $R^{2'}$ are as defined in formula I and in which, in the case where $R^1$, $R^{1'}$, $R^{1''}$, $R^2$ and/or $R^{2'}$ contain free hydroxyl and/or amino groups, these are in each case protected by protecting groups, with a compound of formula V

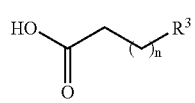

in which n and $R^3$ are as defined in formula I and in which, in the case where $R^1$, $R^{1'}$ and/or $R^{1''}$ contains free hydroxyl and/or amino groups, these are in each case protected by protecting groups, and removing the protecting group R and any protecting groups present on $R^1$, $R^{1'}$, $R^{1''}$, $R^2$ and/or $R^3$, or (c) converting one or more radicals $R^1$, $R^{1'}$, $R^{1''}$, $R^2$ and/or $R^3$ in a compound of the formula I are converted into one or more different radicals $R^1$, $R^{1'}$, $R^{1''}$, $R^2$ and/or $R^3$ or (d) reacting a compound of the formula II with a compound of formula VI

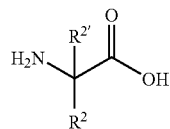

in which $R^2$ and $R^{2'}$ are as defined in formula I and in which, in the case where $R^2$ and/or $R^{2'}$ contain free hydroxyl and/or amino groups, these are protected by protecting groups, to give a compound of the formula IV, which is subsequently reacted with a compound of formula V as described in (b), and removing the protecting group R and any protecting groups present on $R^1$, $R^2$, $R^{2'}$ and/or $R^3$, and/or a basic or acidic compound of the formula I is converted into one of its salts by treatment with an acid or base.

4. A composition comprising a compound according to claim 1 and a pharmaceutically acceptable carrier.

5. A process according to claim 3, wherein converting one or more radicals $R^1$, $R^{1'}$, $R^{1''}$, $R^2$ and/or $R^3$ in a compound of the formula I into one or more radicals $R^1$, $R^{1'}$, $R^{1''}$, $R^2$ and/or $R^3$ is achieved by i) alkylating a hydroxyl group,
ii) hydrolysing an ester group to a carboxyl group,
iii) esterifying a carboxyl group,
iv) alkylating an amino group,
v) reacting an aryl bromide or iodide with a boronic acid by a Suzuki coupling to give the corresponding coupling product, or
vi) acylating an amino group.

6. A compound according to claim 1, which is a salt of a compound of formula I.

7. A method of inhibiting an $\alpha_v\beta_6$ integrin, comprising administering an effective amount of a composition according to claim 4.

8. A compound according to claim 1, wherein Ar is monosubstituted phenyl, and/or $Het^2$ is 4-pyridyl.

9. A compound of formula I

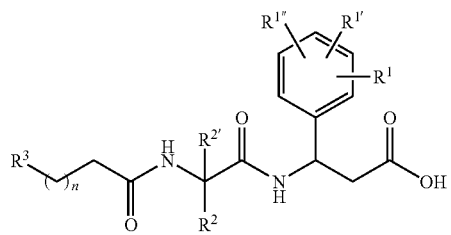

in which
$R_1$, $R_{1'}$ and $R^{1'''}$ are H or phenyl,
$R_2$ is A, Ar, $(CH_2)_mXA$, $(CH_2)_mOH$, $(CH_2)_mNH_2$, $(CH_2)_m$NHA, $(CH_2)_mNA_2$, $(CH_2)_mNHCOA$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_m$XCOYA, $(CH_2)_mXCOY(CH_2)_oAr$, $(CH_2)_mX(CH_2)_o$YA, $(CH_2)_mX(CH_2)_oNHCOA$, $(CH_2)_mNHCONHR_{2'}$, $(CH_2)_mCH_2A$, $(CH_2)_mCHA_2$, $(CH_2)_mCA_3$, $(CH_2)_mAr$, $(CH_2)_mCHAr_2$, $(CH_2)_mCAr_3$, $(CH_2)_m$cycloalkyl, $(CH_2)_m$—NH—C(=NH)—$NH_2$, or $(CH_2)_m$—(HN=)C—$NH_2$, where X and Y, independently of one another, are S, O, S=O, $SO_2$ or NH, where, if $R^2$=$(CH_2)_m$X-COYA or $(CH_2)_mXCOY(CH_2)_oAr$, X and Y cannot be S=O or $SO_2$,
$R^{2'}$ is H or A,
$R_3$ is $Het^2$-NH—, where the primary amino group is optionally provided with an amino-protecting group,
A is alkyl having from 1 to 8 carbon atoms,
Ar is phenyl, naphthyl, anthranyl or biphenyl, each of which is unsubstituted or monosubstituted or polysubstituted by Hal, A, OA, OH, CO-A, CN, COOA, COOH, $CONH_2$, CONHA, $CONA_2$, $CF_3$, $OCF_3$ or $NO_2$,
$Het^2$ is 2-, 3- or 4-pyridyl, which is unsubstituted or monosubstituted or disubstituted by A, NHA and/or $NH_2$,
Hal F, Cl, Br or iodine,
m is 0, 1, 2, 3, 4, 5, 6 or 8,
n is 1, 2, 3, 4, 5 or 6, and
o is 0, 1, 2 or 3,
or a physiologically acceptable salt thereof.

10. A compound according to claim 1, which is in the form of a stereoisomer.

11. A compound according to claim 2, which is in the form of a stereoisomer.

12. A compound according to claim 1, wherein n is 3.

13. A compound according to claim 1, wherein
$R^2$ is Ar, $(CH_2)_mXA$, $(CH_2)_mOH$, $(CH_2)_mNH_2$, $(CH_2)_m$NHA, $(CH_2)_mNA_2$, $(CH_2)_mNHCOA$, $(CH_2)_mNO_2$, $(CH_2)_mCOOR^1$, $(CH_2)_mCONH_2$, $(CH_2)_mX(CH_2)_oAr$, $(CH_2)_mX(CH_2)_oCHAr_2$, $(CH_2)_mX(CH_2)_oCAr_3$, $(CH_2)_m$XCOYA, $(CH_2)_mXCOY(CH_2)_oAr$, $(CH_2)_mX(CH_2)_o$YA, $(CH_2)_mX(CH_2)_oNHCOA$, $(CH_2)_mNHCONHR^{2'}$, $(CH_2)_mCH_2A$, $(CH_2)_mCHA_2$, $(CH_2)_mCA_3$, $(CH_2)_mAr$, $(CH_2)_mCHAr_2$, $(CH_2)_mCAr_3$, $(CH_2)_m$cycloalkyl, $(CH_2)_m$NH—C(=NH)—$NH_2$, or $(CH_2)_m$—(HN=)C—$NH_2$.

14. A compound according to claim 1, wherein $R^1$ is phenyl.

15. A compound according to claim 1, wherein n is 2 to 6.

16. A compound according to claim 1, wherein $R^{2'}$ is A.

17. A compound according to claim 1, wherein A in $R^2$ is an alkyl having 2-8 carbon atoms.

18. A compound according to claim 1, wherein A is an unsubstituted alkyl group.

19. A compound according to claim 2, which is a salt of said compound.

20. A compound according to claim 1, wherein n is 2 to 4.

21. A composition comprising a compound according to claim 2 and a pharmaceutically acceptable carrier.

22. A compound of claim 1, wherein
$R^3$ is $Het^2$-NH—, wherein the primary amino group is not provided with an amino-protecting group.

23. A compound of claim 9, wherein
$R_3$ is $Het_2$-NH—, wherein the primary amino group is not provided with an amino-protecting group.

24. A composition comprising a compound according to claim 22 and a pharmaceutically acceptable carrier.

25. A composition comprising a compound according to claim 23 and a pharmaceutically acceptable carrier.

26. A method of inhibiting an $\alpha_v\beta_6$ integrin, comprising administering an effective amount of a composition according to claim 21.

* * * * *

UNITED STATES PATENT AND TRADEMARK OFFICE
CERTIFICATE OF CORRECTION

| | | |
|---|---|---|
| PATENT NO. | : 7,632,951 B2 | Page 1 of 1 |
| APPLICATION NO. | : 10/471836 | |
| DATED | : December 15, 2009 | |
| INVENTOR(S) | : Oliver Schadt et al. | |

It is certified that error appears in the above-identified patent and that said Letters Patent is hereby corrected as shown below:

Column 54, line 43 reads: (CHEMICAL NAME)

Should read: --3-biphenyl-4-yl-3-{5-amino-2-[4-(pyridin-2-ylamino)butanoyl-amino]-(2S)-pentanoylamino}propionic acid,--

Column 62, line 2 reads: "$R^3$ is $Het_2$-NH-, wherein the primary amino group is not"

Should read: --$R^3$ is $Het^2$-NH-, wherein the primary amino group is not--

Signed and Sealed this
Twenty-fifth Day of January, 2011

David J. Kappos
*Director of the United States Patent and Trademark Office*